United States Patent
Statsyuk et al.

(10) Patent No.: US 10,723,702 B2
(45) Date of Patent: Jul. 28, 2020

(54) PHOTOCROSSLINKING REAGENTS AND METHODS OF USE THEREOF

(71) Applicant: Northwestern University, Evanston, IL (US)

(72) Inventors: Alexander V. Statsyuk, Evanston, IL (US); David T. Krist, Evanston, IL (US); Neil L. Kelleher, Evanston, IL (US); Luis Henrique Ferreira do Vale, Brasilia (BR); Heeseon An, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/735,020

(22) PCT Filed: Jun. 9, 2016

(86) PCT No.: PCT/US2016/036561
§ 371 (c)(1),
(2) Date: Dec. 8, 2017

(87) PCT Pub. No.: WO2016/201025
PCT Pub. Date: Dec. 15, 2016

(65) Prior Publication Data
US 2018/0170878 A1    Jun. 21, 2018

Related U.S. Application Data

(60) Provisional application No. 62/173,129, filed on Jun. 9, 2015.

(51) Int. Cl.
*A61K 31/396* (2006.01)
*C07D 229/02* (2006.01)
*C12Q 1/48* (2006.01)
*C12N 9/10* (2006.01)
*C12N 9/00* (2006.01)

(52) U.S. Cl.
CPC .......... *C07D 229/02* (2013.01); *A61K 31/396* (2013.01); *C12N 9/104* (2013.01); *C12N 9/93* (2013.01); *C12Q 1/48* (2013.01); *C12Y 603/02019* (2013.01); *G01N 2333/9015* (2013.01); *G01N 2333/91074* (2013.01); *G01N 2560/00* (2013.01)

(58) Field of Classification Search
None
See application file for complete search history.

(56) References Cited

U.S. PATENT DOCUMENTS 3,509,131 A    4/1970  Church
8,071,718 B2   12/2011 Padilla De Jesus et al.

FOREIGN PATENT DOCUMENTS

WO    WO 2011053697 A1    5/2011

OTHER PUBLICATIONS

Database Registry Chemical Abstracts Service, Columbus, Ohio, Accession No. RN 1407594-45-9, Entered STN: Nov. 28, 2012.*
An et al., Development of Activity-Based Probes for Ubiquitin and Ubiquitin-like Protein Signaling Pathways, J Am Chem Soc, vol. 135(45), pp. 16948-16962, 2013.
Brown et al., Strategy for "Detoxification" of a Cancer-Derived Histone Mutant Based on Mapping Its Interaction with the Methyltransferase PRC2, J Am Chem Soc, vol. 136(39), pp. 13498-13501, 2014.
Chou et al., Genetically encoding an aliphatic diazirine for protein photocrosslinking, Chem Sci, vol. 2, pp. 480-483, 2011.
Cooper et al., Biochemical Analysis of Angelman Syndrome-associated Mutations in the E3 Ubiquitin Ligase E6-associated Protein, J Biol Chem, vol. 279(39), pp. 41208-41217, 2004.
Eletr et al., Sequence Determinants of E2-E6AP Binding Affinity and Specificity, J Mol Biol, vol. 369(2), pp. 419-428, 2007.
Huang et al., Structure of an E6AP-UbcH7 Complex: Insights into Ubiquitination by the E2-E3 Enzyme Cascade, Science, vol. 2865443, pp. 1321-1326, 1999.
International Search Report of related PCT/US16/36561, dated Oct. 6, 2016, 13 pages.
Kishino et al., UBE3A/E6-AP mutations cause Angelman syndrome, Nat Gen, vol. 15, pp. 70-73, 1997.
Krist et al., Catalytically Important Residues of E6AP Ubiquitin Ligase Identified Using Acid-Cleavable Photo-Cross-linkers, Biochemistry, vol. 54(29), pp. 4411-4414, 2015.
Mackinnon et al., Photo-leucine incorporation reveals the target of a cyclodepsipeptide inhibitor of cotranslational translocation, J Am Chem Soc, vol. 129(47), pp. 14560-14561, 2007.
Nuber et al., Cloning of Human Ubiquitin-conjugating Enzymes UbcH6 and UbcH7 (E2-F1) and Characterization of Their Interaction with E6-AP and RSP5, J Biol Chem, vol. 271(5), pp. 2795-2800, 1996.
Purbeck et al, Kinetics of the Transfer of Ubiquitin from UbcH7 to E6AP, Biochemistry, vol. 49(7), pp. 1361-1363, 2010.
Ronchi et al., E6AP/UBE3A Ubiquitin Ligase Harbors Two E2-ubiquitin Binding Sites, J Biol Chem, vol. 288, 27 pages, 2013.
Ronchi et al., The Active Form of E6-associated protein (E6AP)/UBE3A Ubiquitin Ligase Is an Oligomer, J Biol Chem, vol. 289(2), pp. 1033-1048, 2014.
Scheffner et al., Protein ubiquitination involving an E1-E2-E3 enzyme ubiquitin thioester cascade, Nature, vol. 373, pp. 81-83, 1995.
Scheffner et al., The HPV-16 E6 and E6-AP complex functions as a ubiquitin-protein ligase in the ubiquitination of p53, Cell, vol. 75(3), pp. 495-505, 1993.
Tran et al., Gel-Eluted Liquid Fraction Entrapment Electrophoresis: An Electrophoretic Method for Broad Molecular Weight Range Proteome Separation, Anal Chem, vol. 80(5), pp. 1568-1573, 2008.

(Continued)

Primary Examiner — Samantha L Shterengarts
(74) Attorney, Agent, or Firm — Casimir Jones SC; David W. Staple

(57) ABSTRACT

Provided herein are photocrosslinking reagents, crosslinkable proteins displaying photocrosslinking groups, cross-linked protein-protein complexes, and methods of use thereof.

20 Claims, 34 Drawing Sheets
Specification includes a Sequence Listing.

(56) References Cited

OTHER PUBLICATIONS

Varshavsky, The ubiquitin system, an immense realm, Ann. Rev. Biochem, vol. 81, pp. 167-176, 2012.
Verdecia et al., Conformational Flexibility Underlies Ubiquitin Ligation Mediated by the WWP1 HECT Domain E3 Ligase, Mol Cell, vol. 11(1), pp. 249-259, 2003.
Wilm et al., Analytical Properties of the Nanoelectrospray Ion Source, Anal Chem, vol. 68(1), pp. 1-8, 1996.
Yang et al., Identification of cross-linked peptides from complex samples, Nature Methods, vol. 9, pp. 904-906, 2012.

* cited by examiner

E6AP HECT
UbcH7 CΔS E93C -diazirine

E6AP HECT
UbcH7 CΔS E93C Ub -diazirine

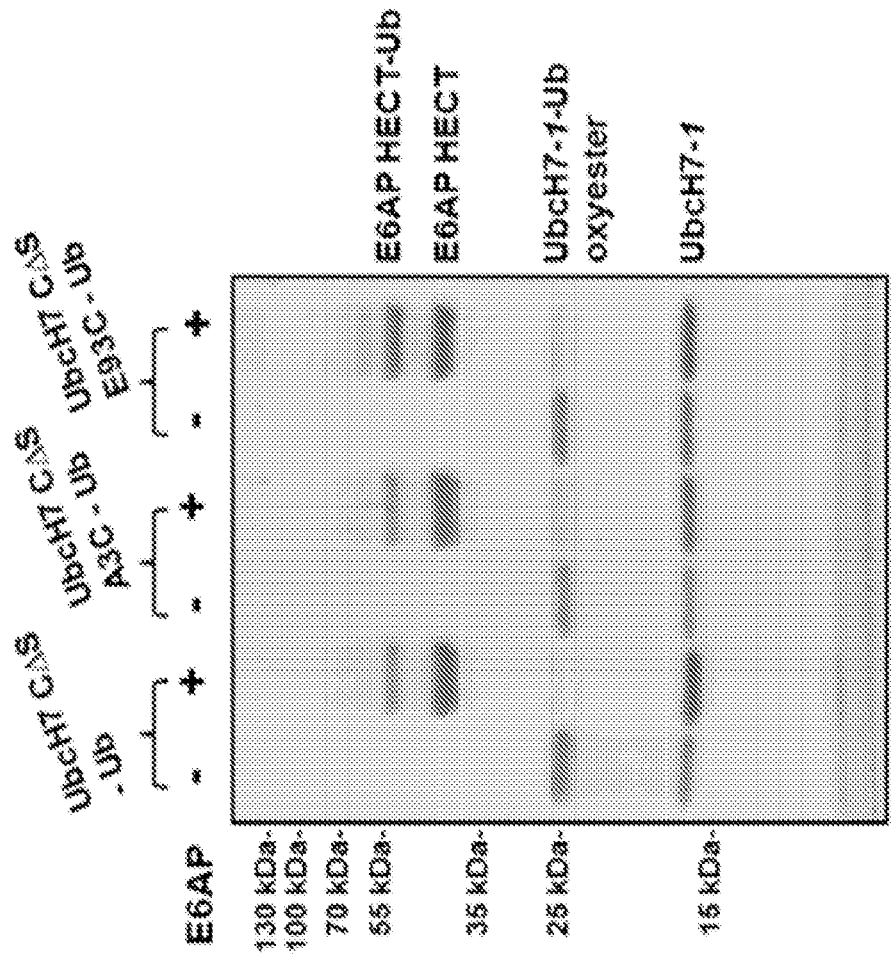
FIG. 5C
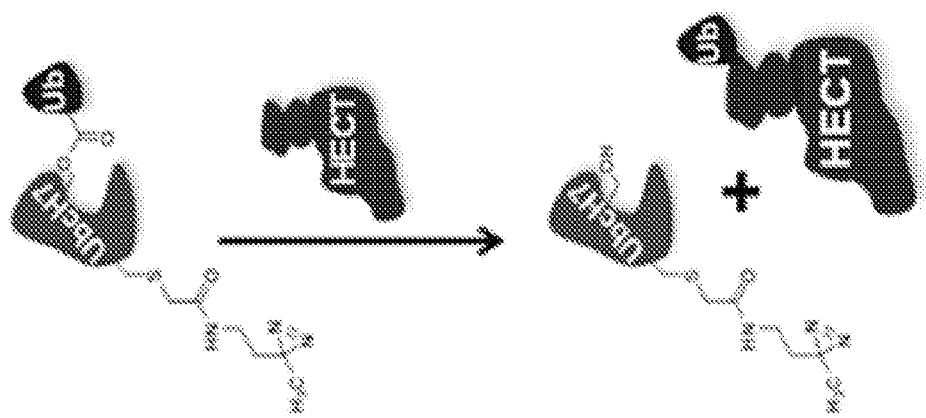

FIG. 12B
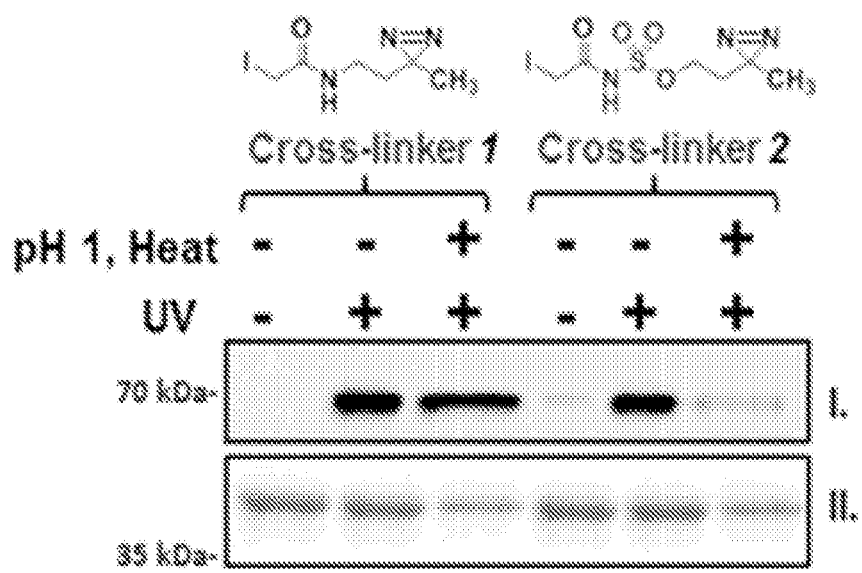
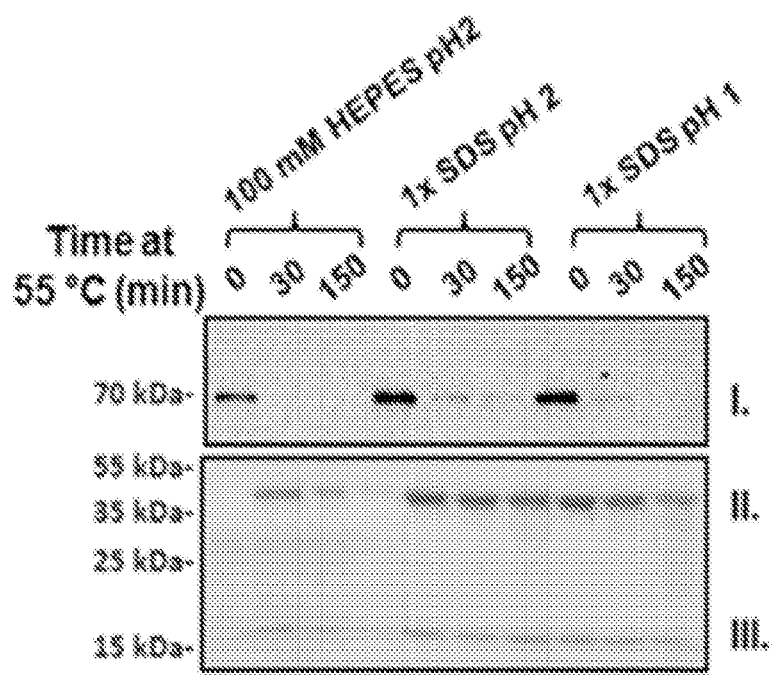
FIG. 12C

FIG. 14B
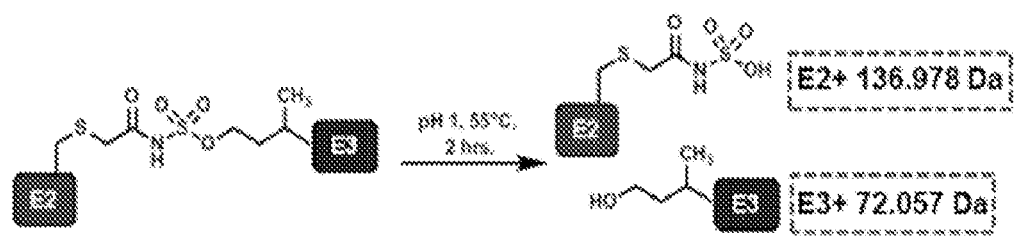
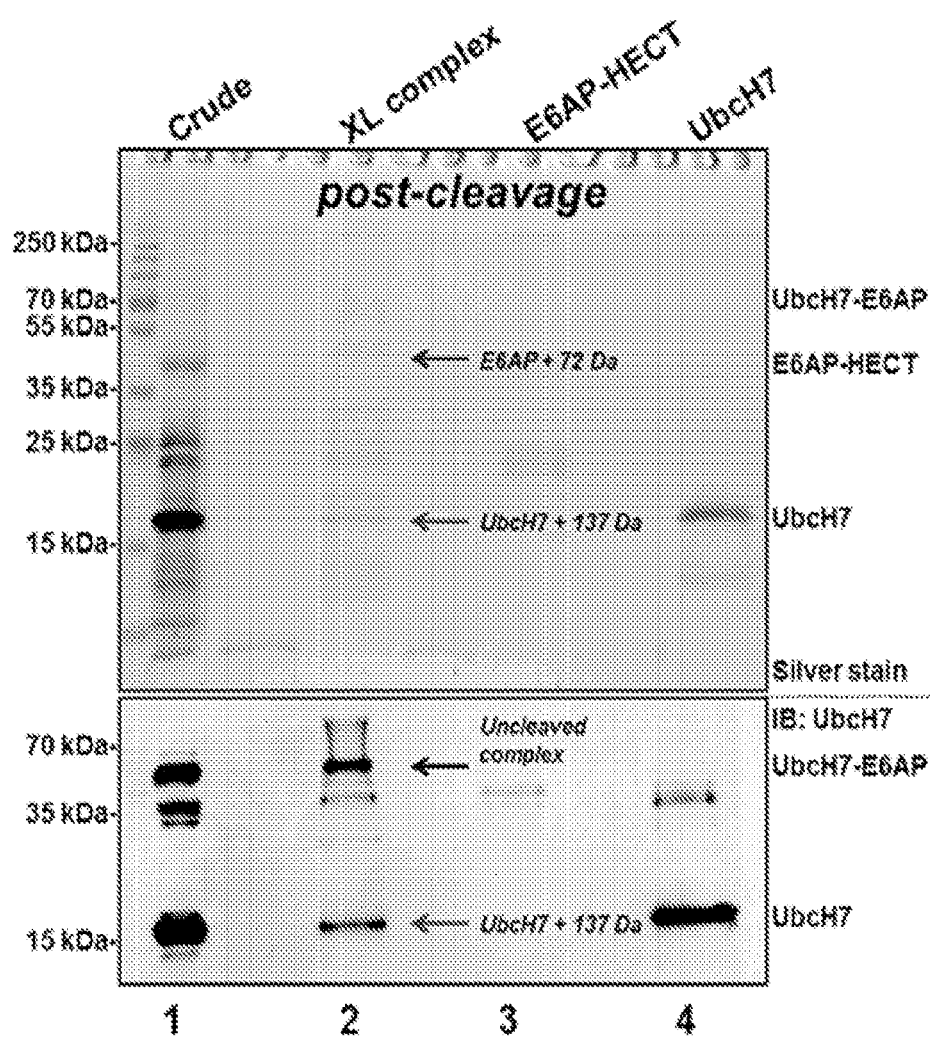
FIG. 14C

FIG. 15A
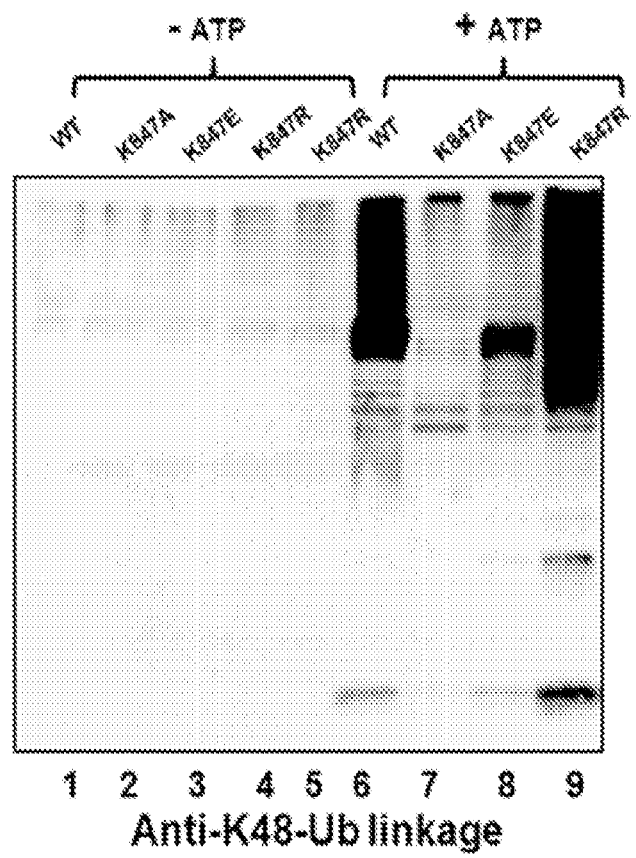
Anti-K48-Ub linkage
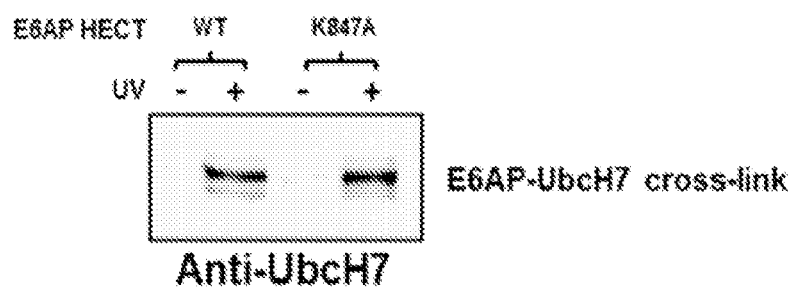
FIG. 15B

PHOTOCROSSLINKING REAGENTS AND METHODS OF USE THEREOF

CROSS-REFERENCE TO RELATED APPLICATIONS

The present invention claims priority to U.S. Provisional Patent Application Ser. No. 62/171,129, filed Jun. 9, 2015, which is incorporated by reference in its entirety.

FIELD

Provided herein are photocrosslinking reagents, crosslinkable proteins displaying photocrosslinking groups, crosslinked protein-protein complexes, and methods of use thereof.

BACKGROUND

Protein-protein interactions play an important role in biology, and modulating protein-protein interactions have been recognized as a successful strategy for drug discovery. One unmet need in the field is to be able to covalently trap two interacting proteins in vitro and identify covalently crosslinked sites on two proteins. Since only proximal residues of two proteins are crosslinked, identification of crosslinked sites allows mapping proximal protein-protein interfaces in solution. The resulting knowledge is useful in the design of agents (e.g., small molecules, peptides, antibodies, etc.) that modulate (e.g., inhibit or promote) such protein-protein interactions for therapeutic purposes.

SUMMARY

Provided herein are photocrosslinking reagents, crosslinkable proteins displaying such photocrosslinking reagents, crosslinked protein-protein complexes, and methods of use thereof.

In some embodiments, the compositions and methods herein provide for the site-specific installation of diazirine containing photocrosslinker on the surface of a first protein. The photoreactive protein (e.g., purified or unpurified) is irradiated with UV light in the presence of a second protein; if the first and second proteins associate near the site of the photocrosslinker, the proteins become photocrosslinked, allowing for identification of interacting sites between the two proteins. In some embodiments, provided herein are reagents for rapid scanning and detection of proximal protein-protein interfaces. In some embodiments, these reagents are coupled with protocols that utilize an electroelutian device to isolate photocrosslinked protein complexes from SDS PAGE gel.

Compositions and methods herein find use, for example, in the detection of weak protein-protein interactions, and identification of proximal amino acid residues at protein-protein interfaces. In some embodiments, reagents comprise two protein reactive moieties. In some embodiments, the protein reactive moieties are connected by a linker. In some embodiments, a first protein reactive moiety allows for chemical reaction with a site on a first protein (e.g., without photo-initiation of reaction). In some embodiments, the first protein reactive moiety allows for site-specific attachment of the reagent to the first protein (e.g., at a specific amino acid residue (e.g., cysteine, lysine, non-natural amino acid, etc.)). A suitable first reactive moiety is an iodoacetamide group. In some embodiments, a second protein reactive moiety allows for light-induced covalent reaction with a site on a second protein. In some embodiments, the second protein reactive moiety allows for non-specific attachment of the reagent to the second protein (e.g., at a any amino acid within a suitable proximity). A suitable second reactive moiety is a diazirine group. In some embodiments, the photocrosslinking reagents herein are small in size (e.g., <5000 g/mol, <2000 g/mol, <1000 g/mol, <750 g/mol, <500 g/mol, etc.) and minimize interference with the protein-protein interactions of the associated proteins. In some embodiments, crosslinking reagents are cleavable (e.g., comprise a cleavable linker between protein reactive moieties). In some embodiments, a cleavable linker is photocleavable, pH-cleavable, enzymatically-cleavable, chemically-cleavable, etc. In some embodiments, cleavable linkers facilitate downstream analysis (e.g., mass spectrometry analysis) of the crosslinked proteins (e.g., the captured second protein) and identification of photocrosslinked sites. In some embodiments, linkers are compatible with reducing conditions, and allow acid mediated cleavage of photocrosslinked peptides. In some embodiments, photocrosslinking reagents are isotopically labeled (e.g., deuterated).

In some embodiments, provided herein are compositions comprising a photocrosslinkable compound comprising an iodoacetamide group covalently linked to a diazirine group. In some embodiments, the compound comprises Formula I:

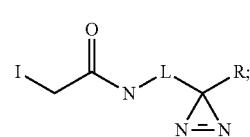
(Formula I)

wherein L is selected from a direct covalent bond, alkyl, substituted alkyl, heteroalkyl, substituted heteroalkyl, and/or a cleavable moiety; and
wherein R is selected from H, alkyl, substituted alkyl, heteroalkyl, substituted heteroalkyl.

In some embodiments, the compound comprises Formula II:

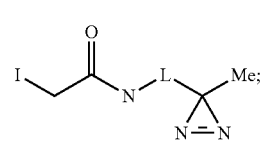
(Formula II)

wherein L is selected from a direct covalent bond, alkyl, substituted alkyl, heteroalkyl, substituted heteroalkyl, and/or a cleavable moiety.

In some embodiments, the compound comprises Formula III:

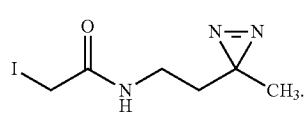
(Formula III)

In some embodiments, L comprises a cleavable moiety. In some embodiments, the cleavable moiety is photocleavable, chemically cleavable (e.g., by a cleavage agent), pH cleavable (e.g., acid labile, base labile, etc.), or enzymatically cleavable. In some embodiments, the cleavable moiety is N-acylsulfamate.

In some embodiments, the compound comprises Formula IV:

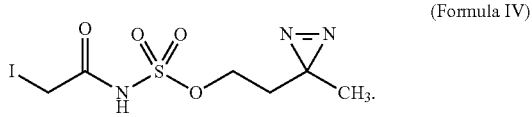 [SMILES: CC1(CCOS(=O)(=O)NC(=O)CI)N=N1]

(Formula IV)

In some embodiments, the compound is isotopically-labelled at one or more positions. In some embodiments, the compound is isotopically-labelled at one or more positions with a non-natural abundance of stable heavy isotopes. In some embodiments, one or more hydrogen positions on the compound are deuterium. In some embodiments, the compound comprises Formula V:

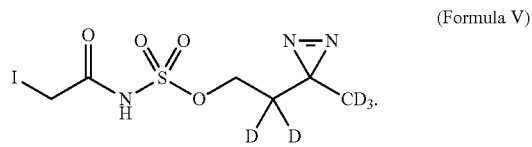 [SMILES: [2H]C([2H])([2H])C1(C([2H])([2H])COS(=O)(=O)NC(=O)CI)N=N1]

(Formula V)

In some embodiments, provided herein are methods of crosslinking a first protein to a second protein, comprising: (a) reacting the iodoacetamide group of a photocrosslinking reagent herein with a thiol group of the first protein; (b) exposing the diazirine group to UV irradiation in the presence of the second protein, wherein a the diazirine group forms a covalent bond with any adjacent amino acid on the second protein, in the presence of the UV irradiation, if the amino acid and diazirine group are within proximity.

In some embodiments, provided herein are compositions comprising a protein displaying a diazirine group following reaction of a thiol of a cysteine of the protein with the iodoacetamide group of photocrosslinking reagent herein.

In some embodiments, provided herein are compositions comprising a first protein to a second protein crosslinked to each other by a photocrosslinking reagent herein.

In some embodiments, provided herein are methods comprising: (a) chemically-linking the iodoacetamide group of a compound of a composition of one of claims 1-12 to a protein of interest (POI) to produce a photocrosslinkable POI displaying the diazirine group; (b) adding the photocrosslinkable POI to a sample comprising one or more candidate proteins; (c) exposing to the sample to UV irradiation to initiate photocrosslinking of the diazirine group displayed by the photocrosslinkable POI with any residue on one or more of the candidate proteins in the sample, if the residues are in close proximity to the diazirine group. In some embodiments, close proximity is a distance less than 20 Å (e.g., 19 Å, 18 Å, 17 Å, 16 Å, 15 Å, 14 Å, 13 Å, 12 Å, 11 Å, 10 Å, 9 Å, 8 Å, 7 Å, 6 Å, 5 Å, 4 Å, 3 Å, 2 Å, 1 Å, or less, or any ranges therebetween). In some embodiments, photocrosslinking occurs if the photocrosslinkable POI and a candidate protein are associated in an orientation to present the residue in close proximity to the diazirine group. In some embodiments, photocrosslinking occurs if the photocrosslinkable POI and a candidate protein are in a protein-protein complex.

In some embodiments, the sample is a cell lysate. In some embodiments, the POI is engineered to present a specific position for chemically-linking to the iodoacetamide group.

In some embodiments, one or more candidate proteins are of known identity. In some embodiments, one or more candidate proteins are of unknown identity. In some embodiments, one or more candidate proteins are engineered to present an amino acid at a specific position for photocrosslinking to the diazirine group.

In some embodiments, methods further comprise purifying the photocrosslinked POI/candidate protein from the sample. In some embodiments, purifying comprises gel electrophoresis.

In some embodiments, methods further comprise excising a band comprising the photocrosslinked POI/candidate protein from the gel, and/or electroeluting the photocrosslinked POI/candidate protein from the band and/or gel.

In some embodiments, methods further comprise cleaving the photocrosslinking reagent connecting the POI to the candidate protein. In some embodiments, cleaving the crosslinking reagent comprises exposing the photocrosslinking reagent to acidic conditions.

In some embodiments, methods further comprise digesting the cleaved POI, cleaved candidate protein, or photocrosslinked POI/candidate protein to produce peptide fragments. In some embodiments, methods further comprise analyzing the peptide fragments to identify the candidate protein and/or to identify the amino acid in the POI and/or candidate protein involved in the photocrosslinking. In some embodiments, analyzing is by mass spectrometry.

In some embodiments, provided herein are methods of synthesizing the photocrosslinking reagents described herein (See, e.g., the reagents and methods of Example 1). In some embodiments, methods are provided for synthesizing a deuterated alkyl-diazirine compound from a deuterated alkyl-ketone compound, comprising exposing the deuterated alkyl-ketone to NH$_3$, wherein all or a portion of deuterated positions on the alkyl chain of the deuterated alkyl-ketone compound remain deuterated in the deuterated alkyl-diazirine compound (See, e.g., Scheme S3). In some embodiments, the deuterated alkyl-diazirine and deuterated alkyl-ketone compounds comprise substituted alkyl chains. In some embodiments, the deuterated alkyl-diazirine and deuterated alkyl-ketone compounds comprise terminal OH and OD groups respectively. In some embodiments, compound 6

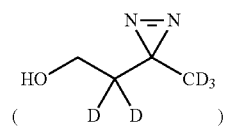

is synthesized from compound 5

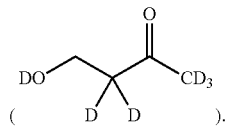

.

BRIEF DESCRIPTION OF THE DRAWINGS

FIGS. 5A-C. Crosslinker-modified UbcH7 charged with ubiquitin. UbcH7 C86S-Ub oxyester interacts with E6AP to transfer ubiquitin. (A.) Each alkylated mutant is competent to form an UbcH7 C86S-Ub oxyester except when the catalytic cysteine C86 is alkylated with crosslinker (lane 9). UbcH7 mutants alkylated by crosslinker 1 at the indicated residue (5 µM) were incubated with Ube1 (200 nM), ubiquitin (10 µM) in the dark at 37° C. for 15 hours in 25 mM HEPES pH 7.5, 50 mM NaCl, 10 mM MgCl$_2$, 1 mM DTT with or without ATP (185 µM). Reactions were quenched with 6× Laemmli buffer with β-ME and incubated at room temperature for 5 minutes without boiling. The "*" marks a faint GST impurity. (B) Same conditions as in part A. The presence of crosslinker 2 on UbcH7 CΔS E93C does not affect the efficiency of UbcH7-Ub oxyester formation. This indicates that crosslinker 2 does not perturb enzyme structure upon alkylation. (C.) UbcH7 CΔS-Ub oxyester alkylated with crosslinker transfers ubiquitin to E6AP HECT (compare to FIG. 2B where E6AP HECT is a single band). This indicates that crosslinker 1 does not interfere with the UbcH7/E6AP interaction. UbcH7-Ub oxyester (5 µM) was incubated with or without E6AP-HECT (5 µM) in PBS(B) for 20 hours at room temperature. Reactions were quenched with 6× Laemmli buffer with β-ME and incubated at room temperature for 5 minutes without boiling.

FIGS. 12A-E. Mass spectrometry protocol to identify crosslinker modifications on E6AP. A. The band corresponding to the crosslinked UbcH7-E6AP complex was excised and loaded to the denaturing electroelution device. After eluting complexes from the gels, photocrosslinked protein complexes were cleaved under acidic conditions, trypsinized, and then analyzed. B. Crosslinker 2 is cleavable at pH 1, 55° C. I. UbcH7-E6AP crosslink. II. E6AP-HECT. C. By conducting the acidic cleavage of photocrosslinked proteins in Tris-Glycine-SDS buffer, we avoided hydrolysis of the peptide backbone. I. UbcH7-E6AP crosslink. II. E6AP-HECT. III. UbcH7. D. $MS^2$ identification of E6AP $Lys^{847}$ modified by crosslinker 2. y-ions are highlighted. The full spectrum and b-ion identification can be found in Spectral Appendix I. E. Residue map of the E6AP C-terminus indicating sites of crosslinker modification by UbcH7 CΔS E93C-2/3 or UbcH7 CΔS E93C Ub-2/3.

FIGS. 14A-C. Purification of crosslinker-modified protein. (A.) Bands corresponding to the crosslinked UbcH7-E6AP complex or un-crosslinked UbcH7 or E6AP were excised (top), and then removed from gel matrix by electroelution into Tris-Glycine-SDS buffer. Silver staining of the recovered proteins (bottom). (B.) Following electroelution, the UbcH7-E6AP crosslinked complex was cleaved by acid hydrolysis to yield free UbcH7 and E6AP with unique modifications at crosslinked residues. (C.) Reaction mixtures that contained cleaved proteins were neutralized with aqueous sodium hydroxide, resolved with SDS-PAGE and then visualized with silver staining (top) or with western blotting (bottom). Both gels show that the crosslinked UbcH7-E6AP complex has been cleaved into free UbcH7 and E6AP. Cleaved proteins were recovered by acetone precipitation and then prepared for trypsin digestion and mass analysis (see Supplementary Methods below for all steps described in S10).

FIGS. 15A-B. $Lys^{847}$ of E6AP is required for the formation of $Lys^{48}$-linked polyubiquitin chains. A. WT UbcH7 (2 μM), E6AP HECT (indicated mutant, 2 μM), Uba1 (0.2 μM), Ub (200 μM) and ATP (2 mM) were incubated for 90 minutes in 25 mM HEPES pH 7.6, 100 mM NaCl, 4 mM $MgCl_2$ at room temperature before resolving with SDS-PAGE and analyzing the reaction mixtures with $Lys^{48}$-linkage specific antibody. B. UbcH7 CΔS E93C-1 (10 μM) and E6AP HECT (indicated mutant, 10 μM) were irradiated at 365 nm for 10 minutes and then resolved with reducing SDS-PAGE and analyzed with anti-UbcH7 antibody.

DEFINITIONS

Figure 1A:
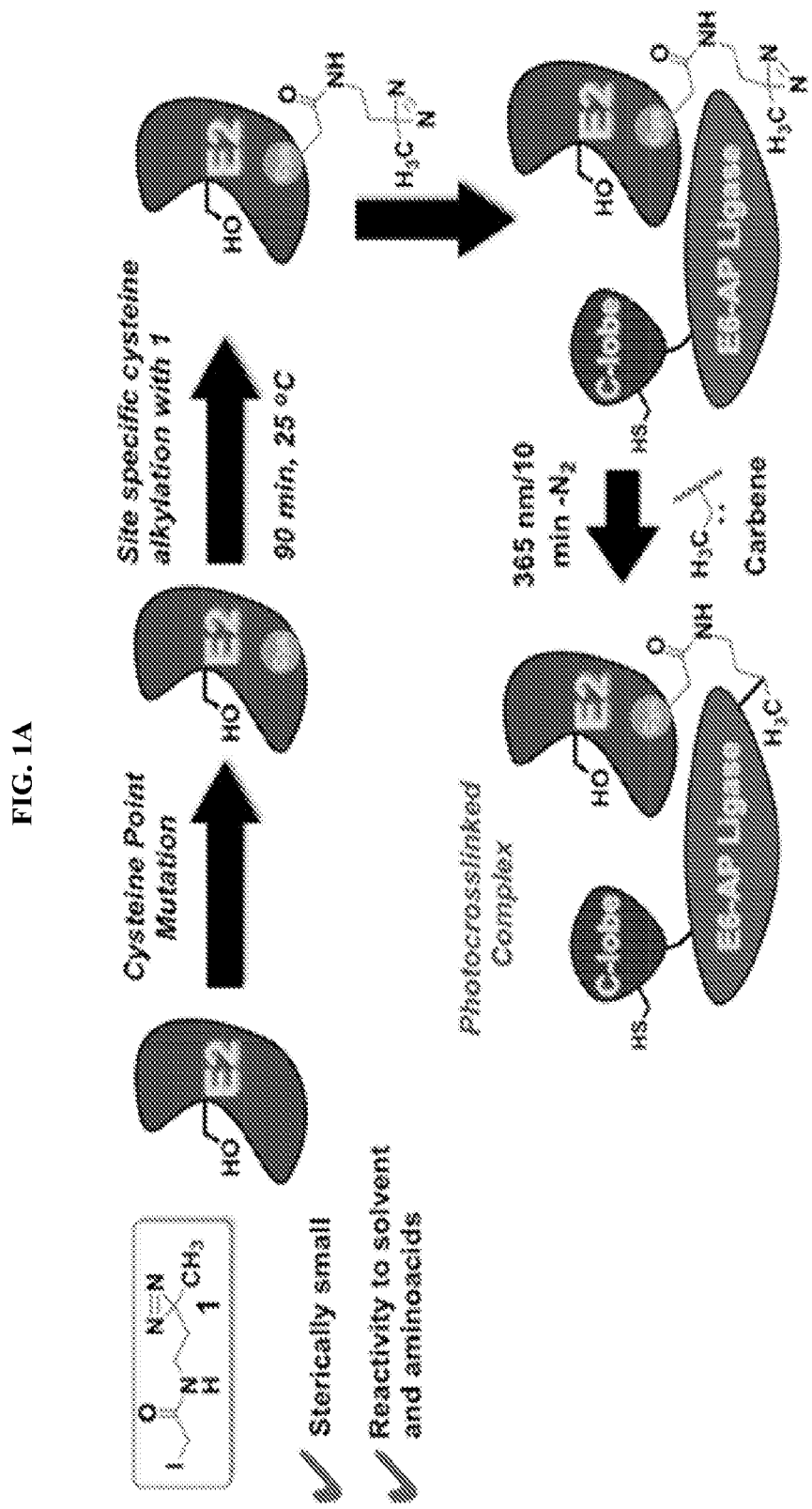
FIGS. 1A-C. Identification of residues at a protein-protein interface. A. The diazirine photocrosslinker 1 is site-specifically incorporated onto a protein surface to detect protein-protein interactions. B. Multiple UbcH7 cysteine mutants are equipped with 1, and then photocrosslinked to detect which UbcH7 surface(s) interacts with E6AP. C. Crosslinker 2 cleaves at low pH to allow clean detection of covalently modified residues by mass spectrometry (MS). D. Synthesis of deuterated crosslinker 3; allows MS validation of modified residues.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a photocrosslinking reagent" is a reference to one or more photocrosslinking reagents and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "photocrosslinking," and linguistic variants thereof, refers to the formation of a covalent linkage between protein residues that are adjacent in three dimensional spaces, in response to photo-irradiation. A "photocrosslinking reagent" is a compound that forms a covalent bond to one or more adjacent amino acids in response to photo-irradiation. A photocrosslinking reagent may be displayed on the surface of a protein or other biomolecule, or may be free in solution, upon initiation of photocrosslinking. Photocrosslinking may occur between three-dimensionally-adjacent sites on a single protein or between residues on separate proteins that are adjacent due to association of the two proteins. The covalent bond initiated by photo-irradiation may be specific for a particular residue (e.g., cysteine, lysine, arginine, etc.) or may be generic for any adjacent residue (e.g., as is the case for diazirine).

As used herein, the term "protein of interest" ("POI") refers to a protein that is selected for analysis by the compositions and/or methods herein. As used herein, the term "partner protein" refers to a protein that forms a complex or other association (e.g., stable or transient) with a protein of interest. A partner protein may be known or unknown prior to analysis with embodiments herein.

As used herein, the term "alkyl" refers to a hydrocarbon chain moiety consisting solely of carbon and hydrogen atoms, which is saturated or unsaturated (i.e., contains one or more double and/or triple bonds), having from one to twelve carbon atoms ($C_1$-$C_{12}$ alkyl). Alkyl includes alkenyls (one or more carbon-carbon double bonds) and alkynyls (one or more carbon-carbon triple bonds).

As used herein, the term "substituted," particularly when used in references to a chemical structure, refers to the presence of pendants, side chains, or functional groups appended to a core group. For example, a "substituted alkyl" refers to a hydrocarbon chain moiety consisting solely of carbon and hydrogen atoms, but having one or more additional function groups (e.g., other alkyls, OH, $NH_2$, halogen, =O, etc.) appended thereto.

As used herein, the term "heteroalkyl" refers to a hydrocarbon chain moiety having one or more of the main-chain carbons replaced by an O, N, or S. A heteroalkyl may be substituted in additional to the presence of backbone heteroatoms (e.g., a substituted heteroalkyl), and may be saturated (e.g., single bonds only) or may be an alkenyl or alkynyl.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

DETAILED DESCRIPTION

Provided herein are photocrosslinking reagents, crosslinkable proteins displaying photocrosslinking groups, crosslinked protein-protein complexes, and methods of use thereof.

In some embodiments, reagents are provided herein for protein crosslinking. Such reagents comprise first and second protein reactive moieties, connected either directly or via a suitable linker. In some embodiments, the first and second protein reactive moieties comprise functional groups that form covalent bonds with protein residues (e.g., specific amino acid side chains) under appropriate conditions.

In some embodiments, a first protein reactive moiety of a photocrosslinking reagent is chemically-reactive with (e.g., capable of forming a covalent bond with) one or more suitable protein side chains (e.g., arginine, lysis, cysteine, non-natural amino acid, etc.). In some embodiments, upon exposure of a protein of interested (POI) to the photocrosslinking reagent under suitable conditions (e.g., physiological conditions, neutral conditions, etc.), a covalent bond it formed between the first protein reactive moiety and one or more residues on the POI.

In some embodiments, a POI is engineered to display one or more residues (e.g., natural amino acids (e.g., cysteine), non-natural amino acids, etc.) for attachment of the photocrosslinking reagent via its first protein reactive moiety. In some embodiments, a POI that has been reacted with the protein reactive moiety of the photocrosslinking reagent displays the second protein reactive moiety of a photocrosslinking reagent on its surface.

In some embodiments, a second protein reactive moiety of a photocrosslinking reagent is photo-reactive with (e.g., capable of forming a covalent bond with, in the presence of photo-irradiation) one or more suitable protein side chains (e.g., arginine, lysis, cysteine, non-natural amino acids, etc.). In some embodiments, a second protein reactive moiety of a photocrosslinking reagent is non-specifically photo-reactive with any amino acid residues within proximity of the second protein reactive moiety. In some embodiments, upon contact of close proximity of a protein displaying an appropriate side chain to the second protein reactive moiety photocrosslinking reagent under suitable conditions (e.g., UV irradiation, etc.), a covalent bond it formed between the second protein reactive moiety and one or more residues.

In some embodiments, when a photocrosslinking reagent is covalently attached to a POI, to display the second (photo-reactive) protein reactive moiety on the surface of the protein, exposure of the POI and photocrosslinking reagent to phot-irradiation with result in crosslinking of the POI to any protein that presents an appropriate side chain in the proximity of the photocrosslinking reagent. In some embodiments, use of such photocrosslinking reagent allows the interactions of a POI (e.g., with known and unknown interaction partners) to be probed. In some embodiments, modification of residues within the POI (and/or within potential or known interaction partners) allows investigation of the sites of interaction between proteins.

In some embodiments, a photocrosslinking reagent is a compound comprising a chemically-reactive moiety and a photo-reactive moiety, either directly connected of connected by a linker.

In some embodiments, the chemically-reactive moiety is an iodoacetamide group. In some embodiments, iodoacetamide specifically reacts with the thiol group of cysteine residues. In some embodiments, the chemically-reactive moiety is used for attachment of the photocrosslinking reagent to a POI. In some embodiments, a POI is selected or engineered to present a single suitable position for attachment of the photocrosslinking reagent. In some embodiments, a POI is selected or engineered to present multiple suitable position for attachment of the iodoacetamide. When the chemically-reactive moiety is an iodoacetamide group, suitable attachment sites on the POI are surface exposed cysteines. In some embodiments, one or more existing cysteines are substituted for non-iodoacetamide reactive amino acids, to prevent attachment of the photocrosslinking reagent at such positions. In some embodiments, one or more existing non-cysteines are substituted for cysteine, to provide attachment of the photocrosslinking reagent at such positions. In some embodiments, multiple modified POIs are engineered to probe the surface of the POI for protein interactions In some embodiments, the photo-reactive moiety is a diazirine group. In some embodiments, diazirine non-specifically reacts with adjacent or proximal amino acids when exposed to UV irradiation. In some embodiments, the photo-reactive moiety is used for attachment of the photocrosslinking reagent (e.g., already attached to a POI) to a partner protein (e.g., a protein that forms a stable or transient complex or other association with the POI). In some embodiments, a partner protein is selected or engineered to present a single suitable position for attachment of the photocrosslinking reagent. In some embodiments, a partner protein is selected or engineered to present multiple suitable positions for attachment of the iodoacetamide. In some embodiments, an unmodified partner protein is used. When the photo-reactive moiety is an diazirine group, suitable attachment sites for attachment of the photocrosslinking reagent to the partner protein are surface exposed residues adjacent to the diazirine in three dimensional space. In some embodiments, unknown associations between the POI and partner proteins are identified using the reagents and methods herein. In some embodiments, known associations between the POI and partner proteins are analyzed using the reagents and methods herein.

In some embodiments, a photocrosslinking reagent comprises an iodoacetamide chemically reactive moiety (e.g., for attachment of the photocrosslinking reagent to a POI) and a diazirine photo-reactive moiety (e.g., for attachment of the photocrosslinking reagent to a partner protein). The iodoacetamide group may be directly attached to the diazirine group, or they may be connected by a linker group. In some embodiments, a photocrosslinking reagent comprises a compound of Formula I:

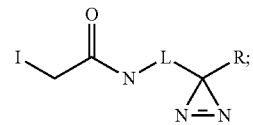

(Formula I)

wherein L is selected from a direct covalent bond, alkyl (e.g., methyl, ethyl, propyl, isopropyl, butyl, pentyl, hexyl, or larger), substituted alkyl (e.g., methyl, ethyl, propyl, isopropyl, butyl, pentyl, hexyl, or larger alkyl chain comprising one or more pendant substituents), heteroalkyl (e.g., methyl, ethyl, propyl, isopropyl, butyl, pentyl, hexyl, or larger alkyl chain comprising one or more C to N, S, or O substitutions), substituted heteroalkyl (e.g., methyl, ethyl, propyl, isopropyl, butyl, pentyl, hexyl, or larger alkyl chain comprising one or more one or more C to N, S, or O substitutions and one or more pendant substituents), and/or a cleavable moiety; and wherein R is selected from H, alkyl (e.g., methyl, ethyl, propyl, isopropyl, butyl, pentyl, hexyl, or larger), substituted alkyl (e.g., methyl, ethyl, propyl, isopropyl, butyl, pentyl, hexyl, or larger alkyl chain comprising one or more pendant substituents), heteroalkyl (e.g., methyl, ethyl, propyl, isopropyl, butyl, pentyl, hexyl, or larger alkyl chain comprising one or more C to N, S, or O substitutions), substituted heteroalkyl (e.g., methyl, ethyl, propyl, isopropyl, butyl, pentyl, hexyl, or larger alkyl chain comprising one or more one or more C to N, S, or O substitutions and one or more pendant substituents).

In some embodiments, any of the aforementioned alkyl groups (e.g., substituted, heteroalkyl, etc.) may be alkane-type, alkene-type, or alkyn-type chains.

In some embodiments, suitable substituents for substituted alkyl and substituted heteroalkyl are independently of any suitable chemical functional group, such as:
  single atoms: H, Cl, Br, F, or I;
  alkyl groups: methyl, ethyl, propyl, butyl, pentyl, hexyl, or any suitable straight chain or branched $C^1$-$C^{10}$ alkyl group;
  alkenyl: ethenyl, propenyl, butenyl, pentenyl, hexenyl, or any suitable $C^1$-$C^{10}$ alkenyl group;
  alkynyl: ethynyl, propynyl, butynyl, pentynyl, hexynyl, or any suitable $C^1$-$C^{10}$ alkenyl group;
  cycloalkyl: cyclopropyl, cyclobutyl, cyclopentyl, cyclohexyl, or any suitable $C^3$-$C^7$ cycloalkyl group; optionally further substituted;
  cycloalkenyl: cyclopropene, cyclobutene, cyclopentene, cyclohexene, cycloheptene, 1,3-cyclohexadiene, 1,4-cyclohexadiene, 1,5-cyclooctadiene; optionally further substituted;
  aryl or heteroaryl: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), thiadiazole, etc.; optionally further substituted;
  non-aromatic heterocyclic rings: aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, pepierazine, morpholine, thiomorpholine, dioxane, dithiane, trioxane, thithiane, azepane, oxepane, thiepane, homopiperazine, azocane, tetrahydropyran, etc.;
  haloalkanes: halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.), and branched haloalkanes;
  alcohols: OH, methanol, ethanol, propanol, butanol, pentanol, hexanol, cyclic alcohols (e.g., cyclohexanol), aromatic alcohols (e.g., phenol), or any other suitable combination of an OH moiety with a second moiety, branched alcohols;
  ketones: methyl methyl ketone (acetone), methyl ethyl ketone (butanone), propyl ethyl ketone (pentanone), or any other suitable combination of alkyl chains with =O;
  aldehydes: methanal, ethanal, propanal, butanal, pentanal, hexanal, or any other suitable combination of alkyl chain with =O;
  carboxylates: methanoate, ethanoate, propanote, butanoate, pentanoate, hexanoate, or any other suitable combination of alkyl chain with OO$^-$;
  carboxylic acids: methanoic acid, ethanoic acid, propanoic acid, butanoic acid, pentanoic acid, hexanoic acid, or any other suitable combination of alkyl chain with OOH;
  ethers: methoxy, ethoxy, methylmethoxy, ethylmethoxy, or any other suitable combination of alkyl chains surrounding an O;
  amides: methanamide ($CONH_2$), ethanamide ($CH_2CONH_2$), propanamide (($CH_2)_2CONH_2$), alkan″amide (($CH_2)_nCONH_2$), n-methyl alkan″amide (($CH_2)_nCONHCH_3$), c-methyl alkan″amide (($CH_2)_nNHCOCH_3$), n-alkyl alkan″amide (($CH_2)_nCONH(CH_2)_mCH_3$), c-methyl alkan″amide (($CH_2)_nNHCO(CH_2)_mCH_3$), etc.;
  primary amines: $NH_2$, methylamine, ethylamine, cyclopropylamine, etc.;
  secondary amines: aminomethyl ($NHCH_3$), aminoethyl ($NHCH_2CH_3$), methyl-aminomethyl ($CH_2NHCH_3$; aka methylamine-methane), alkyl″-aminomethane (($CH_2)_nNHCH_3$), etc.;
  tertiary amines: dimethylamine ($N(CH_3)_2$), dimethylamine ($N(CH_3)_2$), methyl-ethyl-amine ($NCH_3CH_2CH_3$), methane-diethylamine ($CH_2N(CH_2CH_3)_2$; aka methylamine-diethane), etc.;
  azides: methyl azide ($CH_2NNN$), ethyl azide (($CH_2)_2NNN$), alkyl″ azide (($CH_2)_nNNN$), etc.;
  cyanates: methyl cyanate ($CH_2OCN$), ethyl cyanate (($CH_2)_2OCN$), alkyl″ cyanate (($CH_2)_nOCN$), etc.;
  Cyanos: cyano (—CN), methyl carbonitrile ($CH_2CN$), ethyl carbonitrile (($CH_2)_2CN$), alkyl″ carbonitrile (($CH_2)_nCN$), etc.
  thiols: methanethiol ($CH_2SH$), ethanethiol (($CH_2)_2SH$), alkan″ethiol (($CH_2)_nSH$), etc.
  sulfides: dimethyl sulfide ($CH_2SCH_3$), methyl-ethyl sulfide ($CH_2SCH_2CH_3$), alkyl″-alkyl‴ sulfide (($CH_2)_nS(CH_2)_{m-1}CH_3$), etc.;
  sulfoxides: dimethyl sulfoxide ($CH_2SOCH_3$), methylethyl sulfoxide ($CH_2SOCH_2CH_3$), alkyl″-alkyl‴ sulfoxide (($CH_2)_nSO(CH_2)_{m-1}CH_3$), etc.;
  sulfone: dimethyl sulfone ($CH_2SO_2CH_3$; aka methylsulfone-methyl), methyl-ethyl sulfone ($CH_2SO_2CH_2CH_3$; aka methyl-sulfone-ethyl), alkyl″-alkyl‴ sulfone (($CH_2)_nSO_2(CH_2)_{m-1}CH_3$; aka alkyl″-sulfone-alkyl‴), $R^xSO_2R^y$ (wherein Rx and Ry are independently selected from any of the moieties provided in this list or combinations thereof), etc.;
  sulfuonamides: $SO_2NH_2$, methyl sulfonamide ($CH_2SO_2NH_2$), ethyl sulfonamide (($CH_2)_2SO_2NH_2$), alkyl″ sulfonamide (($CH_2)_nSO_2NH_2$), methyl methylsulfonamide ($CH_2SO_2NHCH_3$), alkyl″ alkyl‴sulfonamide (($CH_2)_nSO_2NH(CH_2)_mCH_3$, etc.;

sulfinic acids: SO₂H, methyl sulfinic acid (CH₂SO₂H), ethyl sulfinic acid ((CH₂)₂SO₂H), alkyl" sulfinic acid ((CH₂)ₙSO₂H), etc.;

thiocyanate: SCN, methyl thiocyanate (CH₂SCN), ethyl thiocyanate ((CH₂)₂SCN), alkyl" thiocyanate ((CH₂)ₙSCN), etc.;

phosphates: OP(=O)(OH)₂, methyl phosphate (CH₂OP(=O)(OH)₂), ethyl phosphate ((CH₂)₂OP(=O)(OH)₂), alkyl" phosphate ((CH₂)ₙOP(=O)(OH)₂), etc.; and suitable combinations thereof. For example, in some embodiments, substituents (when present) are independently selected from: H, alkyl group (e.g., straight-chain alkyl (e.g., methyl, ethyl, propyl, butyl, pentyl, hexyl, etc.), branched alkyl group (e.g., iso-propyl, 2-methyl-hexyl, 3-methyl, 2-propyl-octyl, etc.), cycloalkyl (e.g., cyclopropyl, cyclobutyl, cyclopentyl, cyclohexyl, cycloheptyl, cyclooctyl, etc.), branched cyclic alkyl (e.g., methylcyclohexyl, ethylcyclobutyl, propylcyclohexyl, etc.)), a substituted alkyl group (e.g., halogen-substituted alkyl group (e.g., trihalobuthane (e.g. trifluorobuthane), dihalobuthane (e.g. difluorobuthane), monohalobuthane (e.g. monofluorobuthane), trihalopropane (e.g. trifluoropropane), dihalopropane (e.g. difluoropropane), monohalopropane (monofluoropropane), trihaloethane (e.g., trifluoroethane), dihaloethane (e.g. difluroethane), haloethane (e.g. fluoroethane), halomethane (e.g., fluoromethane), dihalomethane (e.g., difluoromethane), trihalomethane (e.g., trifluoromethane), etc.), alkene (e.g., CH=CH₂, CH₂CH=CH₂, CH=CHCH₃, etc.), alkyne (e.g., C≡CH, C≡CCH₃, CH₂C≡CH, etc.), alkoxy group (e.g., hydroxyl (e.g., (CH2)₀₋₆OH, ether ((CH2)₀₋₆O(CH2)₀₋₆)), amine (e.g., NH₂), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. CH₂CN), —SO₂CH₃ group, —SO₂NH₂ group, sulfonyl group, dialkylphosphine oxide (e.g., —PO(CH₃)₂), a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a carbocyclic (substituted or non-substituted), aryl carbocyclic (substituted or non-substituted), heteroaryl carbocyclic (substituted or non-substituted), and/or combinations thereof.

In some embodiments, R is a methyl group, and a photocrosslinking reagent comprises a compound of Formula II:

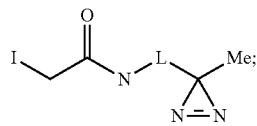

(Formula II)

wherein L is selected from a direct covalent bond, alkyl, substituted alkyl, heteroalkyl, substituted heteroalkyl, and/or a cleavable moiety.

In some embodiments, R is a methyl group and L is a ethyl group, and a photocrosslinking reagent comprises a compound of Formula III:

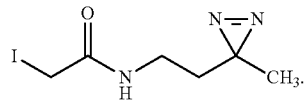

(Formula III)

In some embodiments, L of, for example, Formula I or Formula II comprises a cleavable moiety. In some embodiments, the cleavable moiety is photocleavable, chemically cleavable, pH cleavable (e.g., acid labile, base labile, etc.), or enzymatically cleavable (e.g. protease recognition sequence). In some embodiments, the cleavable moiety is N-acylsulfamate (e.g., an acid-labile linker). In such embodiments, a photocrosslinking reagent may comprise a compound of Formula IV:

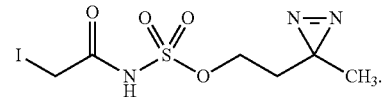

(Formula IV)

In some embodiments, a photocrosslinking reagent is isotopically-labelled at one or more positions. In general, isotopically-labeled compounds are identical to those recited in the various formulae, structures, and descriptions herein, but for the fact that one or more atoms are replaced by an atom having an atomic mass or mass number different from the atomic mass or mass number most common in nature. Examples of isotopes that can be incorporated into the present compounds include isotopes of hydrogen, carbon, nitrogen, oxygen, fluorine and chlorine, for example, ²H, ³H, ¹³C, ¹⁴C, ¹⁵N, ¹⁸O, ¹⁷O, ³⁵S, ¹⁸F, ³⁶Cl, respectively. Certain isotopically-labeled compounds described herein, for example those into which radioactive isotopes such as ³H and ¹⁴C are incorporated, are useful in drug and/or substrate tissue distribution assays. In some embodiments, substitution with isotopes such as deuterium, i.e., ²H, affords advantages in detecting photocrosslinking reagent following attachment to the protein, and facilitates identification of the site of attachment. In some embodiments, a photocrosslinking reagent is isotopically-labelled at one or more positions with a non-natural abundance of stable heavy isotopes. In some embodiments, one or more hydrogen positions of a photocrosslinking reagent described herein is replaced with deuterium. In some embodiments, a photocrosslinking reagent may comprise a compound of Formula V:

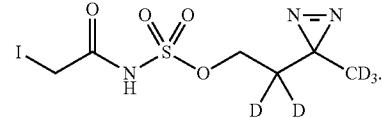

(Formula IV)

In some embodiments, photocrosslinking reagents are small molecules and are designed/intended not to interfere with the protein-protein interactions they are intended to detect. In some embodiments, photocrosslinking reagents lack bulky groups and/or rigid functional groups that create steric hindrance to protein-protein interactions. In some embodiments, photocrosslinking reagents have molecular weights of <5000 g/mol, <2000 g/mol, <1000 g/mol, <750 g/mol, <500 g/mol, etc.

In some embodiments, photocrosslinking reagents comprise a tag or handle to facilitate separation of proteins attached to the photocrosslinking reagent from unattached proteins or contaminants. A suitable tag or handle is any functional group that can be stably targets (e.g., non-covalently) to separate the photocrosslinking reagent and bound proteins from materials not associated with the photocrosslinking reagent. An exemplary moiety for this purpose is biotin.

In some embodiments, photocrosslinking reagents are provided that allow for the crosslinking or two or more protein species that associate in vivo and/or in vitro. In some embodiments, once crosslinked, methods are provided herein for the analysis of the crosslinked proteins, identification of unknown partner proteins, identification of the sites, domains, or regions of proteins that interact, etc. In some embodiments, analysis of the crosslinked proteins is performed using any suitable techniques for the purification, isolation, manipulation, fragmentation, detection, characterization, identification of proteins.

In some embodiments, crosslinked proteins are isolated/purified from non-crosslinked proteins and other contaminants by any suitable techniques including column purification, gel electrophoresis (e.g., SDS-PAGE), gradient purification, filter purification, etc. In some embodiments in which crosslinked proteins are purified by gel electrophoresis, the bands identified on the gel (e.g., corresponding to the crosslinked proteins) are removed from the gel (e.g., from an excised band) by electroelution (e.g., denaturing electroelution, as described in the Examples herein). In some embodiments, isolated/purified crosslinked proteins are further purified and/or concentrated by precipitation and resuspension. Any other suitable protein processing and/or purification techniques known in the field may also find use in embodiments herein.

In some embodiments, crosslinked proteins are separated from each other by cleavage of the linker. In some embodiments, cleavage is performed after the crosslinked proteins are purified away from un-crosslinked proteins and/or contaminants. In some embodiments, a cleavalge linker (e.g., photocleavable, pH-cleavable (e.g., base labile, acid labile, etc.), enzyme-cleavable, chemically-cleavable, etc.) allows for separation of the crosslinked proteins under the desired conditions. In some embodiments, cleavage of the linker leaves a portion of the photocrosslinking reagent attached to one or both of the formerly crosslinked proteins. In some embodiments, the remnant of the reagent serves as a tag (e.g., isotopically-labelled tag) for downstream analysis of the protein(s). In some embodiments, the protein(s) is analyzed to determine the identity of the protein(s) and/or the location/identity of the crosslinked amino acid residue.

In some embodiments, one or both of the crosslinked proteins (e.g., after purification steps, after cleavage of the crosslinked proteins, etc.) are subjected to fragmentation to produce peptide fragments to facilitate analysis. Suitable methods for protein fragmentation are known in the field and include trypsinization. In some embodiments, fragments of a protein (e.g., POI, partner protein, etc.) are analyzed to identify an unknown protein and/or to determine identity/position of the crosslinked amino acid.

In some embodiments, analysis of crosslinked proteins (e.g., POI, partner protein, etc.) and/or fragments thereof is performed by any suitable biophysical and/or biochemical techniques. In particular embodiments, mass spectrometry is utilized for the analyses described herein. "Mass spectrometry" ("MS") encompasses any spectrometric technique or process in which molecules are ionized and separated and/or analyzed based on their respective molecular weights. Thus, as used herein, "mass spectrometry" encompass any type of ionization method, including without limitation electrospray ionization (ESI), atmospheric-pressure chemical ionization (APCI) and other forms of atmospheric pressure ionization (API), and laser irradiation. Mass spectrometers are commonly combined with separation methods such as gas chromatography (GC) and liquid chromatography (LC). The GC or LC separates the components in a mixture, and the components are then individually introduced into the mass spectrometer; such techniques are generally called GC/MS and LC/MS, respectively. MS/MS is an analogous technique where the first-stage separation device is another mass spectrometer. In LC/MS/MS, the separation methods comprise liquid chromatography and MS. Any combination (e.g., GC/MS/MS, GC/LC/MS, GC/LC/MS/MS, etc.) of methods can be used to practice the invention. In such combinations, "MS" can refer to any form of mass spectrtometry; by way of non-limiting example, "LC/MS" encompasses LC/ESI MS and LC/MALDI-TOF MS. Also included herein, without limitation, are APCI MS; ESI MS; GC MS; MALDI-TOF MS; LC/MS combinations; LC/MS/MS combinations; MS/MS combinations; etc.

Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. Less than femtomole quantities of material can be readily analyzed by MS to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ESI), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In some embodiments, samples are subjected to one or more forms of liquid chromatography (LC), including without limitation high-performance liquid chromatography (HPLC) and reverse-phase high-performance liquid chromatography (RP-HPLC), prior to and/or in conjunction with MS analysis.

HPLC is a separative and quantitative analytical tool that is generally robust, reliable and flexible. Reverse-phase (RP)

is a commonly used stationary phase that is characterized by alkyl chains of specific length immobilized to a silica bead support. RP-HPLC is suitable for the separation and analysis of various types of compounds. One of the most important reasons that RP-HPLC has been the technique of choice amongst all HPLC techniques is its compatibility with electrospray ionization (ESI). During ESI, liquid samples are introduced into a mass spectrometer by a process that creates multiple charged ions (Wilm et al., Anal. Chem. 68:1, 1996).

In some embodiments, MS analysis of a sample(s) and/or controls results in a mass spectrum and/or mass spectra (a plot of intensity vs. m/z (mass-to-charge ratio) of a chemical analysis). In some embodiments, methods are provided herein for the analysis of mass spectra to identify unique molecular species (e.g., peptide fragment) within a sample.

EXPERIMENTAL

Example 1

Chemical Synthesis

General

Methanol (ACS grade), ethyl acetate (ACS grade), hexane (ACS grade), acetonitrile (ACS grade), chloroform (ACS grade) and diethyl ether (ACS grade) were purchased from Fisher Scientific and used without further purification. Dichloromethane and dimethylformamide were purified by passing over activated alumina. Commercially available reagents were used without further purification. Reactions were monitored by thin-layer chromatography (TLC) on pre-coated glassbacked plates (60 Å silica gel, 0.25 mm, Whatman), and components were visualized by UV light (254 and 365 nm) or by treating the plates with p-anisaldehyde, KMnO4, and ninhydrin stains followed by heating. Flash column chromatography was performed over ultra pure silica gel (230-400 mesh) from Silicycle. 1 H and 13C NMR spectra were obtained on Bruker AVANCE III 500 MHz spectrometers. Chemical shifts were reported in ppm relative to the residual solvent peak (CDCl3, 13C 77.00; TMS: 0.00). Multiplicity was indicated as follows: s (singlet); d (doublet); t (triplet); q (quartet); m (multiplet); dd (doublet of doublets); ddd (doublet of doublet of doublets); dt (doublets of triplets); td (triplet of doublets); brs (broad singlet). Coupling constants were reported in Hz

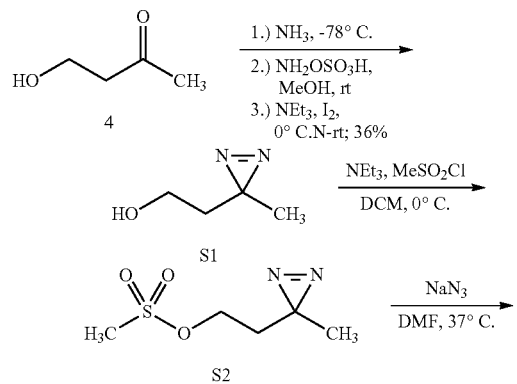

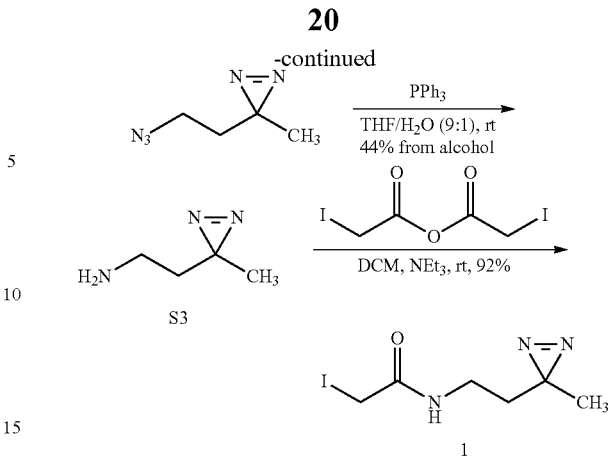

Synthesis of Compound S1

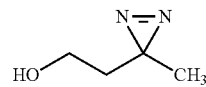

4-hydroxy-2-butanone 4 (32.2 g, 365 mmol) was degassed with $N_{2(g)}$ and then added dropwise over 6 min to a stirring solution of $NH_{3(l)}$ (~180 mL, 8.6 mol) in an $N_{2(g)}$-purged 1 L, 3-neck round-bottomed flask maintained at −78° C. in an acetone/$CO_{2(s)}$ bath. After stirring for 5 h at −78° C., hydroxylamine O-sulfonic acid (45.7 g, 402 mmol) was dissolved in methanol (300 mL), degassed, and added by cannula to the reaction over 70 minutes. The reaction was then warmed to room temperature overnight with constant stirring. After filtering off the resulting white precipitate, the filtrate was concentrated to ~300 mL. The filtrate was diluted with methanol (300 mL added) and cooled to 0° C. with stirring. Triethylamine (45 mL, 323 mmol) was added, and then iodine flakes (52.9 g, 208 mmol) until the brown solution color persisted. The ice bath was removed so that the solution warmed to room temperature over 2 h with constant stirring. The solution was concentrated to 300 mL, washed with brine (600 mL), extracted with diethyl ether (3×100 mL), dried ($Na_2SO_4$), and then concentrated to <10 mL of a dark red solution. Vacuum distillation (61° C., 2 torr) provided S1 (13.23 g, 365 mmol, 36% yield) as a pale yellow oil. $^1$H NMR (500 MHz, Chloroform-d) δ 3.51 (q, J=6.1 Hz, 2H), 2.01-1.81 (m, 1H), 1.61 (t, J=6.3 Hz, 2H), 1.05 (s, 3H). $^{13}$C NMR (126 MHz, CDCl$_3$) δ 57.77, 37.01, 24.38, 20.33.

Synthesis of Compound S2

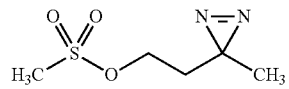

To a 500 mL, 3-neck round-bottomed flask purged with $N_{2(g)}$ was added diazirine S1 (5.9 g, 58.9 mmol) in methylene chloride (300 mL). After cooling the solution to 0° C., triethylamine (9.5 mL, 68.2 mmol) and methanesulfonyl chloride (5.5 mL, 71.1 mmol) were added and stirred for 2 h at 0° C. The reaction was then quenched with a saturated aqueous solution of ammonium chloride (200 mL). The resulting aqueous layer was extracted with methylene chloride (3×100 mL). The combined organic layers were dried (Na$_2$SO$_4$), filtered, concentrated, filtered through a silica gel plug (hexanes:ethyl acetate 2:1), and then concentrated to obtain the S2 mesylate as a yellow oil (12.34 g, used without further purification). $^1$H NMR (500 MHz, Chloroform-d) δ 4.13 (t, J=6.2 Hz, 2H), 3.06 (s, 3H), 1.80 (t, J=6.3 Hz, 2H), 1.10 (s, 3H). $^{13}$C NMR (126 MHz, Chloroform-d) δ 64.52, 37.75, 34.35, 23.61, 20.05.

Synthesis of Compound S3

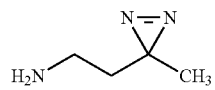

To a 250 mL, 3-neck round bottomed flask purged with N$_{2(g)}$ was added Compound S2 with dimethylformamide (50 mL). Sodium azide (15.3 g, 235 mmol) was added and the reaction then stirred at 37° C. for 9 h. The resulting solution was diluted with water (250 mL) and Et$_2$O (100 mL), and mixed vigorously for 10 min. The resulting aqueous layer was extracted with Et$_2$O (2×100 mL). The combined organic layers were washed with water (2×100 mL), dried (MgSO$_4$), and concentrated to 16.2 g (~20% diazirine azide in Et$_2$O by $^1$HNMR; to avoid extensive evaporation of the volatile diazirine azide, all Et$_2$O was not removed by rotovap). This mixture was added to a solution of THF/H$_2$O (9:1, 250 mL) in a 500 mL, 3-neck round-bottomed flask and stirred with triphenylphospine (31.16 g, 118.8 mmol) overnight at room temperature under N$_{2(g)}$. The crude reaction solution was then extracted with aqueous 1 M HCl (3×80 mL) with vigorous stirring in a 1 L round-bottomed flask. The resulting aqueous layer was washed with Et$_2$O (6×100 mL), and then neutralized with NaOH (5 M, 50 mL). The resulting aqueous was extracted with Et$_2$O (first crop: 5×100 mL; second crop: 2×250 mL). The combined organics were dried (MgSO$_4$), filtered, and concentrated to obtain the S3 amine as a clear liquid (3.77 g, ~68% pure by $^1$HNMR, 44% yield from alcohol S1). The S3 amine appeared volatile on rotovap and so was used without removing all Et$_2$O.

$^1$H NMR (500 MHz, Chloroform-d) δ 2.55 (tt, J=7.1, 3.4 Hz, 2H), 1.52 (tt, J=6.9, 3.2 Hz, 2H), 1.32-1.10 (m, 2H), 1.08-0.80 (m, 3H). $^{13}$C NMR (126 MHz, Chloroform-d) δ 37.76, 36.97, 24.59, 20.14.

Synthesis of Crosslinker 1

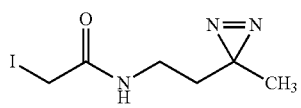

To a 10 mL round-bottomed flask under N$_{2(g)}$ was added Compound S3 (0.033 g, 68% pure in Et$_2$O, 0.23 mmol), methylene chloride (3.8 mL), and iodoacetic anhydride (0.15 g, 0.42 mmol). Triethylamine (0.6 mL, 0.43 mmol) was then added dropwise. After 90 min at room temperature, the solution was washed with a saturated aqueous solution of NaHCO$_3$ (2×2 mL), brine (3 mL), dried (Na$_2$SO$_4$), concentrated, and purified with flash chromatography (SiO$_2$, hexanes/ethyl acetate 2:1) to obtain crosslinker 1 (0.056 g, 0.21 mmol, 92.6% yield) as a waxy yellow solid.

$^1$H NMR (500 MHz, Chloroform-d) δ 6.19 (s, 1H), 3.71 (s, 2H), 3.46-2.83 (m, 2H), 1.62 (t, J=6.8 Hz, 2H), 1.06 (s, 3H). $^{13}$C NMR (126 MHz, CDCl$_3$) δ 167.15, 35.74, 33.83, 24.43, 20.00, −0.61.

Scheme S2. Synthesis of crosslinker 2

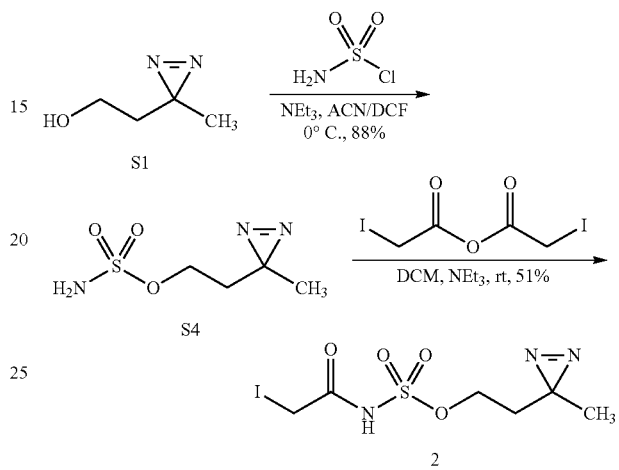

Synthesis of Sulfamoyl Chloride

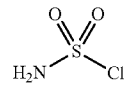

To a 100 mL round-bottomed flask at 0° C. under N$_{2(g)}$ was added chlorosulfonyl isocyanate (4.39 g, 16.89 mmol) and then formic acid (1.23 mL, 32.6 mmol) dropwise over 5 minutes with constant stirring. After 30 minutes, acetonitrile (30 mL) was added to dissolve the precipitate. A strong N$_{2(g)}$ stream was passed over the stirring solution opened to the atmosphere. This purge was continued overnight to produce a white solid that was then used without further purification for the synthesis of Compound S4.

Synthesis of Compound S4

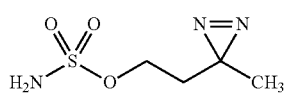

To a 50 mL round-bottomed flask at 0° C. under N$_{2(g)}$ was added Compound S1 (0.35 g, 3.50 mmol), dimethylformamide (5 mL), and a solution of sulfamoyl chloride in acetonitrile (10 mL). After stirring the solution for several minutes, triethylamine (0.73 mL, 5.23 mmol) was then added dropwise. The solution was warmed to room temperate over 2 h under vigorous stirring and the resulting precipitate was filtered and washed with acetonitrile (3×10 mL). The combined organics were concentrated and then dried to a paste overnight under high vacuum. This solid was dissolved in distilled water (150 mL) and extracted with ethyl acetate (5×100 mL). The combined organics were washed with brine (300 mL), dried (MgSO₄), concentrated, and purified with flash chromatography (SiO₂, chloroform/methanol 20:1) to provide Compound S4 as a clear liquid (0.551 g, 3.1 mmol, 88% yield). ¹H NMR (500 MHz, Chloroform-d) δ 4.85 (s, 2H), 4.13 (t, J=6.3 Hz, 2H), 1.80 (t, J=6.3 Hz, 2H), 1.11 (s, 3H). ¹³C NMR (126 MHz, CDCl₃) δ 66.13, 34.03, 23.77, 20.06.

Synthesis of Crosslinker 2

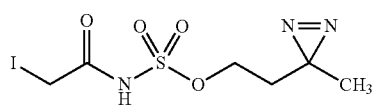

To a 25 mL round-bottomed flask under $N_{2(g)}$ at 0° C. was added Compound S4 (0.0503 g, 0.28 mmol), methylene chloride (6 mL) and iodoacetic anhydride (0.268 g, 0.76 mmol). After stirring the solution for several minutes, N,N-diisopropylethylamine (0.14 mL, 0.80 mmol) was added dropwise and the reaction stirred for an additional 30 minutes. The reaction solution was then washed with cold (4° C.) aqueous 0.3 M HCl (2×15 mL), brine (15 mL), dried (Na₂SO₄), filtered, and concentrated. The residue was purified with flash chromatography (SiO₂, ethyl acetate/hexanes gradient: 17% EtOAc to 100% EtOAc) to provide Crosslinker 2 as a waxy solid (0.050 g, 0.14 mmol, 51% yield). Note: A minimal amount of silica gel was used to avoid compound decomposition. Fractions from the silica column were analyzed with TLC (100% EtOAc mobile phase) to observe separation of product from a contaminant that remained at the TLC baseline. ¹H NMR (500 MHz, Chloroform-d) δ 4.34 (t, J=6.3 Hz, 2H), 3.84 (s, 2H), 1.82 (t, J=6.3 Hz, 2H), 1.11 (s, 3H).
¹H NMR (500 MHz, DMSO-d₆) δ 4.08 (t, J=6.2 Hz, 2H), 3.67 (s, 2H), 1.68 (t, J=6.2 Hz, 2H), 1.03 (s, 3H). ¹³C NMR (126 MHz, CDCl₃) δ 166.27, 69.58, 34.25, 23.60, 20.00, −3.35. ¹³C NMR (126 MHz, DMSO) δ 168.49, 66.38, 33.49, 24.10, 19.22, 2.15. MS calcd for C₆H₁₀IN₃O₄S: 346.94; Found: m/z 346.07.

Scheme S3. Synthesis of crosslinker 3

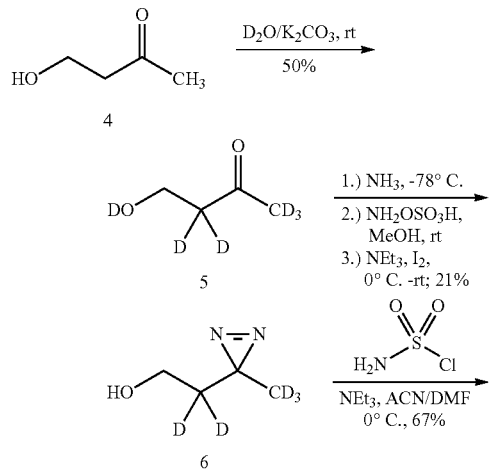

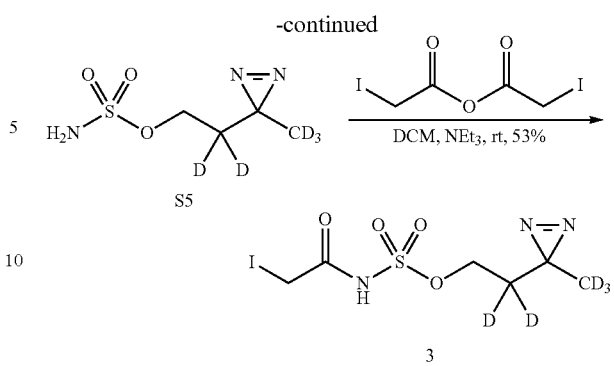

Synthesis of Compound 5

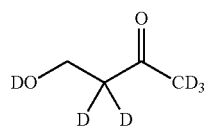

To a 250 mL round-bottomed flask was added potassium carbonate (1.4 g, 10.13 mmol), D₂O (125 mL), and 4-hydroxy-2-butanone 4 (12.5 g, 142.0 mmol). After stirring vigorously for 12 hours at room temperature, the solution changed from cloudy to clear yellow. It was extracted with methylene chloride (6×100 mL), dried (Na₂SO₄), filtered, and concentrated to produce Compound 5. Since Compound 5 appeared volatile on rotovap, we used it without removing all methylene chloride (62.5% 5 in methylene chloride, 10.75 g, 71.37 mmol, 50.3% yield, >95% deuterated by ¹HNMR). ¹H NMR (500 MHz, Chloroform-d) δ 3.77 (s, 2H). ¹³C NMR (126 MHz, Chloroform-d) δ 209.83 (d, J=6.4 Hz), 57.45, 47.05-43.16 (m), 31.49-28.72 (m).

Synthesis of Compound 6

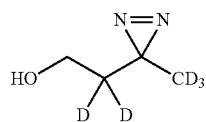 [SMILES: [2H]C([2H])([2H])C1(C([2H])([2H])CO)N=N1]

Compound 5 (7.05 g, 62.5% in methylene chloride, 46.81 mmol) was treated to the conditions used to synthesize Compound S1 (with reagent amounts scaled down) to give Compound 6 as a clear, yellow oil (1.009 g, 9.59 mmol 20.5% yield, 94% deuteration by ¹HNMR). ¹H NMR (500 MHz, Chloroform-d) δ 3.51 (s, 2H), 1.82 (s, 1H). ¹³C NMR (126 MHz, Chloroform-d) δ 57.70, 40.49-32.97 (m), 24.15, 21.22-17.34 (m).

Synthesis of Compound S5

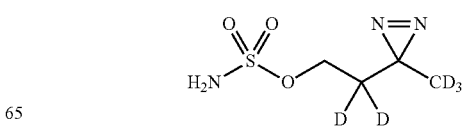

Compound 6 (0.31 g, 2.97 mmol) was treated to conditions used to synthesize Compound S4 (with reagent amounts scaled down) to give Compound S5 as a clear liquid (0.36 g, 1.97 mmol, 66.9% yield, >94% deuteration by $^1$HNMR). $^1$H NMR (500 MHz, Chloroform-d) δ 4.90 (s, 2H), 4.12 (s, 2H).

Synthesis of crosslinker 3

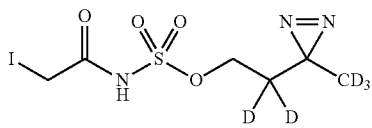 [SMILES: [2H]C([2H])([2H])C1(C([2H])([2H])COS(=O)(=O)NC(=O)CI)N=N1]

Compound S5 (0.11 g, 0.60 mmol) was treated to conditions used to synthesize Crosslinker 2 (with reagent amounts scaled down) to give Crosslinker 3 as a waxy solid (0.11 g, 0.31 mmol, 52.8% yield, >94% deuteration by $^1$HNMR). $^1$H NMR (500 MHz, Chloroform-d) δ 4.32 (s, 2H), 3.85 (s, 2H).

Example 2

Biochemical Procedures

Materials

Reagents for buffers, Triton X-100, IPTG, DTT, TCEP, and glutathione agarose beads were purchased from Fisher Scientific and were used as received unless otherwise noted. Deoxyribonuclease I from bovine pancrease and thrombin were purchase from Sigma-Aldrich. *E. Coli* for protein expression was purchased from Millipore. Protein concentrations were assessed by BioSpec nano (Shimadzu) or Bradford assay (Bio-Rad). Proteins on polyacrylamide gels were visualized with InstantBlue (Expedeon) staining solution. Antibodies against UbcH7 (UBE2L3, #8721) and Lys[48]-linkage specific polyubiquitin (#8081) were purchased from Cell Signaling. Mutagenesis was performed with QuickChange mutagenesis (Agilent Technologies). Intact protein mass spectrometry was performed on the Agilent 6210A LC-TOF.

Buffers

PBS(A): 137 mM NaCl, 2.7 mM KCl, 10 mM $Na_2HPO_4$, 1.8 mM $KH_2PO_4$

PBS(B): 137 mM NaCl, 2.7 mM KCl, 10 mM $Na_2HPO_4$

Tris-Glycine-SDS: 25 mM Tris base, 192 mM glycine, 3.5 mM SDS

Protein Expression

E6AP-HECT

GST-E6AP-HECT domain (481-852) cloned into the pGEX-4T-1 vector was transformed into *E. coli* Rosetta (DE3) pLysS cells. E6AP was induced with 300 μM IPTG at 18° C. for 20 h ($OD_{600}$ 3.0, 1 L terrific broth). Cell pellets were resuspended in PBS(A) with DTT (1 mM), $MgCl_2$ (10 mM), protease inhibitor (Roche COMPLETE), and DNAse I from bovine pancreas (Sigma Aldrich, 10 μg/mL final concentration). Following sonication, cell lysate was incubated with Triton X-100 (0.2% final concentration) for 30 min, rocking at 4° C., and then cleared by centrifugation at 18,500 rpm for 40 min at 4° C. The supernatant was passed through a 0.45 μm syringe and then incubated with glutathione agarose bead slurry (Pierce, 1.5 mL bead slurry per 1 L culture) that had been equilibrated with PBS(A) containing DTT (1 mM). After incubating with the cell lysate at 4° C. for 12 h, the GST-beads were washed with 50 mM Tris, 150 mM NaCl, 1 mM DTT pH 8.5 (4×15 ml). E6AP HECT domain was cleaved from the beads by incubating with thrombin (20 units, Sigma Aldrich) in 1.5 mL 50 mM Tris, 150 mM NaCl, 1 mM DTT pH 8.5 for 12 h at room temperature on a rocker. E6AP was eluted with 50 mM Tris, 150 mM NaCl, 1 mM DTT, 1 mM PMSF pH 8.5, concentrated to 100 μM and stored at −80° C.

UbcH7

GST-UbcH7 mutants cloned into the pGEX-6P vector were transformed into *E. Coli* BL21 cells. UbcH7 was induced with 300 μM IPTG at 18° C. for 20 h ($OD_{600}$ 3.0, 1 L terrific broth). Cell pellets were resuspended in PBS(A) with DTT (1 mM), $MgCl_2$ (10 mM), protease inhibitor (Roche COMPLETE), and DNAse I from bovine pancreas (Sigma Aldrich, 10 μg/mL final concentration). Following sonication, lysate was cleared by centrifugation at 18,500 rpm for 40 min at 4° C. The supernatant was passed through a 0.45 μm syringe filtered, and then added to glutathione agarose bead slurry (Pierce, 1.5 ml bead slurry per 1 L culture) that had been equilibrated with PBS(A) with DTT (1 mM). After rocking at 4° C. for 12 h with lysate, the beads were washed with PBS(A) with DTT (1 mM) (3×15 ml). UbcH7 was then cleaved from the beads by incubating with PreScission Protease (1 mg, GE Heathcare) in 1.5 mL PBS(A) with DTT (1 mM) for 12 h at 4° C. on a rocker. Protein was then eluted with PBS(A) with DTT (1 mM), concentrated to 150 μM and stored at −80° C.

UbcH7 CΔS-Ub Oxyester Synthesis

A solution of UbcH7 C17S C86S C117S (CΔS) (200 μM), mouse Uba1 (13 μM), ubiquitin from bovine erythrocytes (900 μM), and ATP (5 mM) in reaction buffer (25 mM HEPES pH 7.5, 50 mM NaCl, 10 mM $MgCl_2$, 1 mM DTT) was shaken at 30° C., 45 rpm for 6 hours. The resulting UbcH7-Ub oxyester conjugate was purified on Superdex 75 size exclusion resin equilibrated with 25 mM HEPES pH 7.0, 50 mM NaCl, 1 mM DTT, concentrated to 100 μM and stored at −80° C.

Protein Alkylation

Crosslinker in DMF (500 mM, 5 mM final concentration) was added to a UbcH7 cysteine mutant (100-200 μM in UbcH7 storage buffer; 1% DMF v/v final concentration). The resulting reaction mixture was mixed by pipetting, covered with aluminum foil, and rocked at room temperature (crosslinkers 1), or 4° C. (crosslinker 2 and 3) for 90 minutes. Immediately following, the solution was desalted/exchanged into PBS(B) with a Zeba Spin Desalting Column (7 kDa MWCO Pierce), frozen in $N_{2(l)}$, and stored at −80° C. The extent of alklylation was analyzed by LC-MS.

Photocrosslinking Assay for Mass Spectrometry Analysis

E6AP HECT was exchanged into crosslinker buffer with Zeba Spin Desalting Column and mixed (14 μM final concentration, 480 μg) with Tween-20 (6 μM), DTT (1 mM) in PBS(B) in a 1.5 mL tube. The reaction mixture was then taken to a darkened room where alkylated UbcH7 (14 μM, final concentration, 203 μg) was added (final volume of reaction mixture was 790 μL). The solution was mixed by pipetting and then transferred to four wells of a 96 well plate (Costar #3370). The plate was placed 3 cm below a UV lamp (UVP 3UV-38 3UV Lamp; 8 watt, 115V ~60 Hz, 0.16 Amps) and irradiated at 365 nm for 10 minutes.

Figure 2C:
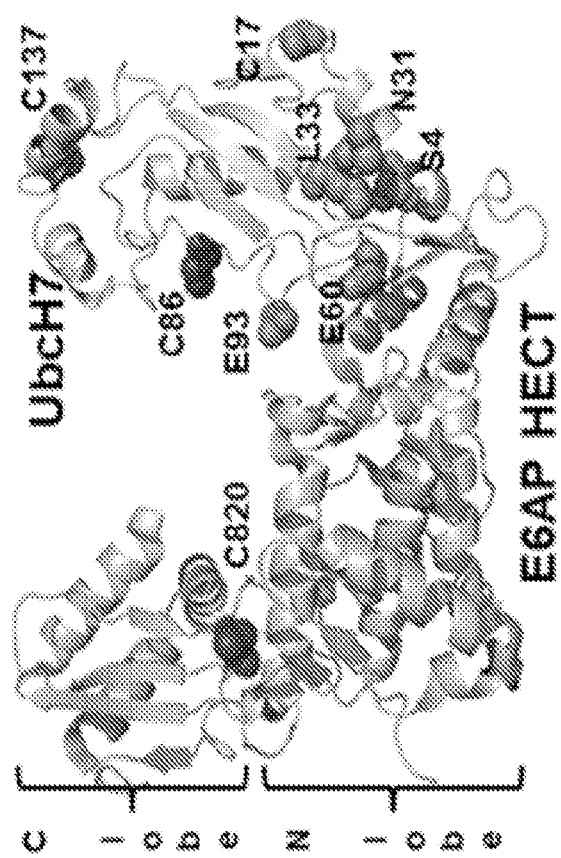
FIGS. 2AC. Cysteine scan identifies UbcH7 residues for robust crosslinking of E6AP. A. Eleven UbcH7 C17S C86S C137S (CΔS) mutants were expressed and equipped with 1 at the indicated residues (PDB: 1C4Z). B. Different UbcH7 CΔS-1 mutants (10 µM) and E6AP HECT (10 µM) were irradiated at 365 nm for 10 minutes and resolved with reducing SDS-PAGE. C. Triplicate reactions as in (B) were analyzed by western blot and quantitated with ImageJ to estimate relative crosslinking efficiency when 1 was placed at the indicated UbcH7 CΔS residue. "*" indicates that crosslinker is on an UbcH7 CΔS-Ub oxyester.

Following irradiation, the sample was mixed with Laemmli buffer and β-mercaptoethanol (230 mM final concentration) and boiled for five minutes. Crosslinking experiments in main text FIGS. 2, 3, and 4 were performed similarly with 20-50 μL total volume and with the indicated final concentrations of UbcH7 and E6AP.

Isolation of Photocrosslinked Complexes for Tandem Mass Spectrometry

Quenched reaction mixtures were loaded to 14 lanes of four separate 7.5% acrylamide hand-cast SDS-tris polyacrylamide gels (Bio-Rad system, 1.0 mm width). Gels were run for at 180 V for 40 min and then incubated with InstantBlue (Expedeon) for 10 min before storing in double distilled $H_2O$.

Denaturing Electroelution of Photocrosslinked Complexes from the Gel Matrix

Figure 10:
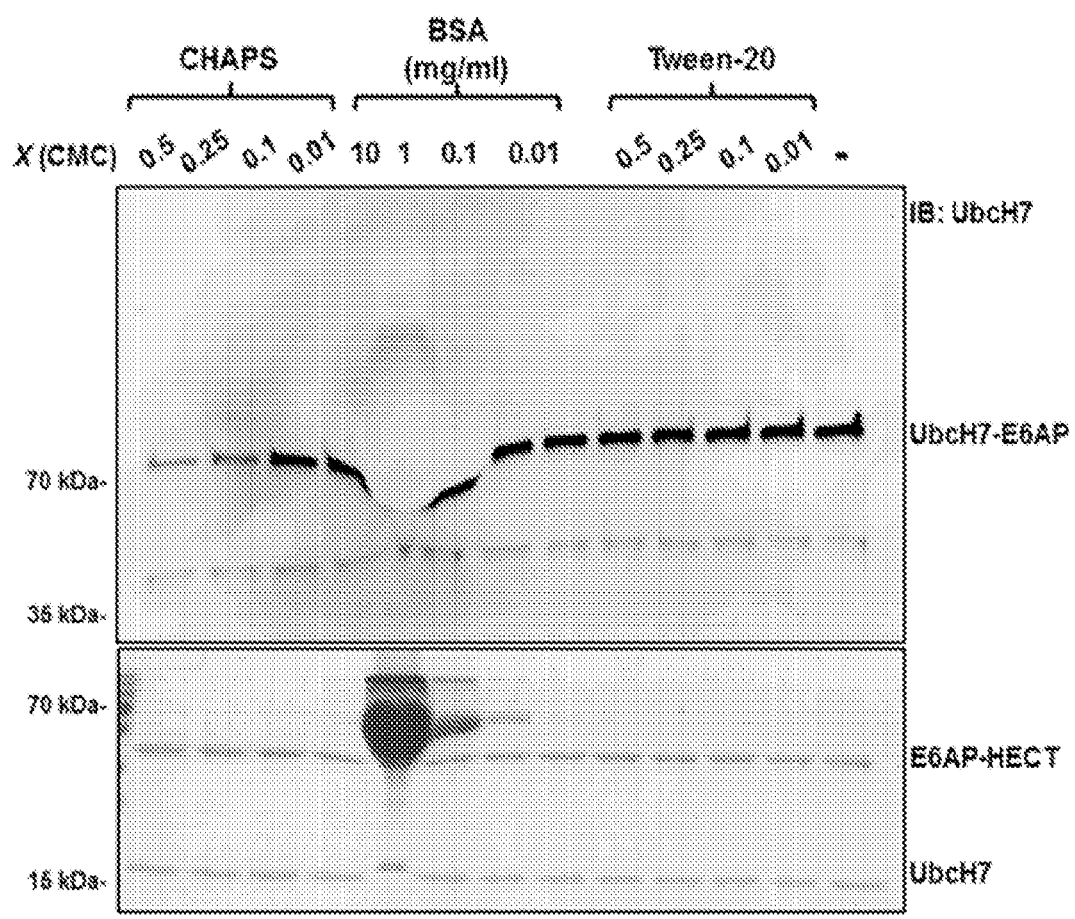
FIG. 10. UbcH7/E6AP crosslinking tolerates detergents or BSA. UbcH7 CΔS E93C-1 (6 µM) and E6AP-HECT (6 µM) were mixed in PBS(B) with 1 mM DTT in the presence of the indicated additive at a fraction of its critical micelle concentration (CMC) or BSA (mg/mL). Reaction mixtures were irradiated at 365 nm for 10 minutes and quenched with 6× Laemmli buffer and β-ME. Reaction mixtures were boiled at 95° C. for 5 minutes, resolved by SDS-PAGE, and visualized by western blot (top) or coomassie (bottom).
Figure 11:
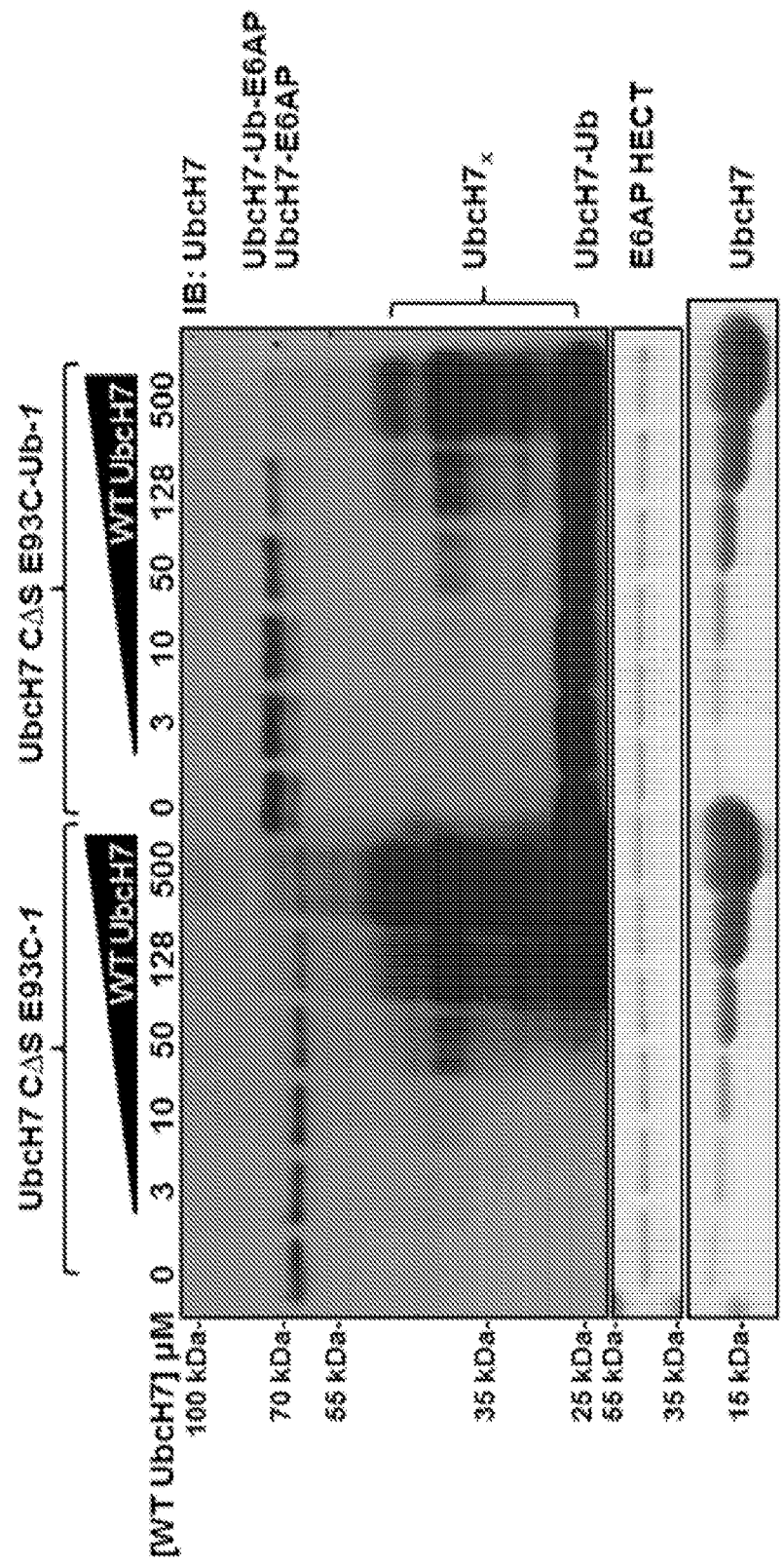
FIG. 11. UbcH7/E6AP crosslinking diminishes upon competition with WT UbcH7. E6AP-HECT (3 µM) was mixed with PBS(B), 800 µM CHAPS, 1 mM DTT and different concentrations of wild type UbcH7. Reactions were mixed and incubated at room temperature for 5 minutes before adding UbcH7 CΔS E93C-1 or UbcH7 CΔS E93C Ub-1 (3 M). Reactions were mixed and then irradiated for 10 minutes at 365 nm before quenching with 6× Laemmli/β-ME and warming at 95° C. for 5 minutes. An increased concentration of UbcH7 decreases UbcH7-E6AP crosslinking.
Figure 14A:
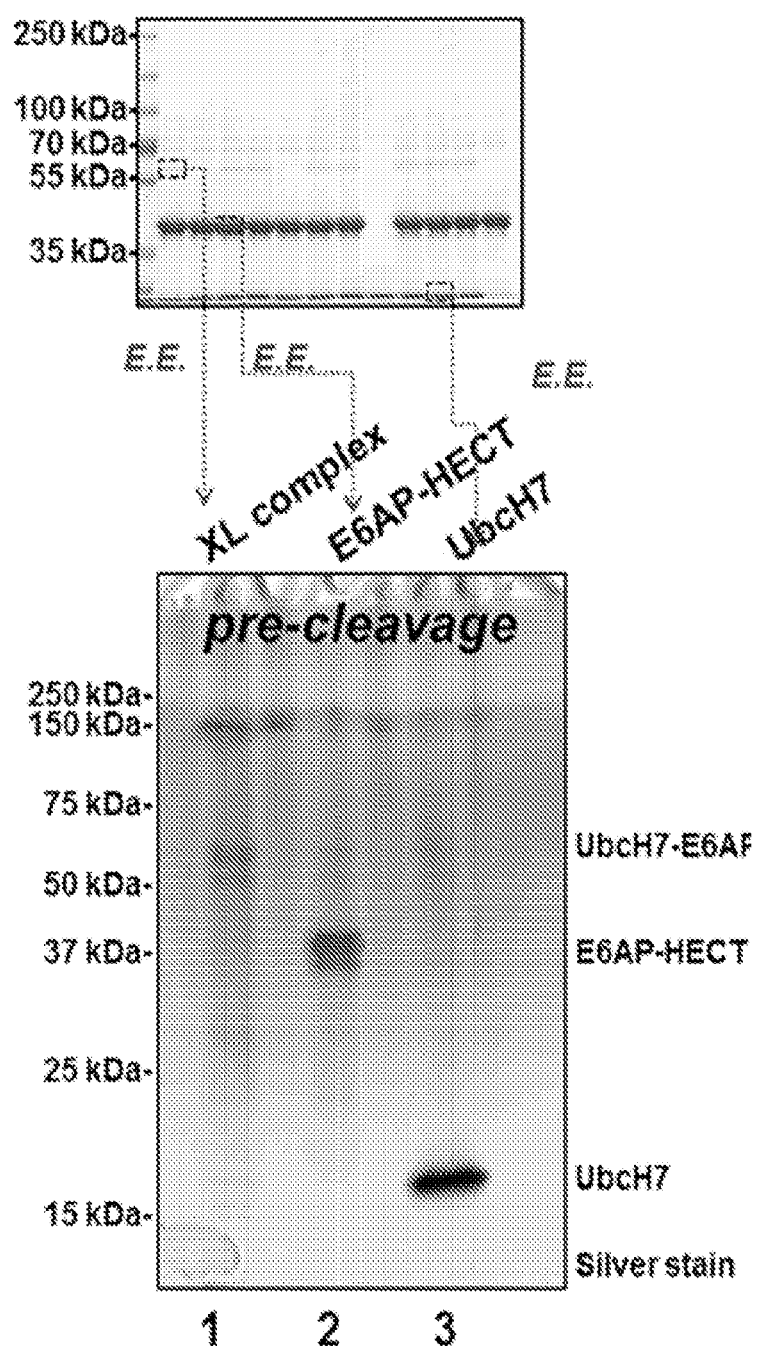

Gel bands containing photocrosslinked E6AP/UbcH7 complexes were excised (FIG. 10) and sliced to ~1 $mm^2$ cubes using a scalpel. The gel pieces were then added to the central chamber of the assembled electroelution device (FIG. 14). After adding the gel pieces, 200 μL Tris-Glycine-SDS buffer were added to the central chamber (a single electroelution run was performed on a single gel's worth of bands). The lateral chambers were filled with the same buffer (~9 mL) before connecting the anode and cathode to an electrophoresis box (Bio-Rad PowerPac 1000). Current was run at 8-14 milliamps, 50 V for 10 minutes. The solution containing electroeluted complexes was collected using a gel loading pipette tip. Another 200 μL of buffer were added to the same gel pieces, and the device was run again as described above to extract the remaining proteins. The second 200 μL fraction was then combined with the first in a 1.5 mL microcentrifuge tube and stored briefly at 4° C. (1-3 hours) before acidifying with HCl as described below.

Electroelution fractions in Tris-Glycine-SDS buffer were treated with 1 M aqueous HCl (protein sample/1 M HCl 4:1 v/v) to obtain pH 1 in a 1.5 microcentrifuge tube (one gel's worth of elution per tube). After briefly vortexing, the sample was then placed in a heating block at 55° C. Another heating block at the same temperature was placed on top of the microcentrifuge tubes to heat the tube caps. Samples were heated for 2 hours and then neutralized with 3 M NaOH (acidified sample/3 M NaOH 12:1 v/v) to obtain pH 9. At this point, the sample was immediately submitted to acetone precipitation Example with volumes: 400 μL electroeluted sample per gel+100 μL 1 M HCl→heat at 55° C.→+41.5 μL 3 M NaOH.

Acetone Precipitation of Cleaved Protein Complexes

Acetone precipitation was performed immediately after neutralization with NaOH. First, each reaction mixture per gel was divided in half (from ~550 μL, two 225 μL portions were each placed into two separate 2 mL microcentrifuge tubes). To each 2 mL tube was then added 1.25 mL cold acetone pre-chilled to −20° C. These tubes were then lightly vortexed and immediately placed at −80° C. for 1 hour before centrifuging at 21,100 g, 4° C. for 10 minutes. After carefully removing the resulting supernatant with pipette, another 1.25 mL acetone pre-chilled to −20° C. were added to each tube which was then immediately centrifuged at 21,100 g, 4° C. for 10 minutes. The supernatants were carefully removed by pipette, the pellets were set to air-dry for 30 minutes, and were then stored overnight at −20° C.

Sample Preparation for Mass Spectrometry

Pellets from acetone precipitation were dissolved in FPLC-purified 8 M urea (5 μL per 2 mL tube) and incubated at 60° C. for 1 h (heating blocks were placed above and below tubes just as in the acidification step described above). $NH_4HCO_3$ (100 mM, 15 μL/tube) was then added to each tube along with DTT (55 mM in 25 mM $NH_4HCO_3$, 2 μL/tube). These solutions were mixed by pipetting and then incubated at 56° C., 190 RPM for 30 minutes. Iodoacetamide (125 mM in 25 mM $NH_4HCO_3$, 3 μL/tube) was then added and mixed. Tubes were incubated in the dark at room temperature for 30 minutes. To each tube was then added $NH_4HCO_3$ (100 mM, 20 μL/tube) along with freshly prepared trypsin (lyophilized, Promega V511A, prepared according to manufacturer's protocol, 5.3 ng/μL final concentration). The solutions were mixed by pipette and then incubated at 37° C. for 12 hours.

The digested samples were desalted using reverse phase C18 spin columns (Thermo Fisher Scientific, Rockford, IL.). After desalting, the peptides were concentrated to dryness in vaccuo. Peptides were then suspended in 5% acetonitrile and 0.1% formic acid. The samples were loaded directly onto a 15 cm long, 75 μM reversed phase capillary column (ProteoPep™ II C18, 300 Å, 5 μm size, New Objective, Woburn MA.) and separated with a 200 minute gradient from 5% acetonitrile to 100% acetonitrile on a Proxeon Easy n-LC II (Thermo Scientific, San Jose, Calif.). The peptides were directly eluted into an LTQ Orbitrap Velos mass spectrometer (Thermo Scientific, San Jose, Calif.) with electrospray ionization at 300 nl/minute flow rate. The mass spectrometer was operated in data dependent mode, and for each MS1 precursor ion scan the ten most intense ions were selected from fragmentation by CID (collision induced dissociation). The other parameters for mass spectrometry analysis were: resolution of MS1 was set at 60,000, normalized collision energy 35%, activation time 10 ms, isolation width 1.5, and +4 and higher charge states were rejected.

The data were processed using Proteome Discoverer (version 1.4, Thermo Scientific, San Jose, Calif.) with an embedded Sequest HT search engine. The data were searched with a custom database with three sequences: UBE2L3, human ubiquitin, and the HECT domain of UBE3A (see sequences given below). The other parameters were as follows: (i) enzyme specificity: trypsin; (ii) fixed modification: cysteine carbamidomethylation; (iv) variable modification: methionine oxidation and N-terminal acetylation; Crosslinker iodoacetamide sulfamic acid modification (136.9783 Da), crosslinker 2 butanol modification (72.0575 Da), or the deuterated crosslinker 3 butanol modification (77.0889 Da); (v) precursor mass tolerance was ±10 ppm; and (vi) fragment ion mass tolerance was ±0.8 Da. All the spectra were searched against target/decoy databases and a targeted q value of 0.1 was used as the cut-off to consider the peptide assignment as valid. Since the butanol modification to E6AP was non-specific, each raw file was searched with variable modifications corresponding to each amino acid. The spectrum assigning the modification to a particular amino acid was only considered valid after manual interpretation of the spectrum. All relevant spectra are given in Spectral Appendix I below. We observed ~70% sequence coverage of E6AP HECT domain with trypsin.

Example 3

E2-E6AP Crosslinking

Protein ubiquitination is an important posttranslational modification that regulates many aspects of human biology (ref. 1; herein incorporated by reference in its entirety). E6AP (UBE3A) is the founding member of HECT E3 ubiquitin ligases, which form an obligatory thioester intermediate with ubiquitin prior to substrate ubiquitination (ref. 2; herein incorporated by reference in its entirety). In Angelman syndrome patients, the maternal allele of E6AP harbors inactivating mutations or a gene deletion (ref. 3; herein incorporated by reference in its entirety), while human papillomavirus hijacks E6AP to degrade the p53 tumor suppressor in cervical cancers (ref. 4; herein incorporated by reference in its entirety). Understanding the mechanisms that regulate the activity of E6AP is therefore fundamentally important. UbcH7, the E2 enzyme upstream of E6AP, transfers ubiquitin (Ub) from a UbcH7-Ub thioester onto the catalytic cysteine of E6AP (ref. 5; herein incorporated by reference in its entirety). The E6AP~Ub thioester can then catalyze the formation of an isopeptide bond between Ub and the substrate. E6AP forms efficient binding interactions with both UbcH7 and UbcH7-Ub thioester (ref. 6; herein incorporated by reference in its entirety). However, it was recently suggested that E6AP harbors two distinct E2 enzyme-binding sites (ref. 7; herein incorporated by reference in its entirety) and may function as an oligomer ([ref. 8; herein incorporated by reference in its entirety).

Inactivation of the E6AP E3 ubiquitin ligase (UBE3A gene) causes Angelman syndrome, while aberrant degradation of the p53 tumor suppressor by E6AP is implicated in cervical cancers. Therefore, it is important to understand how the enzymatic activity of E6AP is regulated. Experiments conducted during development of embodiments herein demonstrate a robust, cysteine reactive, acid-cleavable minimalist photocrosslinker and its application to, for example, discover catalytically relevant residues of the E6AP (or other enzymes or proteins). By equipping the E2 enzyme upstream of E6AP with crosslinker, the E6AP catalytic environment that governs ubiquitin transfer has been interrogated. This approach features, for example: (i) site-specific installation of a photocrosslinker on the E2 enzyme surface using cysteine chemistry, (ii) an acid-cleavable N-acylsulfamate moiety in the linker to facilitate MS/MS analysis of photocrosslinked peptides, (iii) an electroelution method to purify photocrosslinked protein complexes prior 10 acid-cleavage, and (iv) a simple synthetic route to vicinal deuteration of the photo-reactive alkyl diazirine functional group. This isotopically labeled photocrosslinker further facilitates the analysis and ID of photocrass-linked peptides. Using this crosslinker, covalent modifications of the E6AP catalytic cysteine and two lysines: $Lys^{847}$ and $Lys^{799}$ were observed. $Lys^{847}$ is required for the formation of $Lys^{48}$-linked polyubiquitin chains. While the K799A mutant was more active at producing $Lys^{48}$-linked polyubiquitin chains. $Lys^{799}$ of E6AP is located near a patch of residues ($^{801}KMII^{804}$) that are mutated or deleted in Angelman syndrome patients leading to E6AP inactivation. Thus, opposing roles of $Lys^{847}$ and $Lys^{799}$ pave the path forward to pharmacological inhibitors or activators of E6AP to treat Angelman syndrome and cancers.

This approach is applicable to map tens of thousands of possible E2/E3 interactions and any other protein-protein interactions.

Figure 1B:
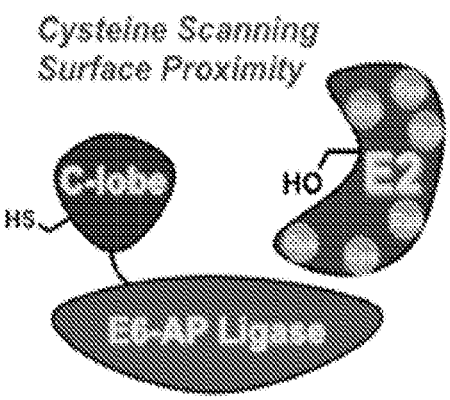
Figure 1D:
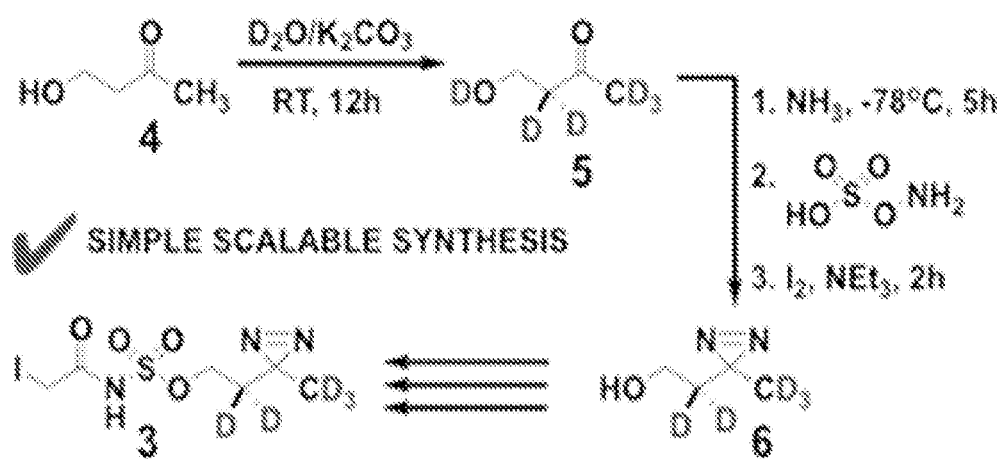
Figure 1C:
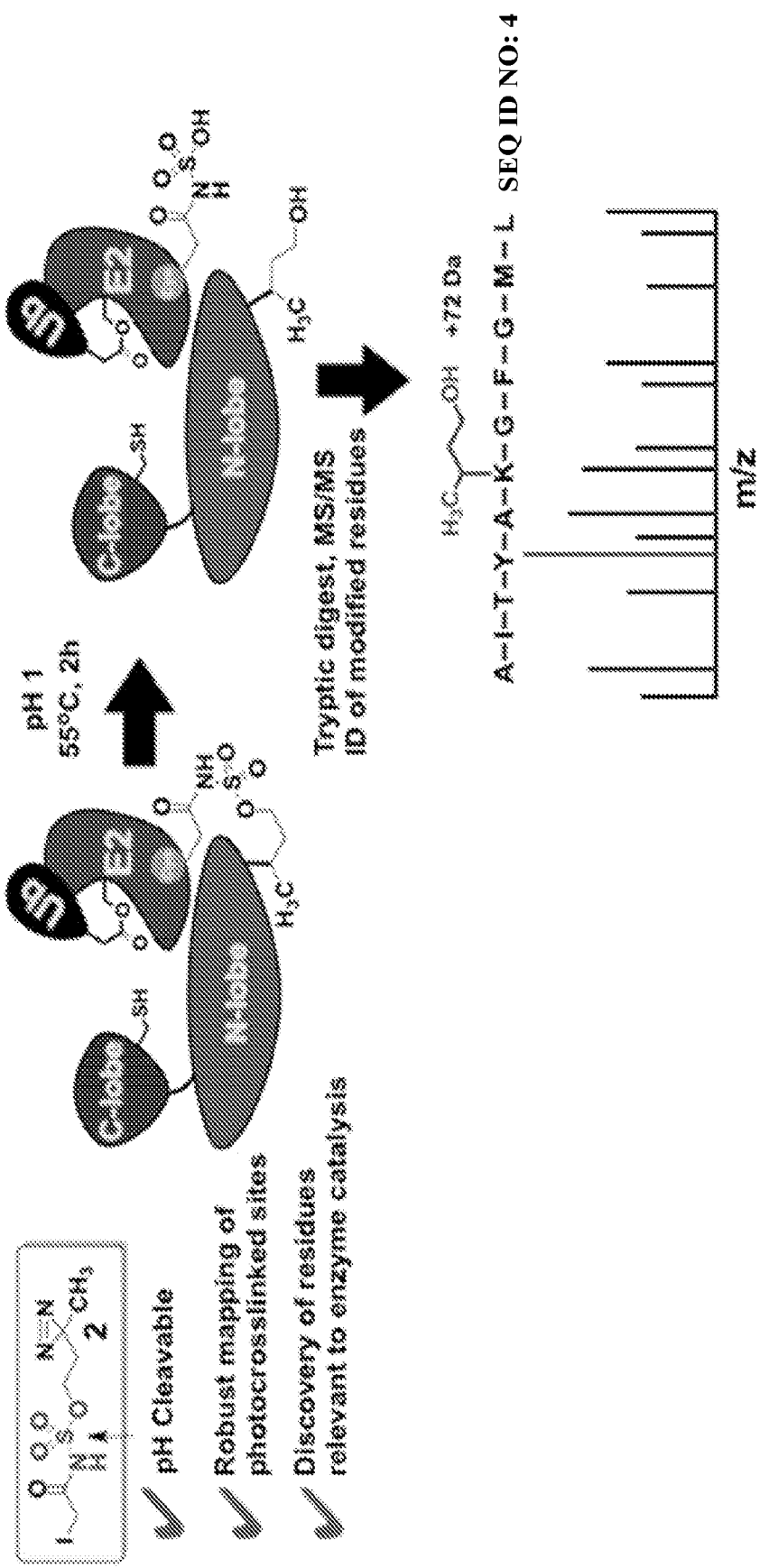

Robust and sterically small photocrosslinking reagents were developed to identify proximal and catalytically relevant residues at transient E2/E3 protein-protein interfaces (FIG. 1A-C). Such photocrosslinkers act as useful and general tools to map protein-protein interactions (e.g., in vitro). To equip E2 enzyme with crosslinkers that are sterically small and also suitable for MS analysis of crosslinked peptides, a set of mono-cysteine mutants were developed, to be alkylated with the iodoacetamide-diazirine photocrosslinkers 1, 2, or 3 (FIG. 1, Tables 1 and 2) (ref. 9; herein incorporated by reference in its entirety).

TABLE 1

Alkylation conversion of UbcH7 estimated by LCMS. UbcH7 mutants with a single cysteine available (100-200 μM) were incubated with crosslinker (5 mM final concentration) for 90 minutes before desalting into PBS(B). Incubation was done at room temperature with crosslinker 1 or at 4° C. for crosslinkers 2 or 3. Two mutants that experienced poor conversion (N31C and L33C) with 2 were tested with the room temperature alkylation condition. While yields did improve, the appearance of di-alkylation occurred.

| 1 alkylation | | 2 alkylation | | 3 alkylation | |
|---|---|---|---|---|---|
| M1C | >95% M1C | >95% | | | |
| A2C | >95% A2C | >95% | | | |
| A3C | >95% A3C | >95% | | | |
| A3C-Ub | >95% A3C-Ub | Not tested | | | |
| S4C | >95% S4C | >95% | | | |
| C17 | >95% C17 | ~50% | | | |
| L33C | >95% L33C | ~20% | 50% at RT | | |
| N31C | >95% N31C | ~33% | 80% at RT | | |
| E60C | >95% E60C | >95% | | | |
| C86 | >95% C86 | ~60% | | | |
| E93C | >95% E93C | >95% | | | |
| E93C-Ub | >95% E93C-Ub | >95% | | | |
| C137 | >95% C137 | <5% | | | |
| F63A mutants | | | | | |
| A2C | >95% A2C | Not tested | | | |
| S4C | >95% S4C | Not tested | | | |
| E93C | >95% E93C | >95% | | E93C | >95% |
| E93C-Ub | >95% E93C-Ub | >95% | | E93C-Ub | >95% |

TABLE 2

LCMS results for UbcH7 alkylation.

| | Calculated | Observed |
|---|---|---|
| Alkylation with crosslinker 1 | | |
| M1C | 18335.96 | 18336.05 |
| A2C | 18396.08 | 18396.03 |
| F63A A2C | 18319.98 | 18319.97 |
| A3C | 18396.08 | 18396.12 |
| A3C-Ub | 26942.91 | 26943.05 |
| S4C | 18380.08 | 18380.23 |
| F63A S4C | 18303.98 | 18304.04 |
| C17 | 18380.08 | 18380.25 |
| N31C | 18353.05 | 18353.34 |
| L33C | 18353.96 | 18354.39 |
| E60C | 18337.96 | 18338.30 |
| C86 | 18380.08 | 18380.22 |
| E93C | 18337.96 | 18338.40 |
| E93C-Ub | 26884.76 | 26885.11 |
| C137 | 18380.08 | 18380.12 |
| Alkylation with crosslinker 2 | | |
| M1C | 18416.02 | 18416.13 |
| A2C | 18476.14 | 18475.94 |
| A3C | 18476.14 | 18477.23 |
| S4C | 18460.14 | 18458.02 |
| C17 | 18460.14 | 18460.63 |
| L33C | 18434.02 | 18435.85 |
| N31C | 18433.11 | 18432.96 |
| E60C | 18418.02 | 18418.03 |
| C86 | 18460.14 | 18460.65 |
| E93C | 18418.02 | 18418.36 |
| F63A E93C | 18341.92 | 18342.02 |
| E93C-Ub | 26964.82 | 26965.29 |
| F63A E93C-Ub | 26888.72 | 26888.71 |
| C137 | 18460.14 | 18460.68 |
| Alkylation with crosslinker 3 | | |
| E93C | 18423.05 | 18422.88 |
| E93C-Ub | 26969.85 | 26969.08 |

Alkylated E2 enzyme was subsequently be purified and photocrosslinked to its downstream E3. The short linker lengths in 1-3 (~8 Å for 1, and ~11 Å for 2, 3) minimize disruption to the protein-protein interface, and the cysteine-reactive iodoacetamide allows site-specific installation on a protein surface using cysteine chemistry. After photocrosslinking, MS/MS identification of modified residues was performed by cleaving the crosslinker at acidic pH to render unbound proteins with unique covalent modifications at crosslinked sites (FIG. 1C). In some embodiments, this step is desirable since non-cleavable photocrosslinkers produce reaction mixtures that demand complex analysis (ref. 10; herein incorporated by reference in its entirety). Although, in some embodiments, site-specific installation of photocrosslinkers is achieved using unnatural amino acid incorporation (ref. 11; herein incorporated by reference in its entirety), cysteine chemistry provides a simple and flexible approach, and due to the relative scarcity of cysteine residues comparted to other potentially-reactive side chains (e.g., lysine), cysteine allows a user to achieve site-specific installation of these crosslinkers on protein surfaces.

Figure 2A:
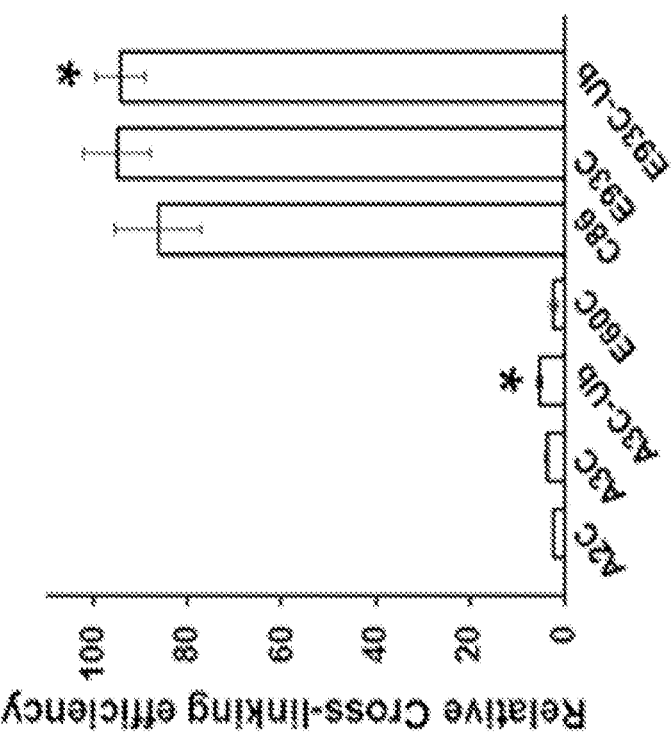
Figure 2B:
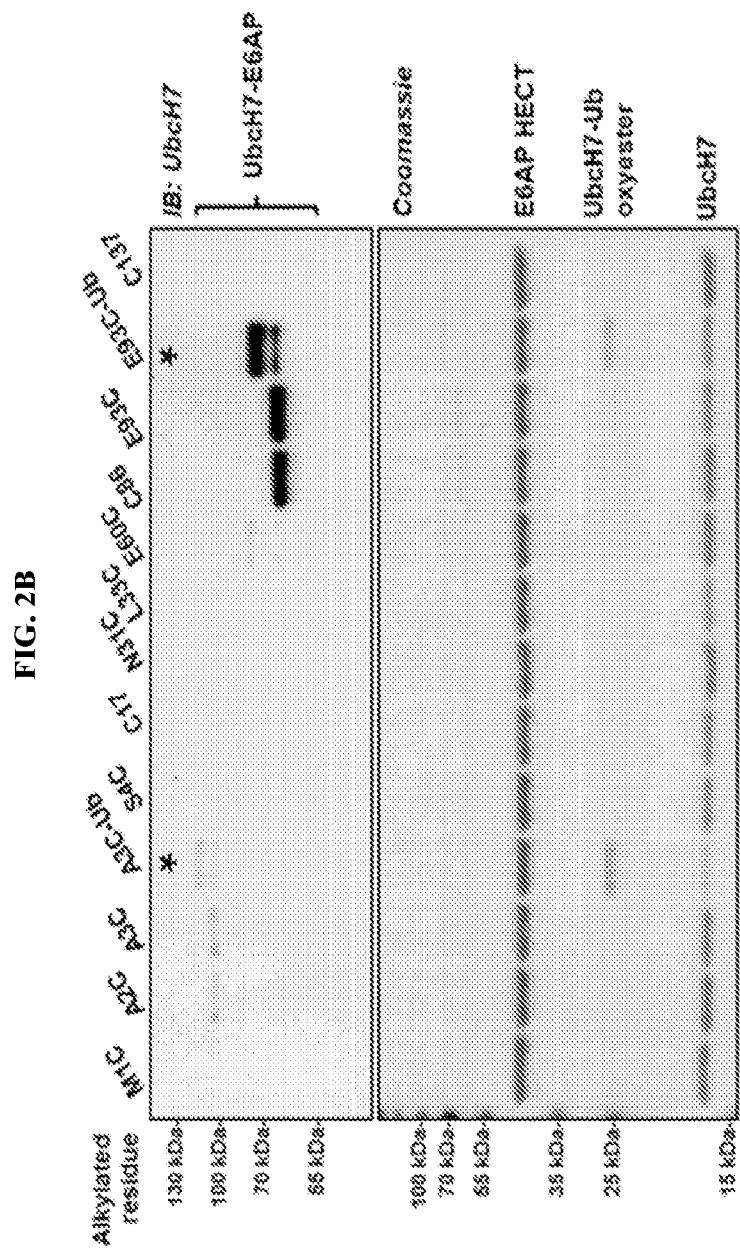

To identify which UbcH7 surfaces interact with E6AP, photocrosslinker 1 was site-specifically mono-alkylated to a set of UbcH7 mutants that each had cysteine introduced at a distinct surface (FIG. 2A). After desalting, each photoreactive UbcH7 enzyme was investigated for its ability to undergo photocrosslinking with E6AP HECT domain (FIG. 2B, C). Thus, the entire surface of UbcH7 enzyme was scanned for proximity to E6AP in solution. To identify modified E6AP residues, the UbcH7 mutant that most efficiently crosslinked when modified by 1 was equipped with crosslinker 2, which harbors an acid-cleavable N-acylsulfamate moiety (ref. 12; herein incorporated by reference in its entirety).

Figure 4:
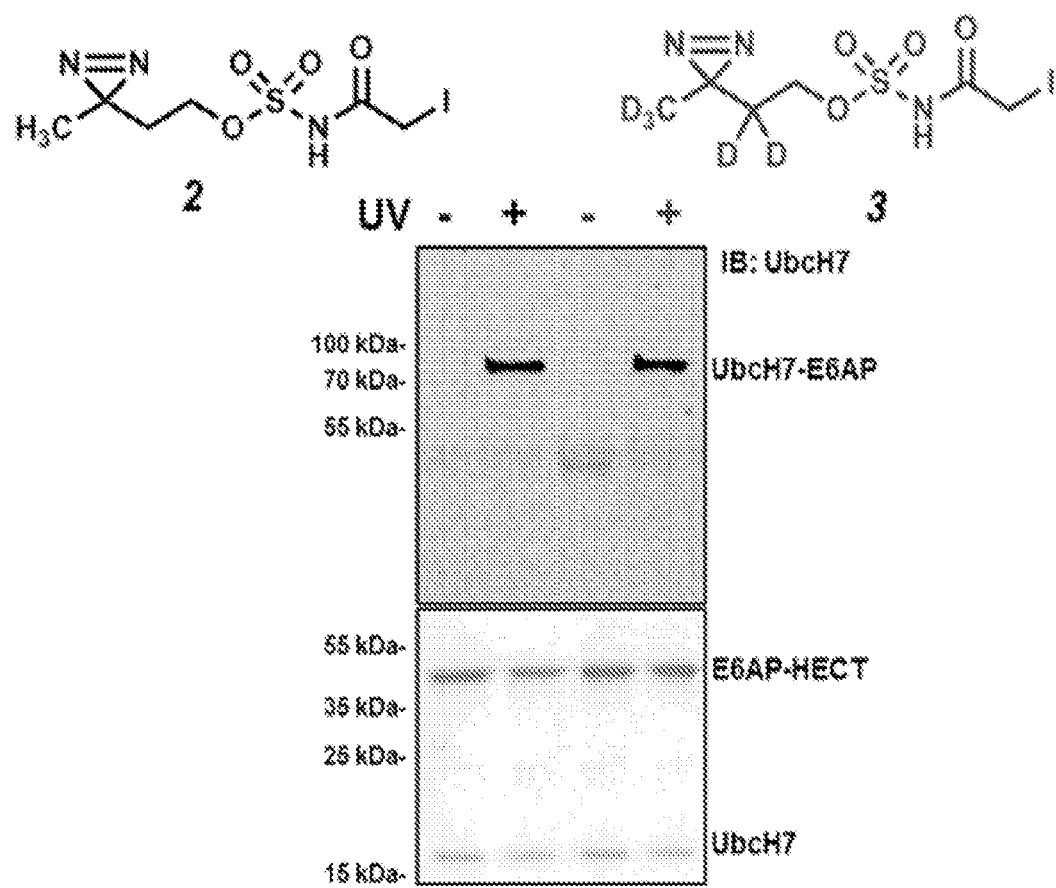
FIG. 4. Crosslinkers 2 and 3 have equal photocrosslinking efficiency. UbcH7 CΔS E93C-2 or UbcH7 CΔS E93C-3 (10 µM final concentration) was incubated with E6AP-HECT (10 µM final concentration) in PBS(B) with 6 µM Tween-20 and 1 mM DTT. After keeping samples in the dark or irradiating at 365 nm for 10 minutes, they were quenched with 6× Laemmli buffer and β-mercaptoethanol (β-ME) and then boiled at 95° C. for 5 minutes. Covalently crosslinked protein complexes were resolved by SDS-PAGE and visualized by western blot and coomassie.

Cleavage of photocrosslinked peptides facilitates their subsequent MS and MS/MS analysis (FIG. 1C) (ref. 10; herein incorporated by reference in its entirety). Thus, cleavage of the UbcH7-E6AP crosslink prior to digestion and mass analysis provided robust signal of E6AP peptides with a unique butanol covalent modification (+72.06 Da). The identification of these residues was further supported by an analogous experiment with the deuterated diazirine 3, which was developed by a simple synthetic protocol (FIG. 1D, +77.09 Da butanol-d5 modification). The developed synthesis of 3 features a facile H/D exchange on the readily available hydroxyl-ketone starting material with $D_2O$/$K_2CO_3$, followed by its conversion to diazirine. Importantly, α-deuterated ketone survived subsequent conversion to α-deuterated diazirine in liquid ammonia without the reverse D/H exchange. Crosslinker 2 and deuterated crosslinker 3 showed equal photocrosslinking efficiency (FIG. 4).

Figure 5A:
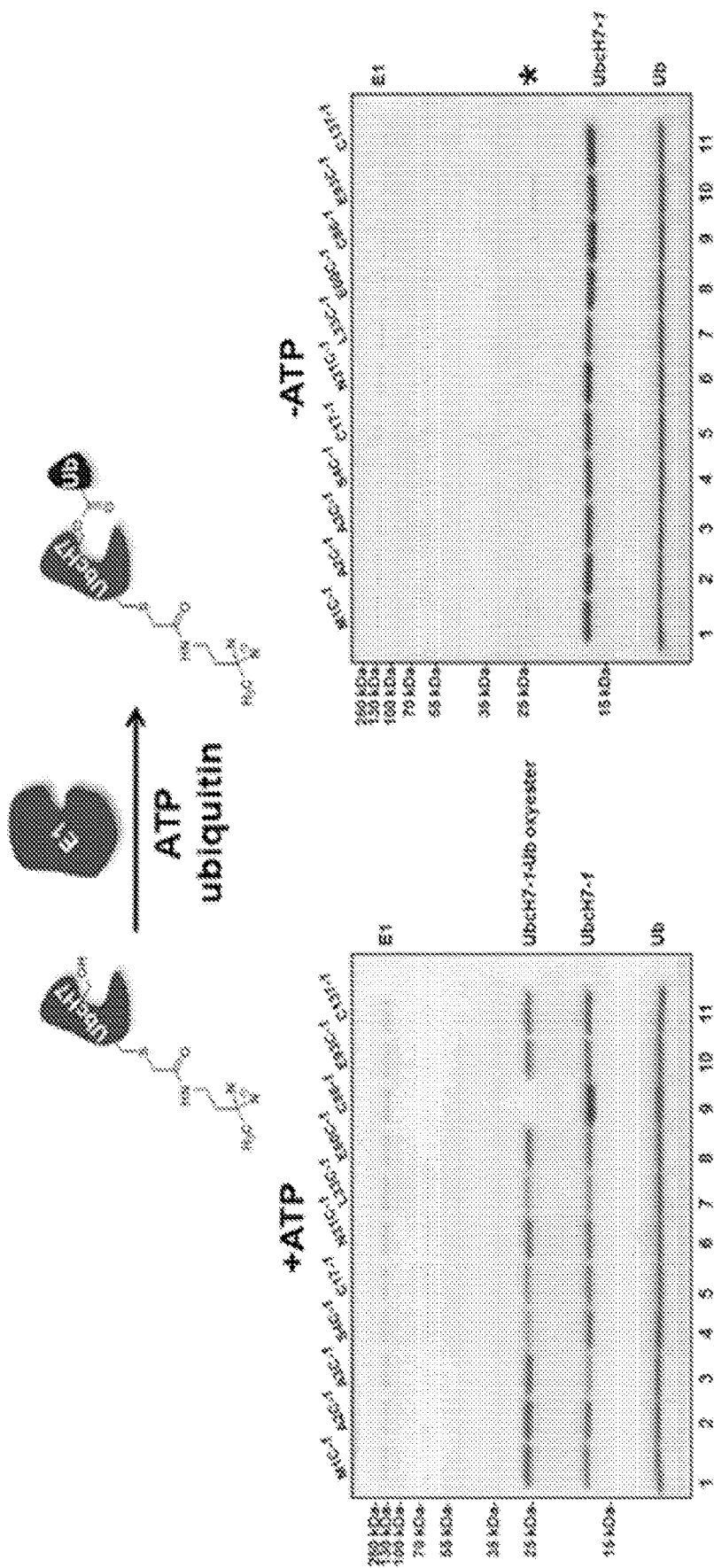
Figure 5B:
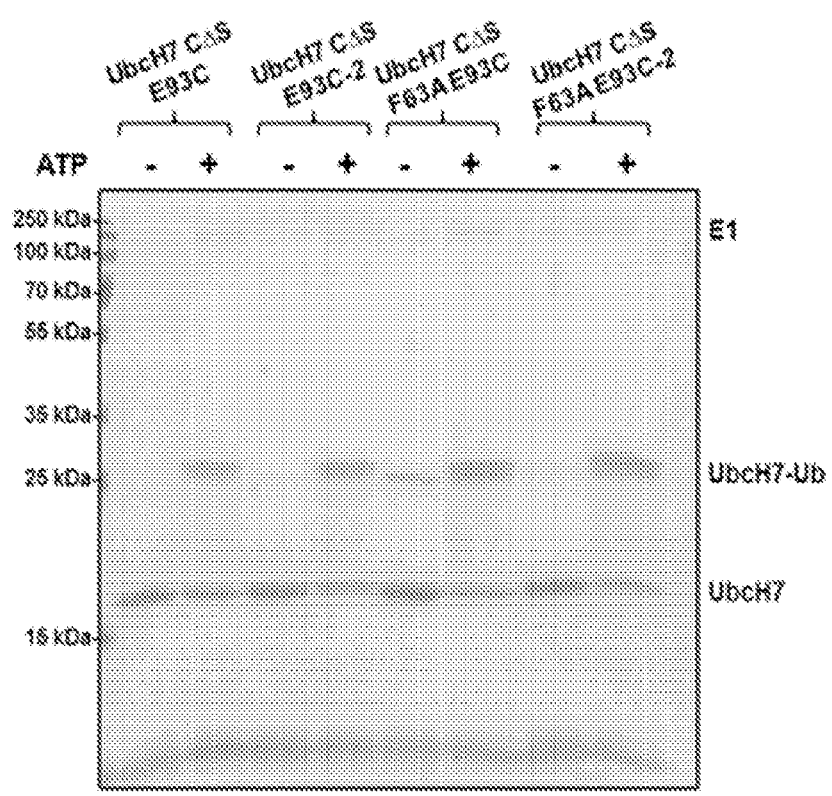

While crosslinker 1 quantitatively labeled every UbcH7 cysteine mutant, 2 and 3 were not as reactive with some of the mutants (Tables 1-2,). This may be due to deprotonation of the acylsulfamate, which reduces the reactivity of 2 and 3 toward thiol nucleophiles (ref. 12; herein incorporated by reference in its entirety). Therefore, crosslinker 1 was first used to rapidly survey the proximity of UbcH7 surfaces to an interface with E6AP. To avoid non-specific alkylation of native UbcH7 cysteine residues Cys17, Cys86 (catalytic cysteine), and Cys137, they were mutated to serine (referred to as UbcH7 CΔS). While Cys86 is the key catalytic residue to mediate Ub transthiolation, UbcH7 CΔS and its alkylated analogues are competent to form UbcH7 C86S-Ub oxyester conjugates (UbcH7 CΔS-Ub) in the presence of ATP and ubiquitin-activating E1 enzyme (FIG. 5A-B). Furthermore, UbcH7 CΔS-Ub and its alkylated analogues can transfer ubiquitin to E6AP (FIG. 5C). These data indicate that mutagenesis and alkylation with crosslinkers 1, 2, or 3 did not compromise the E2 enzyme structure.

An UbcH7/E6AP co-crystal structure (ref. 13; herein incorporated by reference in its entirety) and an alanine scan of the protein-protein interface (ref. 14; herein incorporated by reference in its entirety) initially guided our selection of UbcH7 residues near the interface to equip with crosslinker. Ideally, a residue chosen for alkylation should not significantly contribute to the E6AP:UbcH7 binding interaction. Thus, we selected residues that did not markedly affect binding affinity when mutated to alanine (ref. 14; herein incorporated by reference in its entirety).

Based on this criterion, UbcH7 CΔS mutants N31C, L33C, E60C, or E93C were alkylated with photocrosslinker 1. Furthermore, the UbcH7/E6AP co-crystal structure indicates that the first three N-terminal UbcH7 residues positioned near the UbcH7:E6AP interface are disordered. It was hypothesized that these residues did not contribute significantly to the UbcH7/E6AP binding interaction, and could therefore serve as suitable residues to install photocrosslinker. Thus, UbcH7 residues M1C, A2C, A3C, and S4C were selected as additional sites for crosslinker attachment. To explore the UbcH7/E6AP interaction landscape and to validate the specificity of crosslinking, mono-cysteine UbcH7 mutants were also made to place crosslinker at native cysteines Cys17, Cys86, or Cys137 (FIG. 2).

Figure 6:
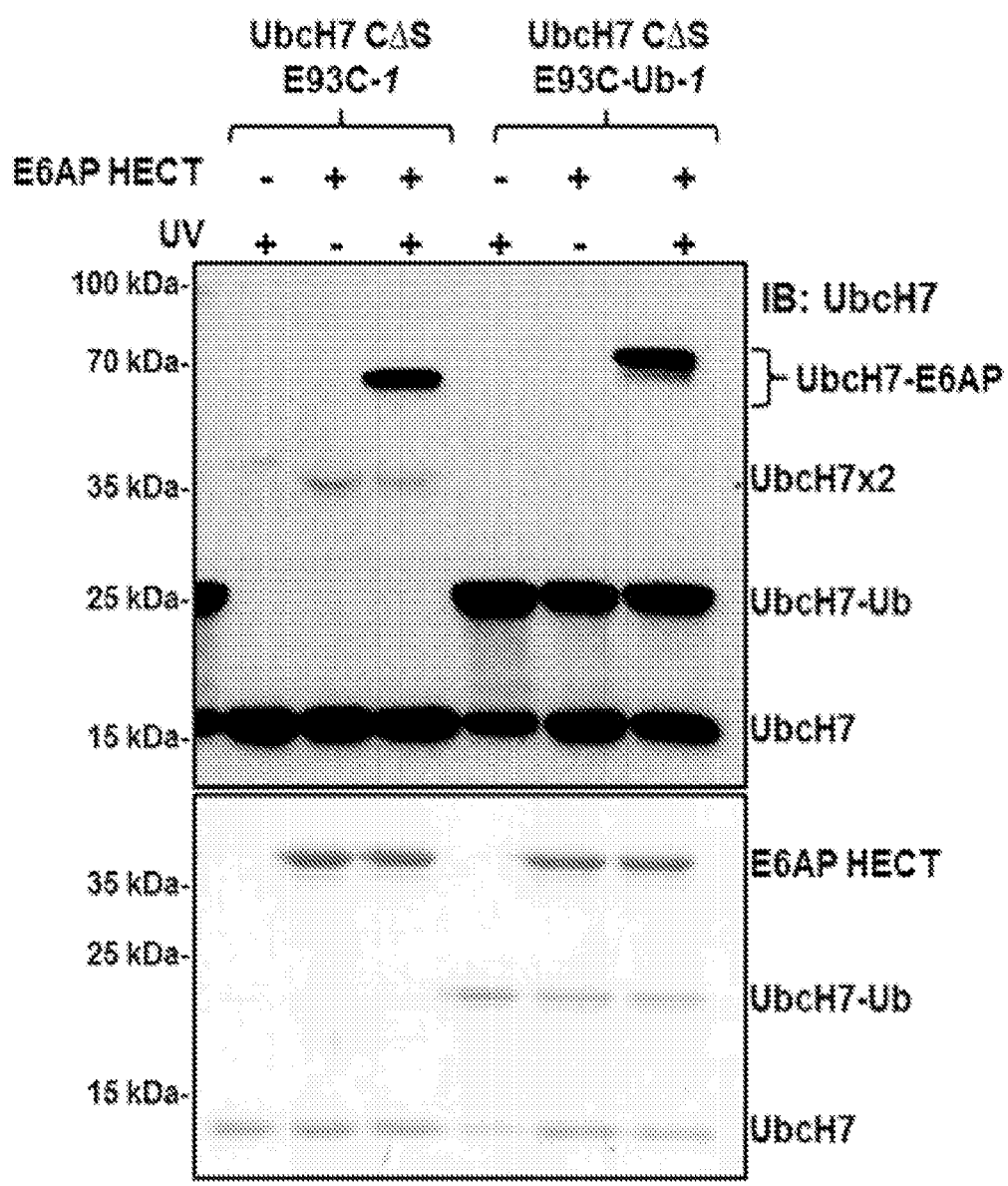
FIG. 6. UbcH7 CΔS-1 crosslinking depends on the presence of E6AP-HECT and UV irradiation. Either UbcH7 CΔS E93C-1 (18,338 kDa, 10 µM) or UbcH7 CΔS E93C-Ub-1 (26,885 kDa, 10 µM) were mixed in PBS(B), 1 mM DTT, 6 µM Tween-20 with or without E6AP-HECT (43,368 kDa, 10 µM). Samples were irradiated for 10 minutes at 365 nm or kept out of light during that time. After this time, samples were quenched with 6× Laemmli buffer with β-ME, and boiled at 95° C. for 5 minutes. A faint UbcH7 dimer band is observed in crosslinking experiments where UbcH7 is not charged with ubiquitin. Hydrolysis of UbcH7 CΔS-Ub oxyesters liberates free UbcH7 to produce a band at the bottom of the western blot.

Alkylation of UbcH7 cysteine mutants occurred readily by incubating 50-300 μM UbcH7 with 5 mM crosslinker 1 at room temperature for 90 minutes before removing free crosslinker with a desalting column. Intact protein mass spectrometry indicated near quantitative mono-alkylation of all mono-cysteine UbcH7 mutants (Tables 1-2). The UbcH7 CΔS-1 mutants (10 μM) were then mixed with the E6AP catalytic HECT domain (10 μM) and irradiated at 365 nm for 10 minutes in a 96-well plate. The reaction mixtures were then resolved with reducing SDS-PAGE and analyzed with anti-UbcH7 western blot. Photocrosslinking of UbcH7 to E6AP depends on the presence of both UV irradiation and E6AP (FIG. 6). Western blotting showed that UbcH7 CΔS mutants crosslink E6AP with varying degrees of efficiency. The most efficient crosslinking resulted when crosslinker 1 was placed at either UbcH7 CΔS E93C, or at the UbcH7 catalytic cysteine Cys86 (FIG. 2B-C). Since UbcH7-Ub thioester is the true substrate of E6AP, we prepared the stable E2-Ub oxyesters UbcH7 CΔS E93C Ub-1 or UbcH7 CΔS A3C Ub-1, and observed comparable crosslinking efficiency to their non-ubiquitinated analogues (FIG. 2B-C).

Figure 7B:
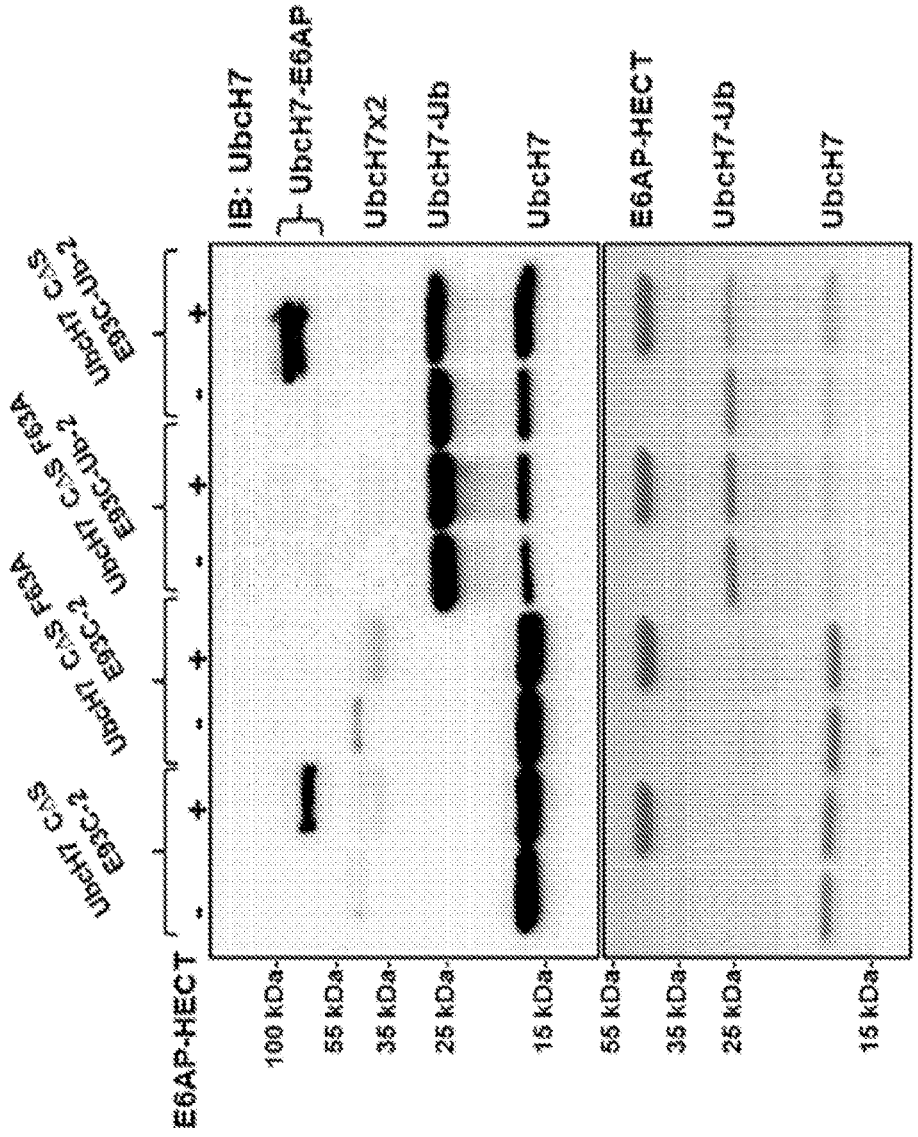
FIGS. 7A-C. UbcH7/E6AP HECT crosslinking is specific for E2/HECT binding. (A.) The binding affinity of UbcH7 and E6AP-HECT is $K_d$=5 µM. The insert shows Phe$^{63}$ of UbcH7 contacting a hydrophobic groove of E6AP. The binding affinity of UbcH7 F63A for E6AP-HECT is $K_d$=~800 µM. PDB: 1C4Z. UbcH7 F63A was used as a negative control for crosslinking E6AP. (B and C). The UbcH7-E6AP crosslink is not observed for F63A mutants even though they are competent to form UbcH7 F63A CΔS-Ub oxyesters in the presence of E1, Ub, and ATP (see FIG. 4B).
Figure 7A:
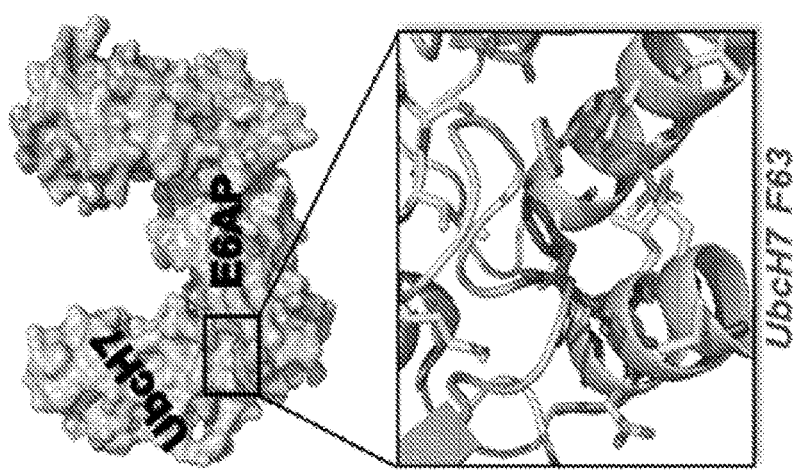
Figure 7C:
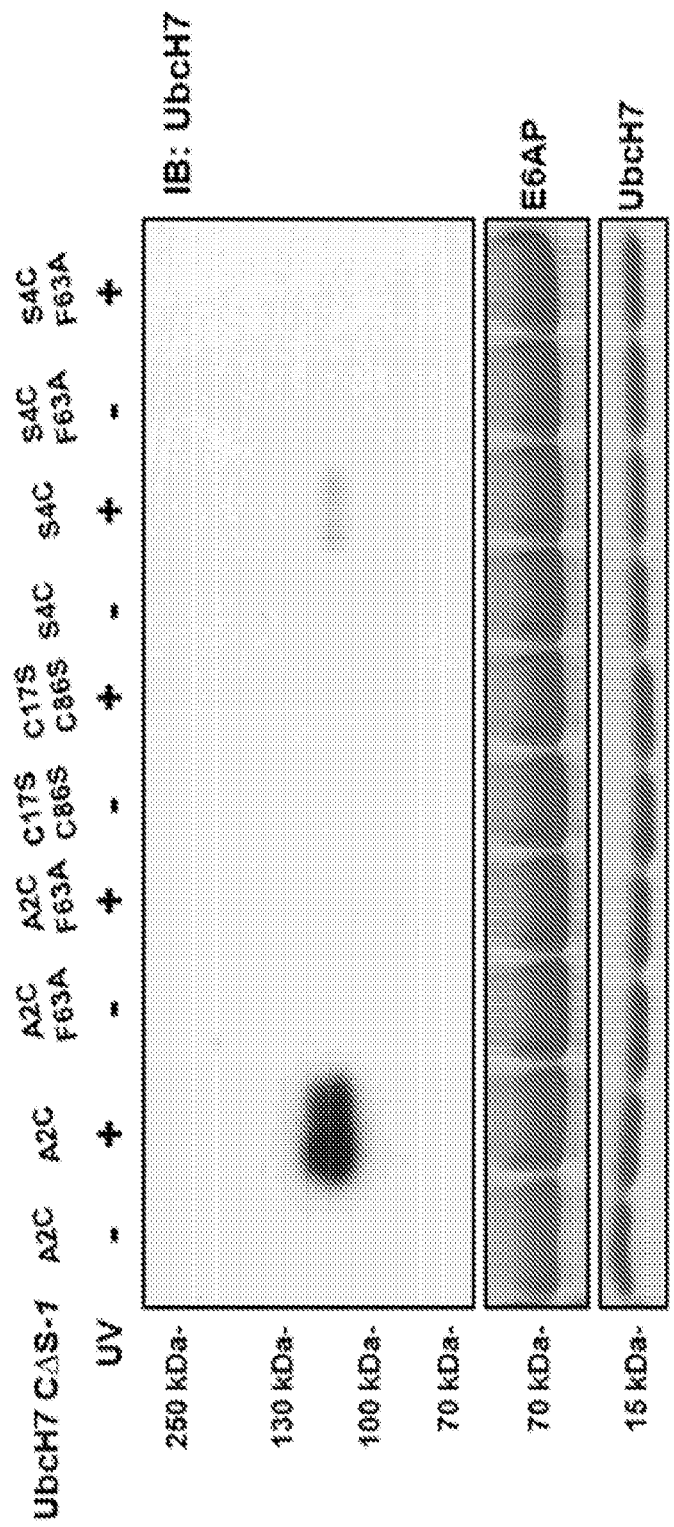
Figure 8A:
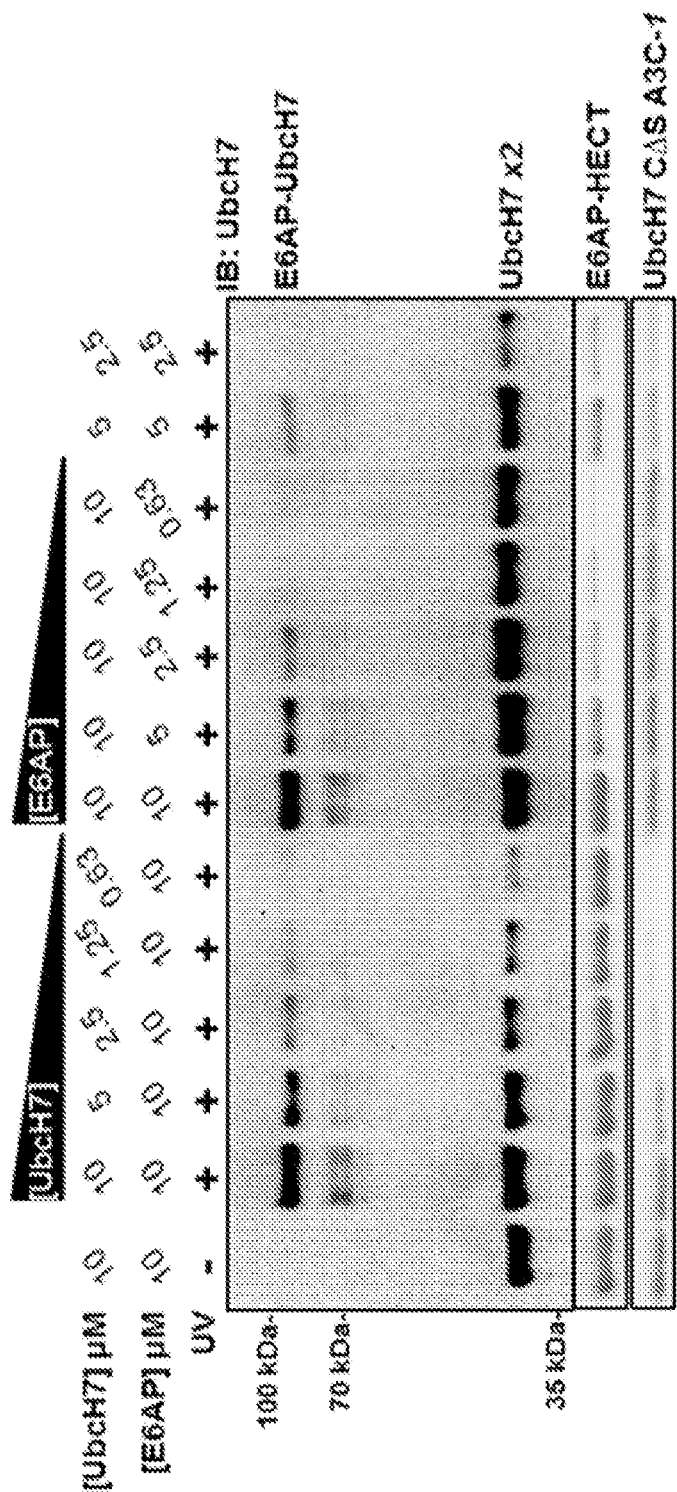
FIGS. 8A-B. UbcH7/E6AP photocrosslinking is dose-dependent. (A.) UbcH7 CΔS A3C-1 and E6AP HECT were mixed in PBS(B) and irradiated at 365 nm for 10 minutes. Reactions were quenched with 6× Laemmli with β-ME. (B.) Crosslinking is also dose-dependent with UbcH7 CΔS-Ub oxyester. E6AP-HECT (10 µM) was mixed with different concentrations of UbcH7 CΔS A3C-1 or UbcH7 CΔS A3C Ub-1 in PBS(B) with 1 mM DTT and irradiated for 10 minutes at 365 nm. Reactions were quenched with 6× Laemmli with β-ME and then boiled at 95° C. for 5 minutes.
Figure 8B:
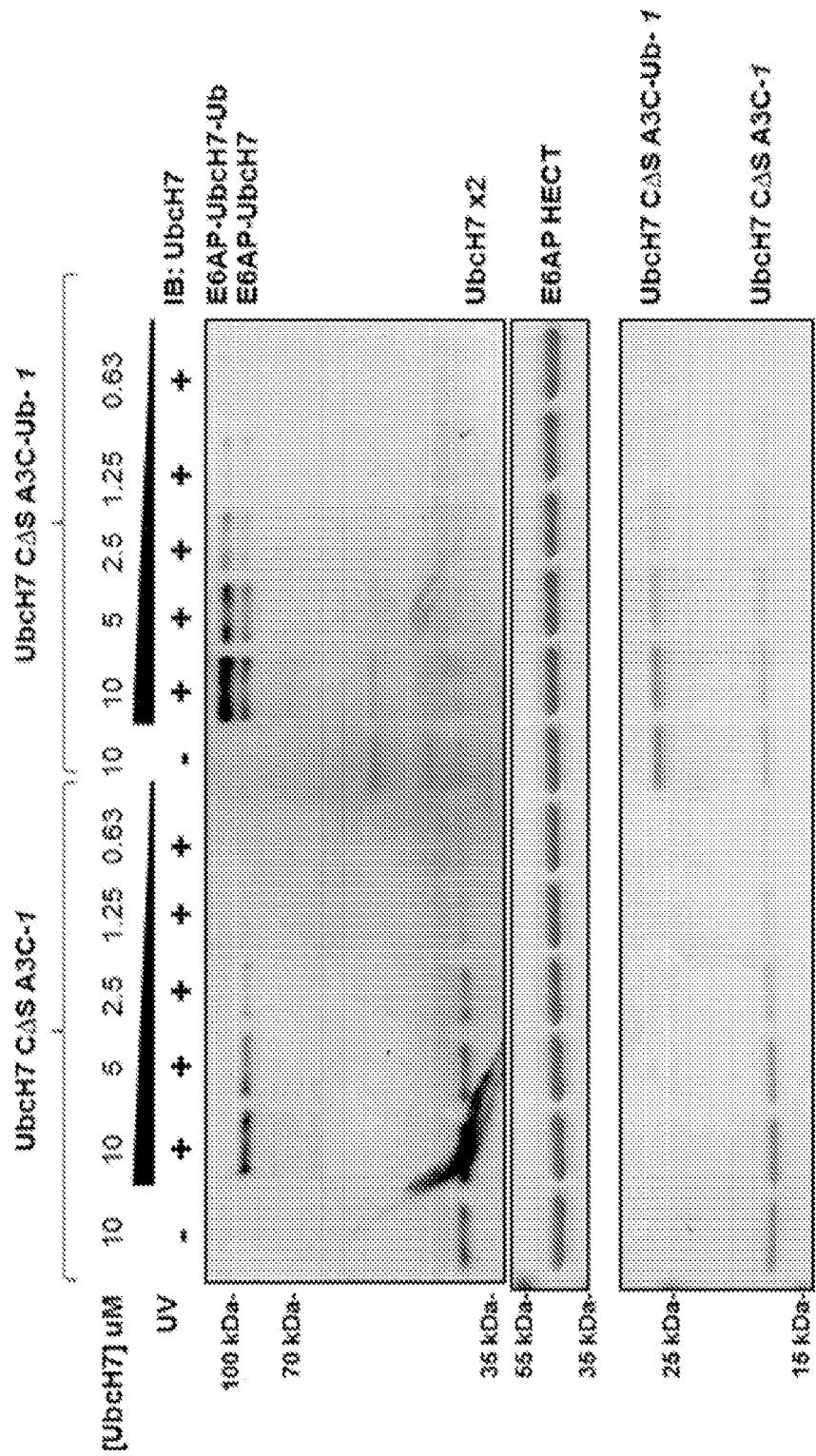
Figure 9:
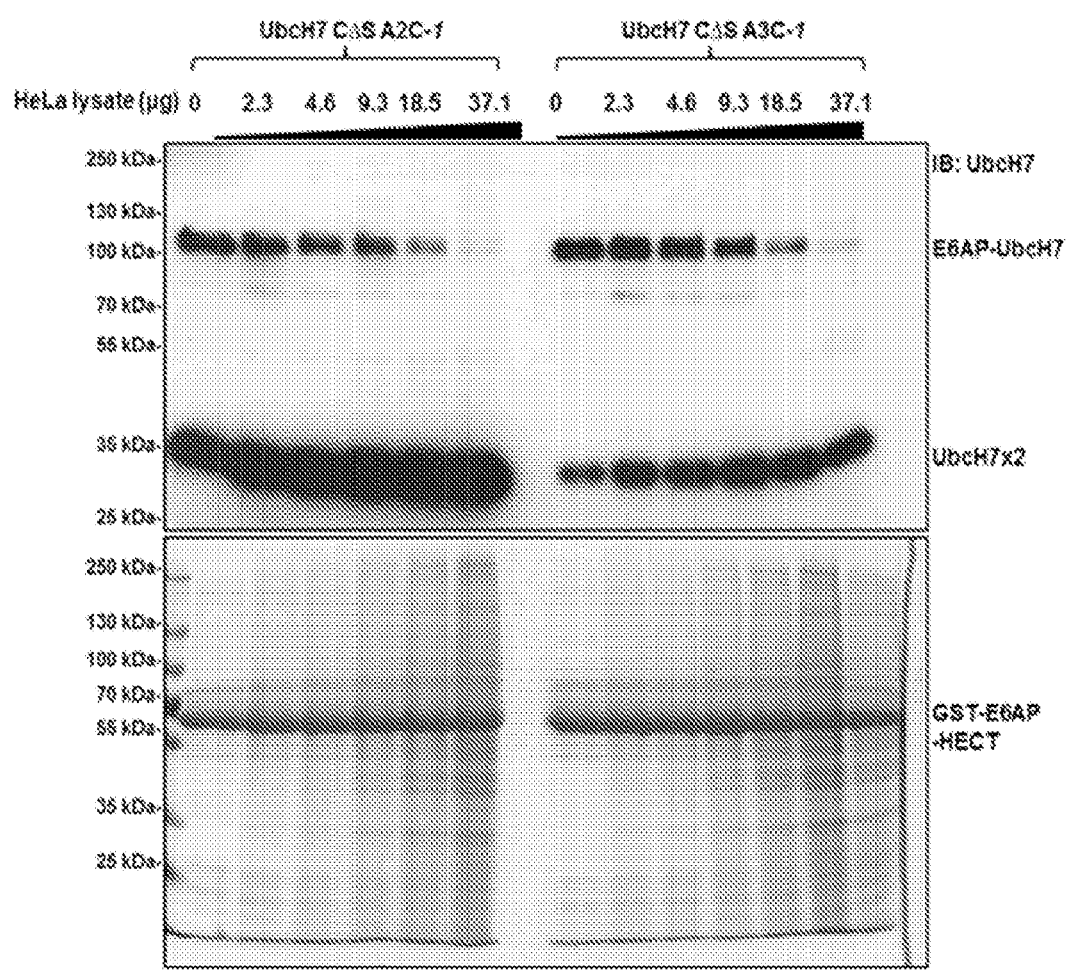
FIG. 9. UbcH7 CΔS-1 selectively photocrosslinks E6AP in the presence of HeLa lysate. GST-E6AP-HECT (10 µM) was mixed with HeLa lysate and UbcH7 CΔS A2C-1 or UbcH7 CΔS A3C-1 (10 µM) in PBS(B) and irradiated at 365 nm for 10 minutes before quenching with 6× Laemmli buffer with β-ME, incubating at room temperature for several minutes, and resolving with SDS-PAGE. Reaction products were visualized either by western blotting (top), or coomassie (bottom).

Different crosslinking efficiencies indicate the high sensitivity and specificity of this technique to the crosslinker location on the UbcH7 surface. Since UbcH7 Phe63 is critical for binding the N-lobe of the E6AP HECT domain, UbcH7 CΔS F63A mutants or their Ub oxyesters bearing 1 or 2 did not crosslink E6AP (FIG. 7). Furthermore, crosslinking is dose-dependent, has specificity that persists in the presence of HeLa cell lysate or detergents, and can be inhibited by wild type UbcH7 in a dose-dependent manner (FIGS. 8-11).

Figure 12A:
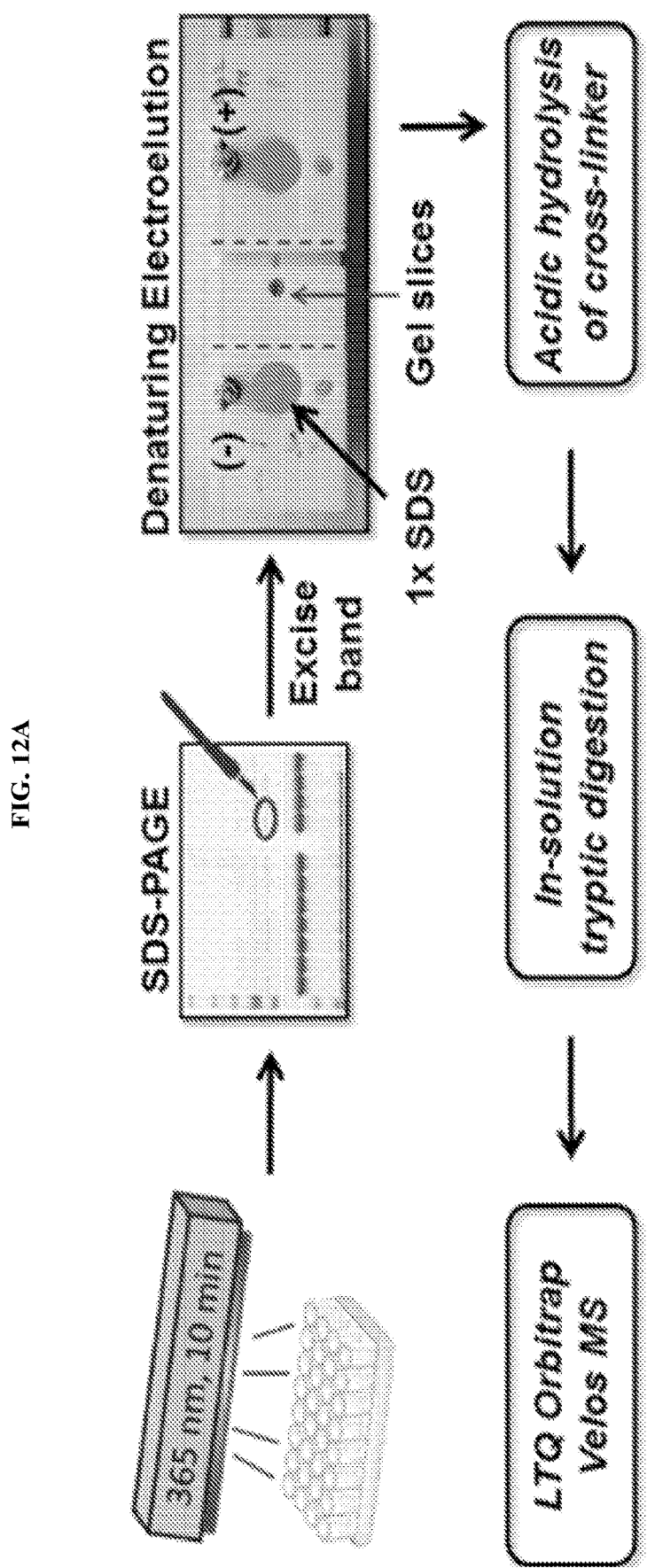
Figures 12D, 12E:
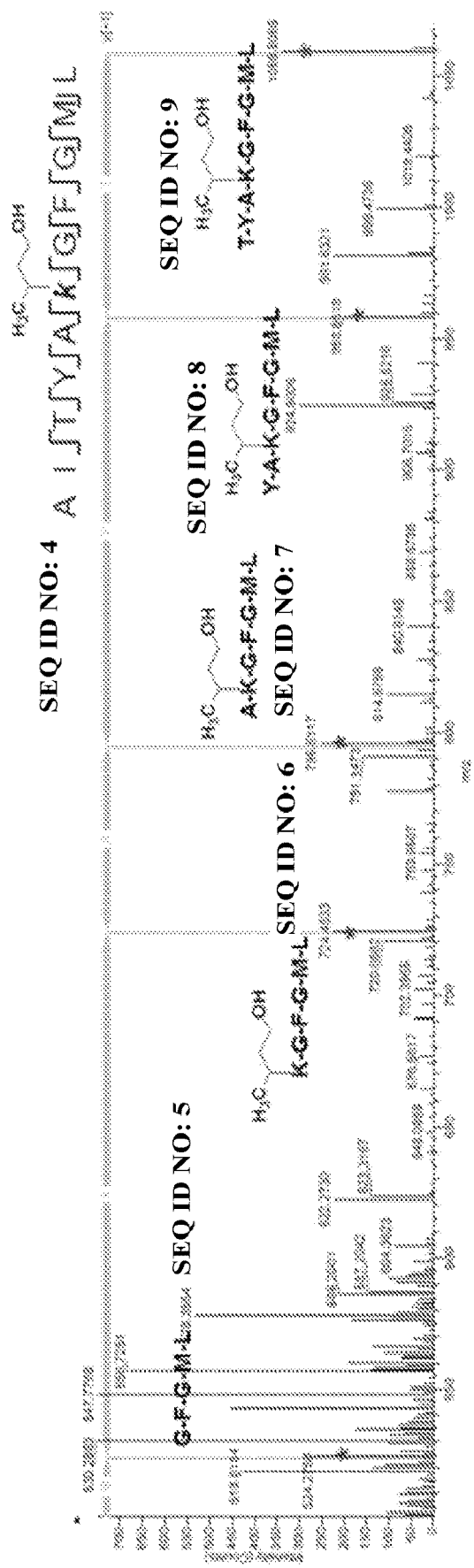
Figure 13:
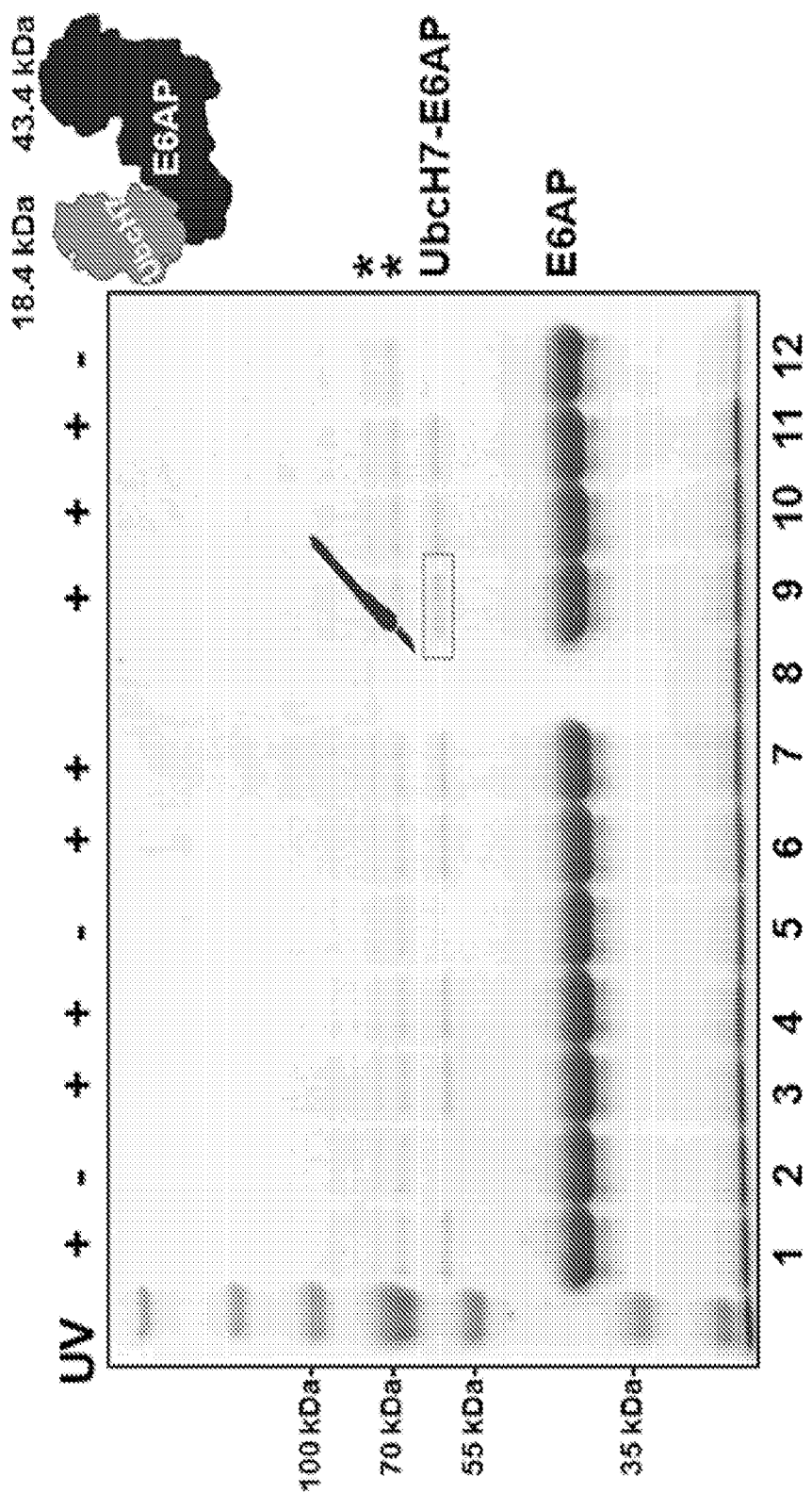
FIG. 13. Representative SDS-PAGE gel from which crosslinked UbcH7-E6AP complex is excised. The photocrosslinked reaction mixture of E6AP (14 μM) and UbcH7 CΔS E93C-2 (14 μM) was resolved using SDS-PAGE, and visualized by incubating gels with InstantBlue (Expedeon) for 10 minutes and then rinsing with $ddH_2O$. The UbcH7-E6AP complex bands were excised and diced to ~1 $mm^2$ pieces (Lanes 1, 3-4, 6-7, 9-11). Lane 12 was loaded with E6AP-HECT without UbcH7CΔS E93C-2. The "*" symbol marks protein impurities from the E6AP-HECT preparation.

To identify the photocrosslinked sites of E6AP, a mass spectrometry protocol was developed. First, UbcH7 and E6AP were photocrosslinked with acid cleavable crosslinker 2 or 3, separated the crosslinked UbcH7-E6AP complex from free UbcH7 and E6AP using SDS-PAGE, and then excised the gel band corresponding to the UbcH7-E6AP complex after minimal coomassie staining of the gel (FIGS. 12-13). An in-gel acid cleavage step proved problematic in experiments conducted during development of embodiments herein; therefore, a customized electroelution apparatus was employed to first extract photocrosslinked protein complexes for subsequent acid-cleavage of crosslinker and proteolytic digestion (FIG. 14) (ref. 15; herein incorporated by reference in its entirety). Following electroelution of the crosslinked complexes into Tris-Glycine-SDS buffer, they were cleaved by acidifying the solution with aqueous HCl to pH 1 and incubating at 55° C. for 120 minutes. It was found that performing the acidification in Tris-Glycine-SDS buffer as opposed to HEPES buffer prevents hydrolysis of the protein backbone (FIG. 12B-C). After this step, the solution was neutralized with aqueous NaOH to pH 9. Finally, protein was precipitated with acetone, digested with trypsin, and then analyzed the peptides with an Orbitrap Velos.

Figure 3A:
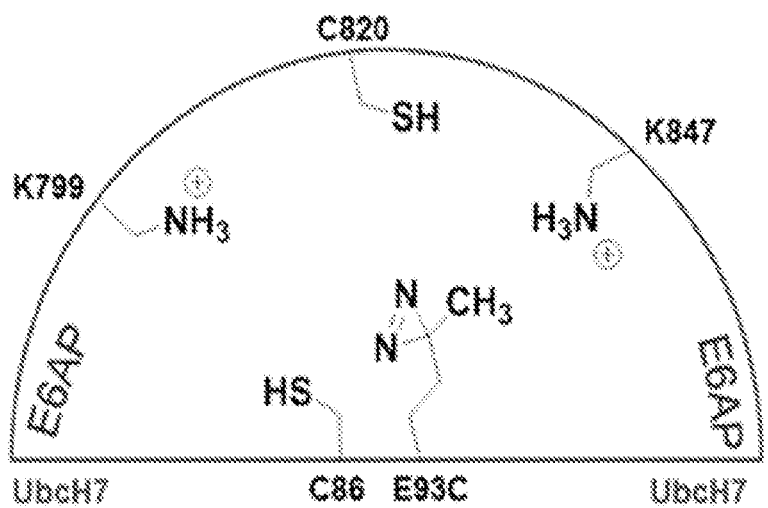
FIGS. 3A-B. E6AP Lys799 and Lys847 modulate the formation of Lys48-linked polyubiquitin chains. A. Schematic representations of residues spatially proximal to UbcH7 E93C. Crosslinking UbcH7 CΔS E93C-2/3 or UbcH7 CΔS E93C-Ub-2/3 interrogates the UbcH7/E6AP catalytic microenvironment. Black E6AP residues were labeled by crosslinkers 2 and 3. E6AP K799 was only labeled by 3 in the experiments with UbcH7 CΔS E93C-Ub oxyester. B. WT UbcH7 (2 µM), E6AP HECT (indicated mutant, 2 µM), Uba1 (0.2 µM), Ub (1500 µM) and ATP (2 mM) were incubated for 60 minutes in 25 mM HEPES pH 7.6, 100 mM NaCl, 4 mM MgCl2 at 37° C. before resolving with SDS-PAGE and analyzing the reaction mixtures with Lys48-linkage specific antibody.
Figure 3A:
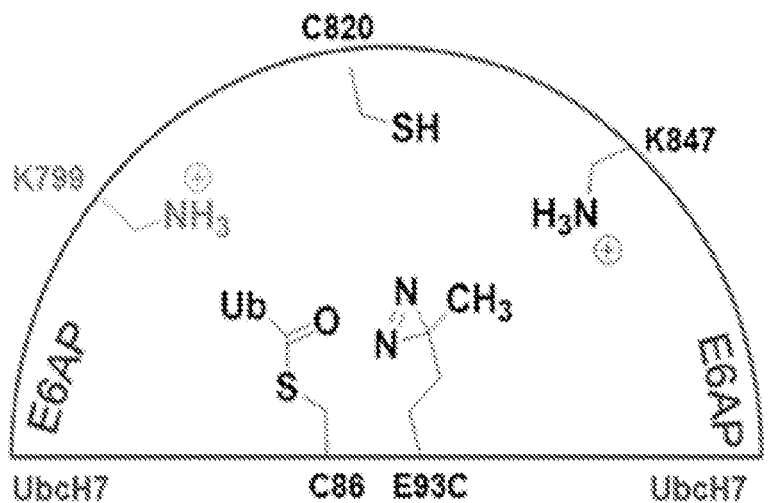

Mass analysis was performed on crosslinking experiments between E6AP HECT and E2 enzyme alone (UbcH7 CΔS E93C-2, UbcH7 CΔS E93C-3), or E2-Ub oxyester (UbcH7 CΔS E93C Ub-2, or UbcH7 CΔS E93C Ub-3; Tables 1-2). UbcH7 was modified at E93C with the sulfamic acid that re-mains following cleavage of crosslinker (+136.98 Da for 2 or 3). Covalent modifications (72.06 Da for 2, 77.09 Da for 3) on E6AP were localized to the HECT domain C-lobe at the catalytic cysteine Cys820, Lys847, and Lys799 (FIG. 12D-E). While no modifications were found on the E6AP N-lobe where the E2 binding site is located, this was not entirely unexpected since crosslinker on UbcH7 E93C is 10-11 Å from the UbcH7 catalytic site which encounters the flexible HECT C-lobe to undergo transthiolation (ref. 16; incorporated by reference in its entirety). Thus, placing the crosslinker on UbcH7 E93C allowed interrogation of the catalytic environment near the E2 and HECT E3 catalytic cysteines (FIG. 3A).

Cys820 is the catalytic cysteine of E6AP located on the HECT C-lobe, and its modification by crosslinker suggests that it approaches the UbcH7 catalytic Cys86. Although the C-terminal Lys847 of E6AP is disordered in X-ray crystal structures, the photocrosslinkers were also able to locate the proximity of this residue to the active site of the E2 enzyme. Furthermore, covalent modification at Lys799 is an interesting finding since inactivating mutations of Angelman syndrome are located just C-terminal to this residue (801KMII804). Overall, this indicated that Lys799 and Lys847 of E6AP are important for enzyme catalysis (ref. 17; herein incorporated by reference in its entirety).

Figure 3B:
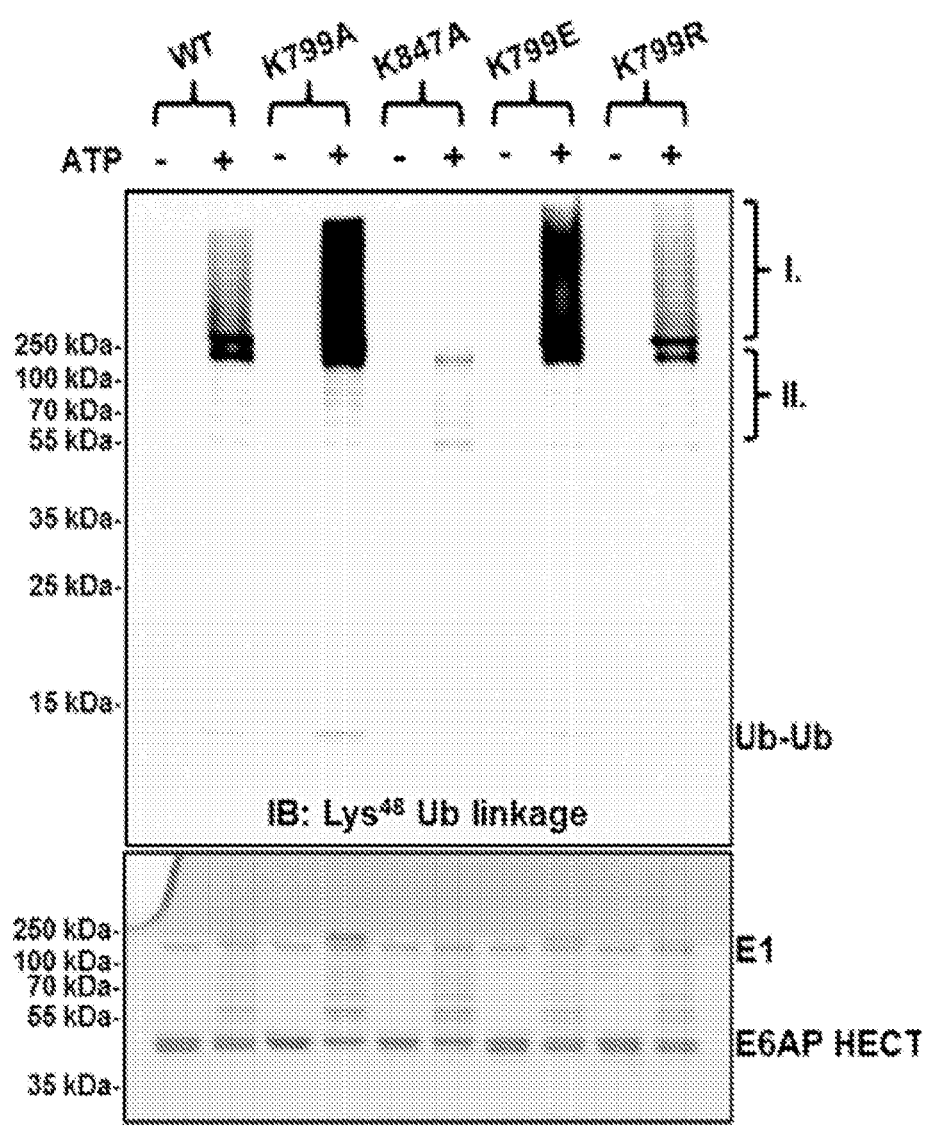
Figure 16:
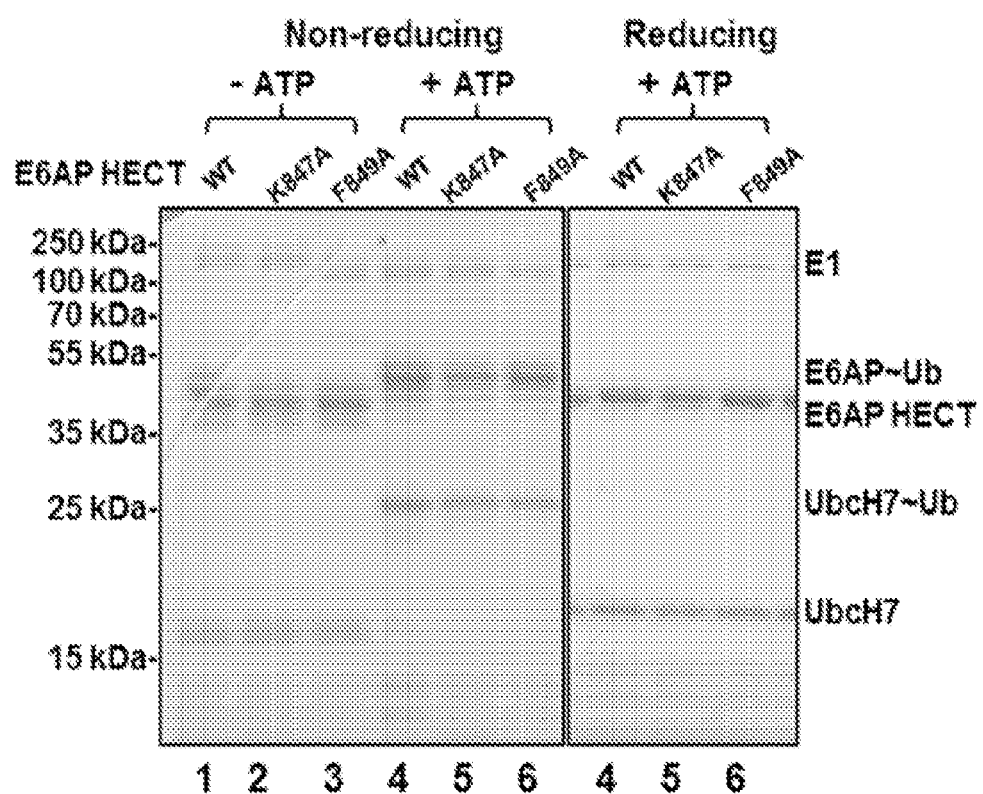
FIG. 16. Isopeptide ligation defective E6AP HECT mutants form E6AP~Ub thioesters. Reactions containing Uba1 (0.2 μM), UbcH7 (2 μM), E6AP (2 μM), ubiquitin (200 μM), with or without ATP (2 mM) were incubated in 25 mM HEPES pH 7.6, 100 mM NaCl, 4 mM $MgCl_2$ for several minutes at room temperature. Reaction mixtures were quenched with 6× Laemmli buffer with or without β-ME, resolved with SDS-PAGE, and visualized with coomassie stain.

Since the catalytic roles of Lys847 or Lys799 have not been previously known, it was investigated how alanine mutations affect the ability of E6AP to assemble Lys48-linked polyubiquitin chains under standard conditions (FIGS. 3B and 12). It was found that the E6AP K847A mutant is deficient in synthesizing Lys48-linked polyubiquitin chains, indicating that Lys847 participates in enzyme catalysis. Moreover, the catalytic activity of E6AP is restored with the E6AP K847R mutant, but not to the same degree with the E6AP K847E mutant (FIG. 15). To verify that the K847A mutation does not affect the folding of E6AP HECT or its ability to bind UbcH7, a photocrosslinking assay was conducted with UbcH7 CΔS E93C-2, which showed that UbcH7 can still efficiently photocrosslink such an E6AP mutant (FIG. 15). Moreover, E6AP HECT K847A retains wild type activity in forming E6AP~Ub thioester (FIG. 16).

Figure 17A:
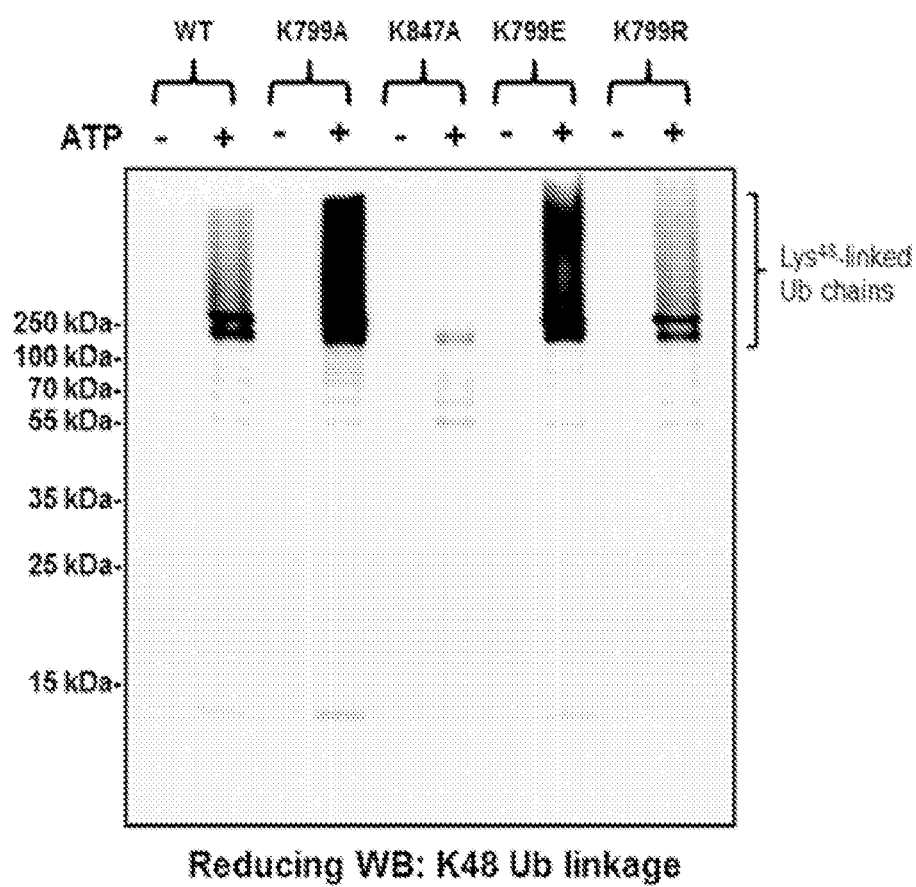
FIGS. 17A-C. E6AP Lys799 influences the production of $Lys^{48}$-linked polyubiquitin chains. Reactions contained Uba1 (0.2 μM), UbcH7 (2 μM), E6AP (2 μM), ubiquitin (150 μM), with or without ATP (2 mM), and were incubated in 25 mM HEPES pH 7.6, 100 mM NaCl, 4 mM $MgCl_2$ for 60 minutes at 37° C. Reactions were quenched with 6× Laemmli with or without β-ME. The "E6AP~Ub" marks the E6AP HECT-Ub thioester. K799 mutants retain the ability to form E6AP HECT~Ub thioesters.
Figure 17B:
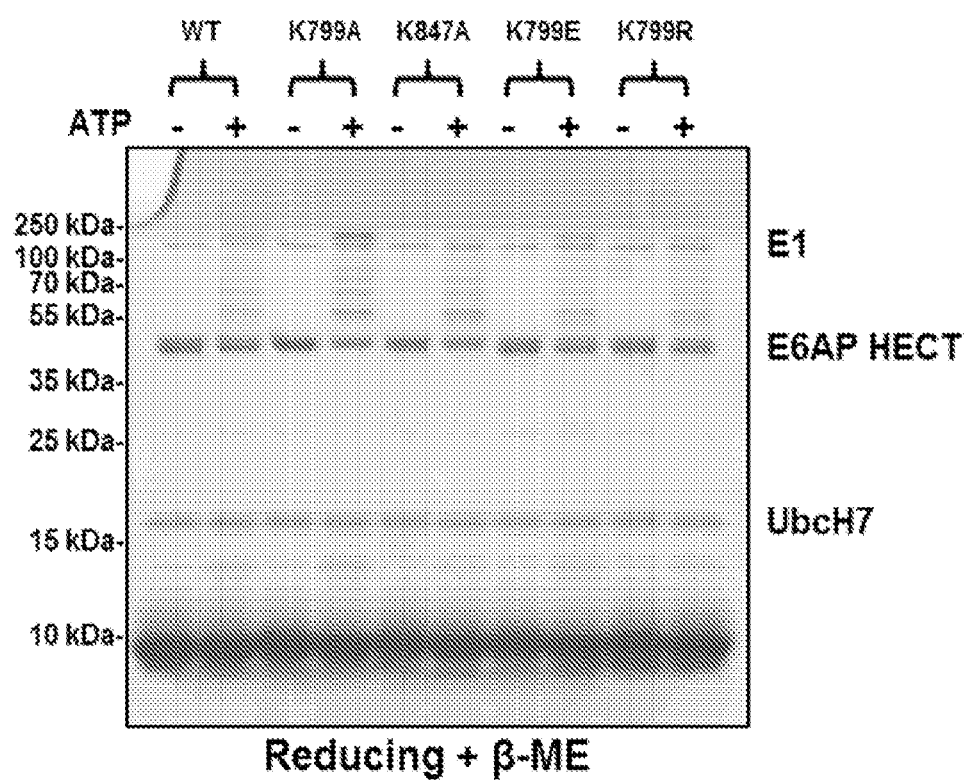
Figure 17C:
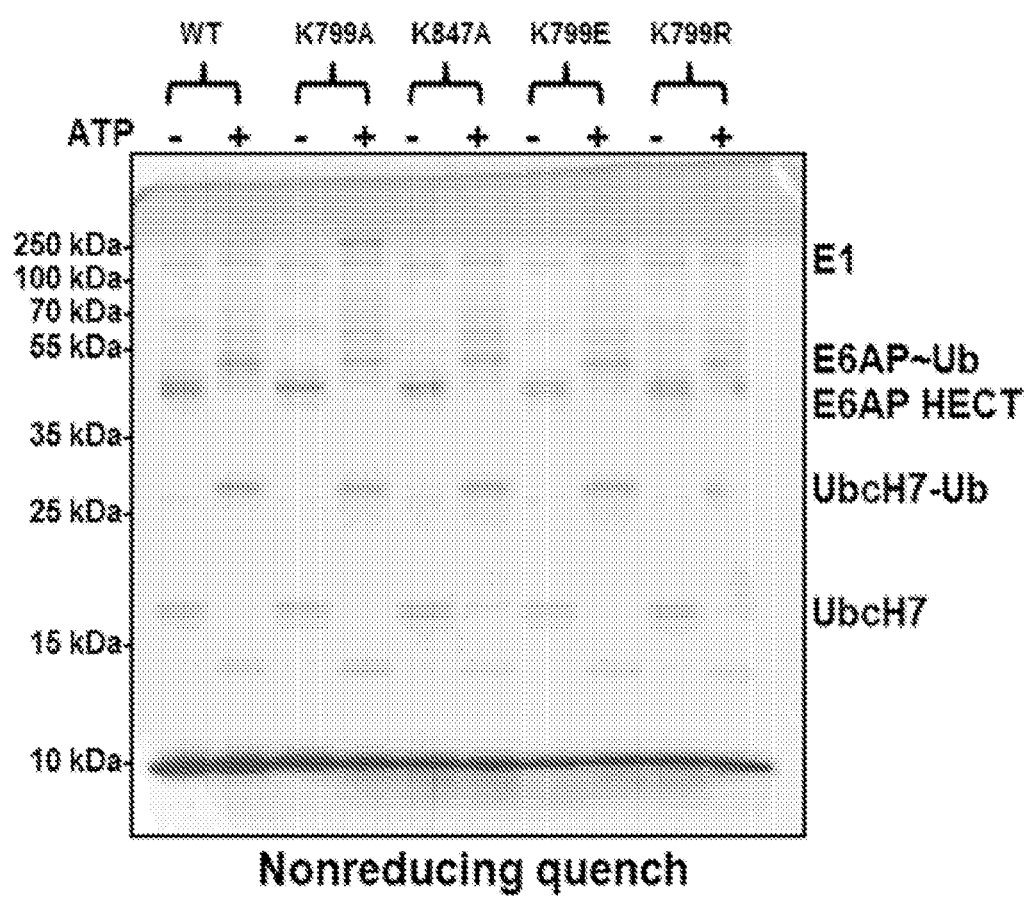
Figure 18:
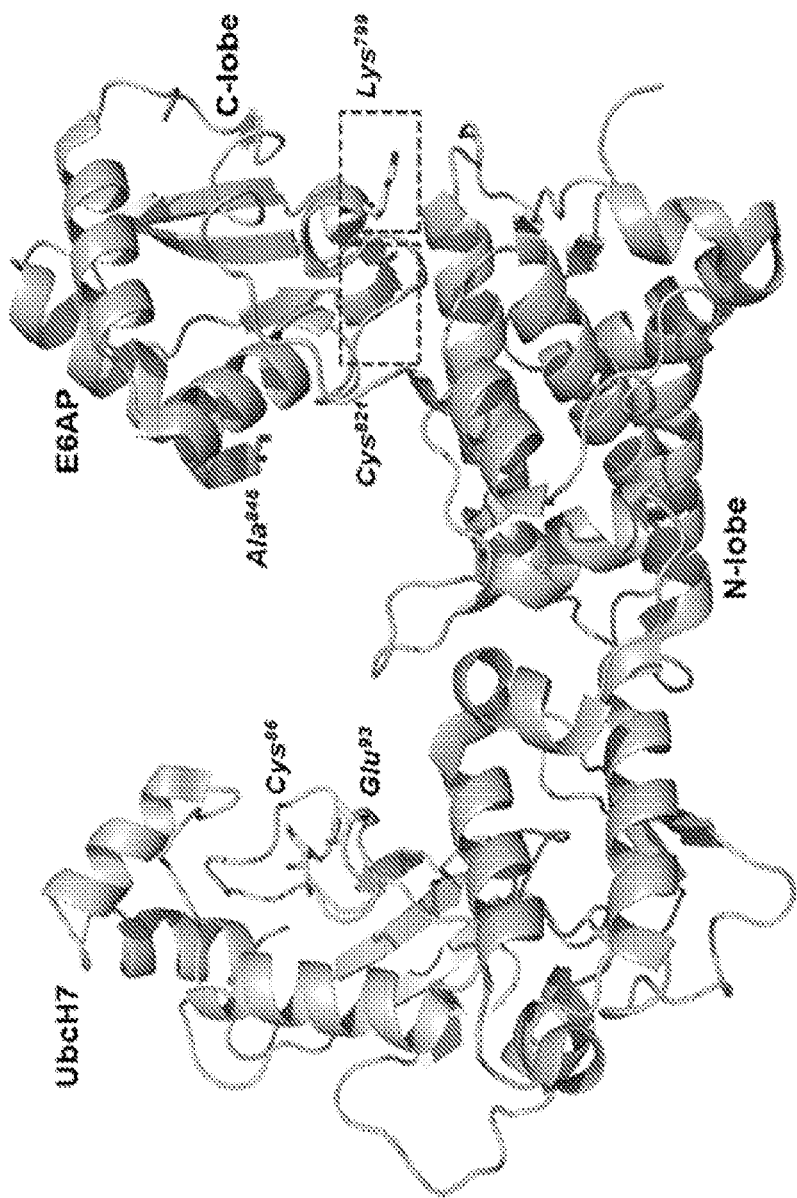
FIG. 18. UbcH7/E6AP HECT co-crystal structure, PDB: 1C4Z. Published by Huang and Pavletich, et al. 1999. The UbcH7 catalytic cysteine $Cys^{86}$ is highlighted. UbcH7 $Glu^{93}$ was mutated to Cys and then equipped with crosslinker 2 or 3. E6AP $Cys^{820}$ and $Lys^{799}$ were modified by crosslinker. E6AP $Lys^{847}$ was also modified but it is disordered in this structure. The last residue of the E6AP C-terminus to appear in this structure is $Ala^{846}$ (colored green). $Lys^{847}$ is immediately C-terminal to this residue.
Figure 19A:
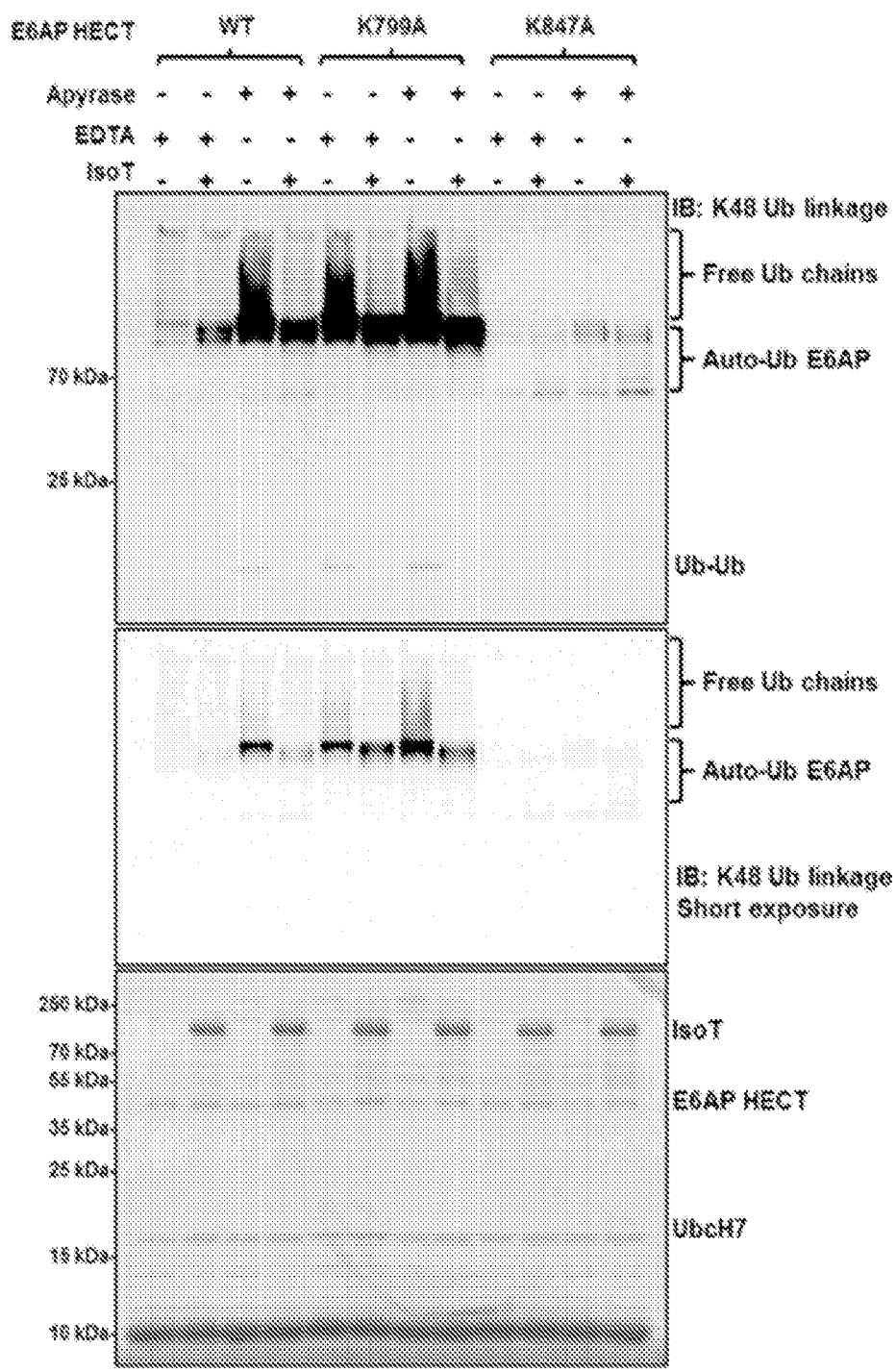
FIGS. 19A-B. For either free polyubiquitin chain formation or autoubiquitination, E6AP HECT has the activity trend: K847A<WT<K799A. (A) Isopeptidase T hydrolyses free polyubiquitin chains, but not those attached to E6AP. Reactions contained Uba1 (0.2 μM), UbcH7 (2 μM), E6AP HECT (2 μM), ubiquitin (100 μM), ATP (1 mM), and were incubated in 25 mM HEPES 7.6, 100 mM NaCl, 4 mM $MgCl_2$ for 30 min at 37° C. ATP turnover was halted by treating solutions with either EDTA (10 mM) or apyrase (0.76 units, Sigma) for 30 min at 37° C. These solutions were then treated with buffer or isopeptidase T (1.2 μM, BostonBiochem) for 30 min at 37° C. Reactions were quenched with 6× Laemmli and β-ME. (B) S5A substrate inhibits the formation of high molecular weight free polyubiquitin chains but presumably not E6AP autoubiquitination. S5a harbors two ubiquitin interaction motifs that normally bind ubiquitin chains in autoubiquitinated E3 ligases, thus bringing S5A in close proximity to the E3 active site. Such binding promotes ubiquitination of S5A. Since E6AP HECT domain is poorly autoubiquitinated, efficient ubiquitination of S5a is not observed. However, a similar E6AP reactivity trend was observed in the presence or absence of the S5a substrate: K847A<WT<K799A. Reactions contained Uba1 (0.2 μM), UbcH7 (2 μM), E6AP HECT (2 μM), ubiquitin (150 μM), ATP (2 mM), +/-S5a (2 μM, BostonBiochem), and were incubated in 25 mM HEPES 7.6, 100 mM NaCl, 4 mM $MgCl_2$ for 40 minutes at 37° C. Reactions were quenched with 6× Laemmli and β-ME.
Figure 19B:
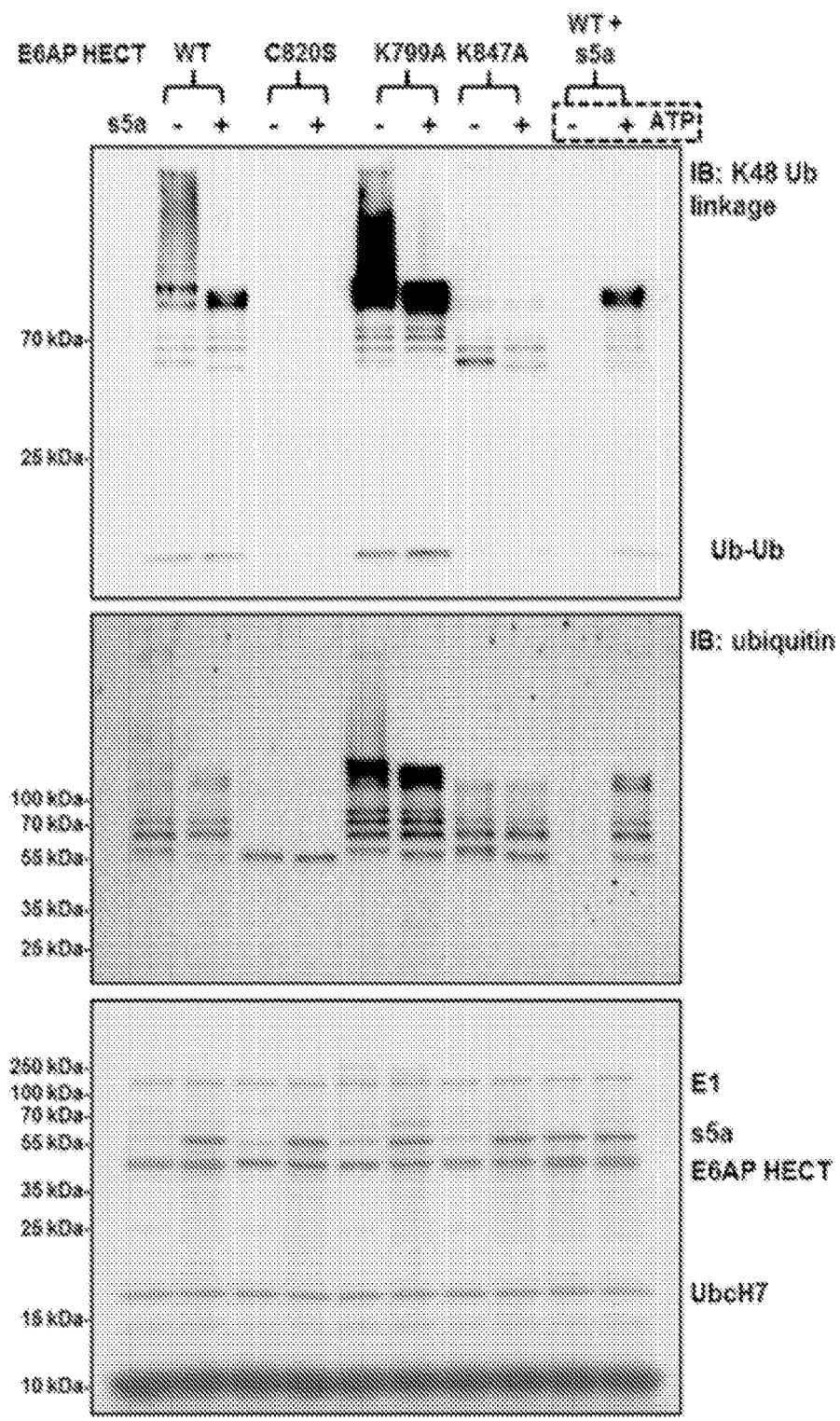
Figure 20:
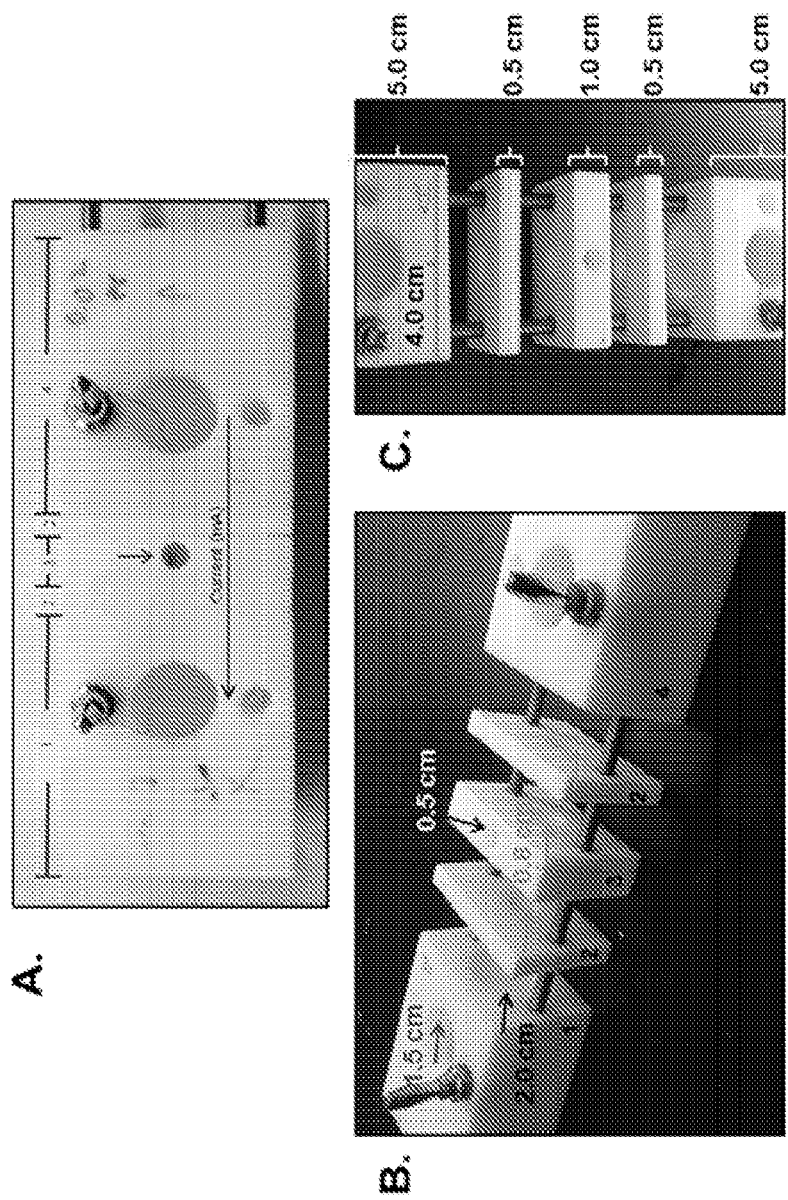
FIG. 20. Denaturing electroelution apparatus. Panel A. This device is based upon a GELFrEE (Gel-Eluted Liquid Fraction Entrapment Electrophoresis) device: 1—Cathode chamber. 2—Connector blocks. 3—Gel/collection chamber. This chamber has a hole (small arrow) that allows collection of electroeluted proteins from the gels after the process. 4—Anode chamber. Panel B. There are internal holes: 0.8 cm for the connectors and the gel/collection chamber and 2.0 cm for the cathode and anode chambers that allow buffer to pass between chambers. At the top of the gel/collection chamber is a 0.5 cm hole. 1.5 cm holes are at the top of the cathode and anode chambers to allow filling with buffer. 3.5 kDa MWCO membranes are between the connectors and the gel/collection chamber to keep protein in the collection chamber. Panel C. Dimensions of the blocks are given: cathode and anode chambers are 5.0 cm wide, connector blocks are 0.5 cm wide, and gel/collection chamber is 1.0 cm wide. The device is assembled as in (Panel A) and secured with screws and nuts to avoid leaks. This device has been adapted for electroelution.

Unexpectedly, E6AP K799A and K799E mutants were more active at producing Lys48-linked polyubiquitin chains than wild type E6AP or its K799R mutant (FIGS. 3B and 17-18). Taken together, these data show that photocrosslinker 2 and its deuterated analogue 3 are useful for scanning the E2/E3 interface to identify catalytically relevant residues on E3 ubiquitin ligases.

Example 4

```
                       Protein Sequences

Underlined residues remain from the GST tag and are not part
of the native protein sequence. E6AP (UBE3A). (SEQ ID NO: 1)
GSTMEQKLISEEDLQGQQLNPYL
         510        520        530        540        550
RLKVRRDHII DDALVRLEMI AMENPADLKK QLYVEFEGEQ GVDEGGVSKE 560        570        580        590        600
FFQLVVEEIF NPDIGMFTYD ESTKLFWFNP SSFETEGQFT LIGIVLGLAI 610        620        630        640        650
YNNCILDVHF PMVVYRKLMG KKGTFRDLGD SHPVLYQSLK DLLEYEGNVE 660        670        680        690        700
DDMMITFQIS QTDLFGNPMM YDLKENGDKI PITNENRKEF VNLYSDYILN 710        720        730 v740       750
KSVEKQFKAF RRGFHMVTNE SPLKYLFRPE EIELLICGSR NLDFQALEET 760        770        780        790        800
TEYDGGYTRD SVLIREFWEI VHSFTDEQKR LFLQFTTGTD RAPVGGLGKL 810        820        830        840        850
KMIIAKNGPD TERLPTSHTC FNVLLLPEYS SKEKLKERLL KAITYAKGFG

ML

UbCH7 (UBE2L3) (SEQ. ID NO: 2)
GPLGS
          10         20         30         40         50
MAASRRLMKE LEEIRKCGMK NFRNIQVDEA NLLTWQGLIV PDNPPYDKGA 60         70         80         90        100
FRIEINFPAE YPFKPPKITF KTKIYHPNID EKGQVCLPVI SAENWKPATK
```

```
                110        120        130        140        150
         TDQVIQSLIA LVNDPQPEHP LRADLAEEYS KDRKKFCKNA EEFTKKYGEK

RPVD

Ubiquitin (human) (SEQ ID NO: 3)
                 10         20         30         40         50
         MQIFVKTLTG KTITLEVEPS DTIENVKAKI QDKEGIPPDQ QRLIFAGKQL 60         70
         EDGRTLSDYN IQKESTLHLV LRLRGG
```

REFERENCES

The following references, some of which are cited above by number, are herein incorporated by reference in their entireties.

(1) Varshavsky, A. (2012) The ubiquitin system, an immense realm. Ann. Rev. Biochem. 81, 167.
(2) Scheffner, M.; Nuber, U.; Huibregtse, J. M. (1995) Protein ubiquitination involving an E1-E2-E3 enzyme ubiquitin thioester cascade. Nature 373, 81.
(3) Kishino, T.; Lalande, M.; Wagstaff, J. (1997) UBE3A/E6-AP mutations cause Angelman syndrome. Nat. Genetics 15, 70.
(4) Scheffner, M.; Huibregtse, J. M.; Vierstra, R. D.; Howley, P. M. (1993) The HPV-16 E6 and E6-AP complex functions as a ubiquitin-protein ligase in the ubiquitination of p53. Cell 75, 495.
(5) Nuber, U.; Schwarz, S.; Kaiser, P.; Schneider, R.; Scheffner, M. (1996) Cloning of human ubiquitin-conjugating enzymes UbcH6 and UbcH7 (E2-F1) and characterization of their interactions with E6-AP and RSP5. J. Biol. Chem. 271, 2795.
(6) Purbeck, C.; Eletr, Z. M.; Kuhlman, B. (2010) Kinetics of the transfer of ubiquitin from UbcH7 to E6AP. Biochemistry 49, 1361.
(7) Ronchi, V. P.; Klein, J. M.; Haas, A. L. (2013) E6AP/UBE3A ubiquitin ligase harbors two E2-ubiquitin binding sites. J. Biol. Chem. 288, 10349.
(8) Ronchi, V. P.; Klein, J. M.; Edwards, D. J.; Haas, A. L. (2014) The active form of E6-associated protein (E6AP)/UBE3A ubiquitin ligase is an oligomer. J. Biol. Chem. 289, 1033.
(9) MacKinnon, A. L.; Garrison, J. L.; Hegde, R. S.; Taunton, J. (2007) Photo-leucine incorporation reveals the target of a cyclodepsipeptide inhibitor of cotranslational translocation. J. Am. Chem. Soc. 129, 14560.
(10) Yang, B.; Wu, Y-J.; Zhu, M.; Fan, S-B.; Lin, J.; Zhang, K.; Li, S.; Chi, H.; Li, Y-X.; Chen, H-F.; Luo, S-K.; Ding, Y-H.; Wang, L-H.; Hao, Z.; Xiu, L-Y.; Chen, S.; Ye, K.; He, S-M.; Dong, M-Q. (2012) Identification of crosslinked peptides from complex samples. Nat. Methods 9, 904.
(11) Chou, C. J.; Uprety, R.; Davis, L.; Chin, J. W.; Deiters, A. (2011) Genetically encoding an aliphatic diazirine for protein photocrosslinking. Chem. Sci. 2, 480.
(12) An, H.; Statsyuk, A. V. (2013) Development of activity-based probes for ubiquitin and ubiquitin-like protein signaling pathways. J. Am. Chem. Soc. 135, 16948.
(13) Huang, L.; Kinnucan, E.; Wang, G. L.; Beaudenon, S.; Howley, P. M.; Huibregtse, J. M.; Pavletich, N. P. (1999) Structure of an E6AP-UbcH7 complex: insights into ubiquitination by the E2-E3 enzyme cascade. Science 286, 1321.
(14) Eletr, Z. M.; Kuhlman, B. (2007) Sequence determinants of E2-E6AP binding affinity and specificity. J. Mol. Biol. 369, 419.
(15) Tran, J. C.; Doucette, A. A. (2008) Gel-eluted liquid fraction entrapment electrophoresis: an electrophoretic method for broad molecular weight range proteome separation. Anal. Chem. 80, 1568.
(16) Verdecia, M. A.; Joazeiro, C. A.; Wells, N. J.; Ferrer, J. L.; Bowman, M. E.; Hunter, T.; Noel, J. P. (2003) Conformational flexibility underlies ubiquitin ligation mediated by the WWP1 HECT domain E3 ligase. Mol. Cell 11, 249.
(17) Cooper, E. M.; Hudson, A. W.; Amos, J.; Wagstaff, J.; Howley, P. M. (2004) Biochemical analysis of Angelman syndrome-associated mutations in the E3 ubiquitin ligase E6-associated protein. J. Biol. Chem. 279, 41208.
(18) Brown, Z. Z.; Muller, M. M.; Jain, S. U.; Allis, C. D.; Lewis, P. W.; Muir, T. W. (2014) Strategy for "detoxification" of a cancer-derived histone mutant based on mapping its interaction with the methyltransferase PRC2. J. Am. Chem. Soc. 136, 13498.

The invention claimed is:

1. A composition comprising a photocrosslinkable compound of Formula I:

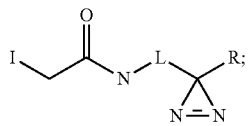

(Formula I)

wherein L is selected from a direct covalent bond, alkyl, substitutied alkyl, heteroalkyl, substituted heteroalkyl, and/or a cleavable moiety; wherein L does not contain an aromatic ring; and wherein R is selected from H, alkyl, substitutied alkyl, heteroalkyl, substituted heteroalkyl.

2. The composition of claim 1, wherein the compound comprises Formula II:

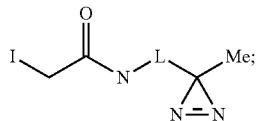

(Formula II)

wherein L is selected from a direct covalent bond, alkyl, substitutied alkyl, heteroalkyl, substituted heteroalkyl, and/or a cleavable moiety.

3. The composition of claim 2, wherein the compound comprises Formula III:

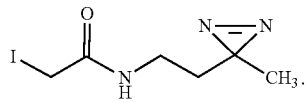

Formula III)

4. The composition of claim 2, wherein the L comprises a cleavable moiety.

5. The composition of claim 4, wherein the cleavable moiety is N-acylsulfamate.

6. The composition of claim 5, wherein the compound comprises Formula IV:

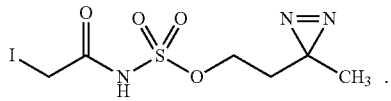

(Formula IV)

7. The composition of claim 2, wherein the compound is isotopically-labelled at one or more positions.

8. The composition of claim 7, wherein the compound is isotopically-labelled at one or more positions with a non-natural abundance of stable heavy isotopes.

9. The composition of claim 8, wherein one or more hydrogen positons on the compound are deuterium.

10. The composition of claim 9, wherein the compound comprises Formula V:

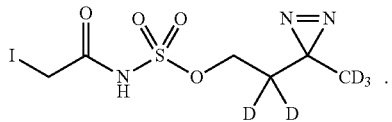

(Formula V)

11. The composition of claim 1, wherein L comprises —(SO₂)O(CH₂)₁₋₁₀—.

12. The composition of claim 11, wherein R is methyl, ethyl, CD₃, trifluoromethyl, or trifluoroethyl.

13. A composition comprising a photocrosslinkable compound of Formula I:

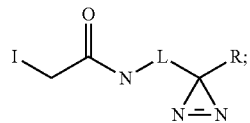

(Formula I)

wherein L is selected from a direct covalent bond, alkyl, substitutied alkyl, heteroalkyl, substituted heteroalkyl, and/or a cleavable moiety; and wherein R is selected from H, alkyl, substitutied alkyl, heteroalkyl, substituted heteroalkyl;

wherein R is not trifluoromethyl.

14. The composition of claim 13, wherein the L comprises a cleavable moiety.

15. The composition of claim 14, wherein the cleavable moiety is N-acylsulfamate.

16. The composition of claim 15, wherein L comprises —(SO₂)O(CH₂)₁₋₁₀—.

17. The composition of claim 16, wherein R is methyl, ethyl, CD₃, or trifluoroethyl.

18. The composition of claim 13, wherein the compound is isotopically-labelled at one or more positions.

19. The composition of claim 18, wherein the compound is isotopically-labelled at one or more positions with a non-natural abundance of stable heavy isotopes.

20. The composition of claim 19, wherein one or more hydrogen positions on the compound are deuterium.

* * * * *

SEQUENCE LISTING

```
<160> NUMBER OF SEQ ID NOS: 12

<210> SEQ ID NO 1
<211> LENGTH: 375
<212> TYPE: PRT
<213> ORGANISM: Artificial sequence
<220> FEATURE:
<223> OTHER INFORMATION: Synthetic peptide

<400> SEQUENCE: 1

Gly Ser Thr Met Glu Gln Lys Leu Ile Ser Glu Glu Asp Leu Gln Gly
```

-continued

```
1               5                   10                  15
Gln Gln Leu Asn Pro Tyr Leu Arg Leu Lys Val Arg Arg Asp His Ile
                20                  25                  30
Ile Asp Asp Ala Leu Val Arg Leu Glu Met Ile Ala Met Glu Asn Pro
                35                  40                  45
Ala Asp Leu Lys Lys Gln Leu Tyr Val Glu Phe Glu Gly Glu Gln Gly
                50                  55                  60
Val Asp Glu Gly Gly Val Ser Lys Glu Phe Phe Gln Leu Val Val Glu
65                  70                  75                  80
Glu Ile Phe Asn Pro Asp Ile Gly Met Phe Thr Tyr Asp Glu Ser Thr
                    85                  90                  95
Lys Leu Phe Trp Phe Asn Pro Ser Ser Phe Glu Thr Glu Gly Gln Phe
                100                 105                 110
Thr Leu Ile Gly Ile Val Leu Gly Leu Ala Ile Tyr Asn Asn Cys Ile
                115                 120                 125
Leu Asp Val His Phe Pro Met Val Val Tyr Arg Lys Leu Met Gly Lys
                130                 135                 140
Lys Gly Thr Phe Arg Asp Leu Gly Asp Ser His Pro Val Leu Tyr Gln
145                 150                 155                 160
Ser Leu Lys Asp Leu Leu Glu Tyr Glu Gly Asn Val Glu Asp Asp Met
                165                 170                 175
Met Ile Thr Phe Gln Ile Ser Gln Thr Asp Leu Phe Gly Asn Pro Met
                180                 185                 190
Met Tyr Asp Leu Lys Glu Asn Gly Asp Lys Ile Pro Ile Thr Asn Glu
                195                 200                 205
Asn Arg Lys Glu Phe Val Asn Leu Tyr Ser Asp Tyr Ile Leu Asn Lys
                210                 215                 220
Ser Val Glu Lys Gln Phe Lys Ala Phe Arg Arg Gly Phe His Met Val
225                 230                 235                 240
Thr Asn Glu Ser Pro Leu Lys Tyr Leu Phe Arg Pro Glu Glu Ile Glu
                245                 250                 255
Leu Leu Ile Cys Gly Ser Arg Asn Leu Asp Phe Gln Ala Leu Glu Glu
                260                 265                 270
Thr Thr Glu Tyr Asp Gly Gly Tyr Thr Arg Asp Ser Val Leu Ile Arg
                275                 280                 285
Glu Phe Trp Glu Ile Val His Ser Phe Thr Asp Glu Gln Lys Arg Leu
                290                 295                 300
Phe Leu Gln Phe Thr Thr Gly Thr Asp Arg Ala Pro Val Gly Gly Leu
305                 310                 315                 320
Gly Lys Leu Lys Met Ile Ile Ala Lys Asn Gly Pro Asp Thr Glu Arg
                325                 330                 335
Leu Pro Thr Ser His Thr Cys Phe Asn Val Leu Leu Leu Pro Glu Tyr
                340                 345                 350
Ser Ser Lys Glu Lys Leu Lys Glu Arg Leu Leu Lys Ala Ile Thr Tyr
                355                 360                 365
Ala Lys Gly Phe Gly Met Leu
370                 375
```

<210> SEQ ID NO 2
<211> LENGTH: 159
<212> TYPE: PRT
<213> ORGANISM: Artificial sequence
<220> FEATURE:
<223> OTHER INFORMATION: Synthetic peptide

<400> SEQUENCE: 2

Gly Pro Leu Gly Ser Met Ala Ala Ser Arg Arg Leu Met Lys Glu Leu
1               5                   10                  15

Glu Glu Ile Arg Lys Cys Gly Met Lys Asn Phe Arg Asn Ile Gln Val
            20                  25                  30

Asp Glu Ala Asn Leu Leu Thr Trp Gln Gly Leu Ile Val Pro Asp Asn
        35                  40                  45

Pro Pro Tyr Asp Lys Gly Ala Phe Arg Ile Glu Ile Asn Phe Pro Ala
    50                  55                  60

Glu Tyr Pro Phe Lys Pro Lys Ile Thr Phe Lys Thr Lys Ile Tyr
65                  70                  75                  80

His Pro Asn Ile Asp Glu Lys Gly Gln Val Cys Leu Pro Val Ile Ser
                85                  90                  95

Ala Glu Asn Trp Lys Pro Ala Thr Lys Thr Asp Gln Val Ile Gln Ser
            100                 105                 110

Leu Ile Ala Leu Val Asn Asp Pro Gln Pro Glu His Pro Leu Arg Ala
        115                 120                 125

Asp Leu Ala Glu Glu Tyr Ser Lys Asp Arg Lys Lys Phe Cys Lys Asn
    130                 135                 140

Ala Glu Glu Phe Thr Lys Lys Tyr Gly Glu Lys Arg Pro Val Asp
145                 150                 155

<210> SEQ ID NO 3
<211> LENGTH: 76
<212> TYPE: PRT
<213> ORGANISM: Homo sapiens

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Ala Ile Thr Tyr Ala Lys Gly Phe Gly Met Leu
1               5                   10

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Gly Phe Gly Met Leu 1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Lys Gly Phe Gly Met Leu
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Ala Lys Gly Phe Gly Met Leu
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Tyr Ala Lys Gly Phe Gly Met Leu
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Thr Tyr Ala Lys Gly Phe Gly Met Leu
1               5

<210> SEQ ID NO 10
<211> LENGTH: 62
<212> TYPE: PRT
<213> ORGANISM: Artificial sequence
<220> FEATURE:
<223> OTHER INFORMATION: Synthetic peptide

<400> SEQUENCE: 10

Arg Ala Pro Val Gly Gly Leu Gly Lys Leu Lys Met Ile Ile Ala Lys
1               5                   10                  15

Asn Gly Pro Asp Thr Glu Arg Leu Pro Thr Ser His Thr Cys Phe Asn
                20                  25                  30

Val Leu Leu Leu Pro Glu Tyr Ser Ser Lys Glu Lys Leu Lys Glu Arg
            35                  40                  45

Leu Leu Lys Ala Ile Thr Tyr Ala Lys Gly Phe Gly Met Leu
        50                  55                  60

<210> SEQ ID NO 11
<211> LENGTH: 154

```
<212> TYPE: PRT
<213> ORGANISM: Artificial sequence
<220> FEATURE:
<223> OTHER INFORMATION: Synthetic peptide

<400> SEQUENCE: 11

Met Ala Ala Ser Arg Arg Leu Met Lys Glu Leu Glu Glu Ile Arg Lys
1               5                   10                  15

Cys Gly Met Lys Asn Phe Arg Asn Ile Gln Val Asp Glu Ala Asn Leu
            20                  25                  30

Leu Thr Trp Gln Gly Leu Ile Val Pro Asp Asn Pro Pro Tyr Asp Lys
        35                  40                  45

Gly Ala Phe Arg Ile Glu Ile Asn Phe Pro Ala Glu Tyr Pro Phe Lys
    50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Leu Val
            100                 105                 110

Asn Asp Pro Gln Pro Glu His Pro Leu Arg Ala Asp Leu Ala Glu Glu
        115                 120                 125

Tyr Ser Lys Asp Arg Lys Lys Phe Cys Lys Asn Ala Glu Glu Phe Thr
    130                 135                 140

Lys Lys Tyr Gly Glu Lys Arg Pro Val Asp
145                 150

<210> SEQ ID NO 12
<211> LENGTH: 361
<212> TYPE: PRT
<213> ORGANISM: Artificial sequence
<220> FEATURE:
<223> OTHER INFORMATION: Synthetic peptide

<400> SEQUENCE: 12

Gln Gly Gln Gln Leu Asn Pro Tyr Leu Arg Leu Lys Val Arg Arg Asp
1               5                   10                  15

His Ile Ile Asp Asp Ala Leu Val Arg Leu Glu Met Ile Ala Met Glu
            20                  25                  30

Asn Pro Ala Asp Leu Lys Lys Gln Leu Tyr Val Glu Phe Glu Gly Glu
        35                  40                  45

Gln Gly Val Asp Glu Gly Gly Val Ser Lys Glu Phe Phe Gln Leu Val
    50                  55                  60

Val Glu Glu Ile Phe Asn Pro Asp Ile Gly Met Phe Thr Tyr Asp Glu
65                  70                  75                  80

Ser Thr Lys Leu Phe Trp Phe Asn Pro Ser Ser Phe Glu Thr Glu Gly
                85                  90                  95

Gln Phe Thr Leu Ile Gly Ile Val Leu Gly Leu Ala Ile Tyr Asn Asn
            100                 105                 110

Cys Ile Leu Asp Val His Phe Pro Met Val Val Tyr Arg Lys Leu Met
        115                 120                 125

Gly Lys Lys Gly Thr Phe Arg Asp Leu Gly Asp Ser His Pro Val Leu
    130                 135                 140

Tyr Gln Ser Leu Lys Asp Leu Leu Glu Tyr Glu Gly Asn Val Glu Asp
145                 150                 155                 160

Asp Met Met Ile Thr Phe Gln Ile Ser Gln Thr Asp Leu Phe Gly Asn
                165                 170                 175
```

```
Pro Met Met Tyr Asp Leu Lys Glu Asn Gly Asp Lys Ile Pro Ile Thr
            180                 185                 190

Asn Glu Asn Arg Lys Glu Phe Val Asn Leu Tyr Ser Asp Tyr Ile Leu
        195                 200                 205

Asn Lys Ser Val Glu Lys Gln Phe Lys Ala Phe Arg Arg Gly Phe His
    210                 215                 220

Met Val Thr Asn Glu Ser Pro Leu Lys Tyr Leu Phe Arg Pro Glu Glu
225                 230                 235                 240

Ile Glu Leu Leu Ile Cys Gly Ser Arg Asn Leu Asp Phe Gln Ala Leu
                245                 250                 255

Glu Glu Thr Thr Glu Tyr Asp Gly Gly Tyr Thr Arg Asp Ser Val Leu
            260                 265                 270

Ile Arg Glu Phe Trp Glu Ile Val His Ser Phe Thr Asp Glu Gln Lys
        275                 280                 285

Arg Leu Phe Leu Gln Phe Thr Thr Gly Thr Asp Arg Ala Pro Val Gly
    290                 295                 300

Gly Leu Gly Lys Leu Lys Met Ile Ile Ala Lys Asn Gly Pro Asp Thr
305                 310                 315                 320

Glu Arg Leu Pro Thr Ser His Thr Cys Phe Asn Val Leu Leu Leu Pro
                325                 330                 335

Glu Tyr Ser Ser Lys Glu Lys Leu Lys Glu Arg Leu Leu Lys Ala Ile
            340                 345                 350

Thr Tyr Ala Lys Gly Phe Gly Met Leu
            355                 360
```